(12) United States Patent
Fadli et al.

(10) Patent No.: US 9,980,893 B2
(45) Date of Patent: May 29, 2018

(54) DYE COMPOSITION COMPRISING A 1,2,3,4-TETRAHYDROPYRIDO[2,3-B]PYRAZIN-7-AMINE COMPOUND

(71) Applicant: L'OREAL, Paris (FR)

(72) Inventors: Aziz Fadli, Chelles (FR); Stéphane Blais, Palaiseau (FR)

(73) Assignee: L'OREAL, Paris (FR)

( * ) Notice: Subject to any disclaimer, the term of this patent is extended or adjusted under 35 U.S.C. 154(b) by 0 days. days.

(21) Appl. No.: 15/106,083

(22) PCT Filed: Dec. 19, 2014

(86) PCT No.: PCT/EP2014/078856
§ 371 (c)(1),
(2) Date: Jun. 17, 2016

(87) PCT Pub. No.: WO2015/092011
PCT Pub. Date: Jun. 25, 2015

(65) Prior Publication Data
US 2016/0303018 A1  Oct. 20, 2016

(30) Foreign Application Priority Data
Dec. 20, 2013 (FR) ...................................... 13 63269

(51) Int. Cl.
*A61Q 5/10* (2006.01)
*A61K 8/49* (2006.01)
*C07D 471/04* (2006.01)
*A61Q 5/06* (2006.01)

(52) U.S. Cl.
CPC .............. *A61K 8/494* (2013.01); *A61Q 5/065* (2013.01); *A61Q 5/10* (2013.01); *C07D 471/04* (2013.01); *A61K 2800/4324* (2013.01)

(58) Field of Classification Search
CPC ........ A61Q 5/10; A61Q 5/065; C07D 471/04; A61K 8/494; A61K 2800/4324
See application file for complete search history.

(56) References Cited

U.S. PATENT DOCUMENTS

| | | |
|---|---|---|
| 3,536,436 A | 10/1970 | Lange |
| 4,003,699 A | 1/1977 | Rose et al. |
| RE30,199 E | 1/1980 | Rose et al. |

(Continued)

FOREIGN PATENT DOCUMENTS

| | | |
|---|---|---|
| DE | 2359399 A1 | 6/1975 |
| DE | 3843892 A1 | 6/1990 |

(Continued)

OTHER PUBLICATIONS

STIC Search Report dated Sep. 14, 2016.*
International Search Report for PCT/EP2014/0788565, dated Mar. 3, 2015.

*Primary Examiner* — Eisa B Elhilo
(74) *Attorney, Agent, or Firm* — The Marbury Law Group, PLLC

(57) ABSTRACT

The invention relates to a 1,2,3,4-tetrahydropyrido[2,3-b]pyrazin-7-amine compound of formula (I) below, addition salts thereof, optical isomers, geometrical isomers and tautomers thereof and/or solvates thereof: in which: .$R_2$, $R_3$, $R_4$, $R_5$, and $R_7$ independently represent: a hydrogen or halogen atom; a $C_1$-$C_4$ alkyl radical; a $C_1$-$C_4$ hydroxyalkyl radical; a carboxyl radical; a ($C_1$-$C_4$)alkoxycarbonyl radical; .R1 and R6, which may be identical or different, represent: hydrogen atom; $C_1$-$C_{10}$ and preferably Ci-C6 alkyl radical,—optionally interrupted with one or more heteroatoms chosen from O and S or with one or more groups—NR and/or—optionally terminating with at least one group—$NX_1X_2$ or at least one group —$OX_3$, .$X_1$ and X2 independently denote—a hydrogen atom, a linear $C_1$-$C_6$ alkyl radical, a branched $C_3$-$C_6$ alkyl radical, a linear $C_1$-$C_6$ hydroxyalkyl radical or a branched $C_3$-$C_6$ hydroxyalkyl radical, X1 and X2 may form, with the nitrogen atom that bears them, a saturated or unsaturated 5- to 8-membered heterocycle, in which one of the ring members may be a heteroatom chosen from O, S and N; the said heterocycle possibly being substituted with one or more linear or branched $C_1$-$C_4$ alkyl or $C_1$-$C_4$ hydroxyalkyl radicals, .X3 denotes—a hydrogen atom—a linear C1-C4 or branched C3-C4 alkyl radical, and .R denotes—a hydrogen atom—a linear C1-C4 alkyl radical.

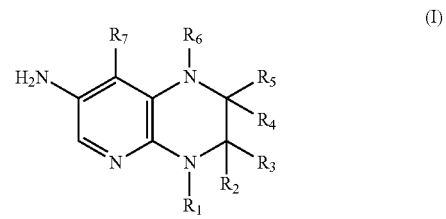

(I)

20 Claims, No Drawings

(56) References Cited

U.S. PATENT DOCUMENTS

| | | | |
|---|---|---|---|
| 4,823,985 A | 4/1989 | Grollier et al. | |
| 5,061,289 A | 10/1991 | Clausen et al. | |
| 5,380,340 A | 1/1995 | Neunhoeffer et al. | |
| 5,534,267 A | 7/1996 | Neunhoeffer et al. | |
| 5,620,978 A | 4/1997 | Cai et al. | |
| 5,663,366 A | 9/1997 | Neunhoeffer et al. | |
| 5,752,984 A | 5/1998 | Knuebel et al. | |
| 5,766,576 A | 6/1998 | Löwe et al. | |
| 6,099,592 A | 8/2000 | Vidal et al. | |
| 6,099,593 A | 8/2000 | Terranova et al. | |
| 6,248,137 B1 | 6/2001 | Terranova et al. | |
| 6,284,003 B1 | 9/2001 | Rose et al. | |
| 6,338,741 B1 | 1/2002 | Vidal et al. | |
| 6,645,258 B2 | 11/2003 | Vidal et al. | |
| 6,730,789 B1 | 5/2004 | Birault et al. | |
| 6,783,557 B1 | 8/2004 | Terranova et al. | |
| 7,601,716 B2 * | 10/2009 | Dorsey | C07D 471/04 514/249 |
| 2001/0020310 A1 | 9/2001 | Terranova et al. | |
| 2002/0050013 A1 | 5/2002 | Vidal et al. | |
| 2003/0019051 A9 | 1/2003 | Vidal et al. | |
| 2005/0166335 A1 | 8/2005 | Vidal et al. | |
| 2007/0136959 A1 | 6/2007 | Fadli | |
| 2007/0143935 A1 | 6/2007 | Fadli et al. | |
| 2008/0071092 A1 | 3/2008 | Vidal et al. | |
| 2010/0115711 A1 | 5/2010 | Fadli et al. | |

FOREIGN PATENT DOCUMENTS

| | | |
|---|---|---|
| DE | 4133957 A1 | 4/1993 |
| DE | 19543988 A1 | 5/1997 |
| EP | 0770375 A1 | 5/1997 |
| EP | 0926149 A1 | 6/1999 |
| EP | 1792606 A1 | 6/2007 |
| EP | 1792903 A1 | 6/2007 |
| FR | 2586913 A | 3/1987 |
| FR | 2733749 A1 | 11/1996 |
| FR | 2801308 A1 | 5/2001 |
| FR | 2866338 A1 | 8/2005 |
| FR | 2927078 A1 | 8/2009 |
| GB | 1026978 A | 4/1966 |
| GB | 1153196 A | 5/1969 |
| JP | 02-019576 A | 1/1990 |
| JP | 05-163124 A | 6/1993 |
| WO | 94/08969 A1 | 4/1994 |
| WO | 94/08970 A1 | 4/1994 |
| WO | 96/15765 A1 | 5/1996 |
| WO | 97/49378 A1 | 12/1997 |
| WO | 00/43396 A1 | 7/2000 |
| WO | 2007/130468 A2 | 11/2007 |
| WO | 2009/098257 A1 | 8/2009 |

* cited by examiner

DYE COMPOSITION COMPRISING A 1,2,3,4-TETRAHYDROPYRIDO[2,3-B]PYRAZIN-7-AMINE COMPOUND

CROSS REFERENCE TO RELATED APPLICATIONS

This is a national stage application of PCT/EP2014/078856, filed internationally on Dec. 19, 2014, which claims priority to French Application No. 1363269, filed on Dec. 20, 2013, both of which are incorporated by reference herein in their entireties.

The present invention relates to particular novel 1,2,3,4-tetrahydropyrido[2,3-β]pyrazin-7-amine compounds, to a dye composition comprising the same and also to a dyeing process using these compounds.

It is known practice to dye keratin fibres and in particular human hair with dye compositions containing oxidation dye precursors, which are generally known as oxidation bases, such as ortho- or para-phenylenediamines, ortho- or para-aminophenols and heterocyclic compounds. These oxidation bases are colourless or weakly coloured compounds, which, when combined with oxidizing products, may give rise to coloured compounds via a process of oxidative condensation.

It is also known that the shades obtained with these oxidation bases may be varied by combining them with couplers or colour modifiers, the latter being chosen especially from aromatic meta-diamines, meta-aminophenols, meta-diphenols and certain heterocyclic compounds such as indole compounds.

The variety of molecules used as oxidation bases and couplers allows a wide range of colours to be obtained.

The "permanent" colouring obtained by means of these couplers and oxidation dyes must moreover satisfy a certain number of requirements. Thus, it should have no toxicological drawbacks, it should allow shades to be obtained in the desired intensity, and it should show good resistance to external agents such as light, bad weather, washing, permanent waving treatments, perspiration and rubbing.

The dyes should also allow grey hair to be covered and, finally, they should be as unselective as possible, i.e. they should produce the smallest possible differences in colour along the same keratin fibre, which in general is differently sensitized (i.e. damaged) between its end and its root.

The aim of the present invention is to obtain a hair dye composition that has improved dyeing properties in terms of intensity or chromaticity and/or selectivity and/or resistance to external agents.

Surprisingly and advantageously, the Applicant has just discovered a novel family of couplers consisting of 1,2,3,4-tetrahydropyrido[2,3-b]pyrazin-7-amines. These couplers result in a wide range of colours in oxidation dyeing. They especially make it possible to broaden the colour range. Furthermore, these 1,2,3,4-tetrahydropyrido[2,3-b]pyrazin-7-amines make it possible to obtain powerful, chromatic and sparingly selective colourings in varied shades, which show good resistance to the various external attacking factors to which the hair may be subjected (shampooing, light, sweat or permanent reshaping).

One subject of the invention is thus a 1,2,3,4-tetrahydropyrido[2,3-b]pyrazin-7-amine compound of formula (I) below, addition salts thereof, optical isomers, geometrical isomers and tautomers thereof and/or solvates thereof:

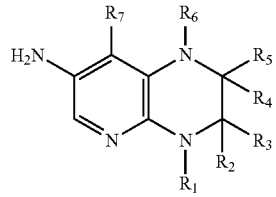

in which:
R$_2$, R$_3$, R$_4$, R$_5$, and R$_7$ independently represent:
  a hydrogen or halogen atom;
  a C$_1$-C$_4$ alkyl radical;
  a C$_1$-C$_4$ hydroxyalkyl radical;
  a carboxyl radical;
  a (C$_1$-C$_4$)alkoxycarbonyl radical;
R1 and R6, which may be identical or different, represent:
  a hydrogen atom;
  a C$_1$-C$_{10}$ alkyl radical;
    optionally interrupted with one or more heteroatoms chosen from O and S or with one or more groups —NR and/or
    optionally terminating with at least one group —NX$_1$X$_2$ or at least one group —OX$_3$,
X$_1$ and X$_2$ independently denote
  a hydrogen atom, a linear C$_1$-C$_6$ alkyl radical, a branched C$_3$-C$_6$ alkyl radical, a linear C$_1$-C$_6$ hydroxyalkyl radical or a branched C$_3$-C$_6$ hydroxyalkyl radical,
  X1 and X2 may form, with the nitrogen atom that bears them, a saturated or unsaturated 5- to 8-membered heterocycle, in which one of the ring members may be a heteroatom chosen from O, S and N; the said heterocycle possibly being substituted with one or more linear or branched C$_1$-C$_4$ alkyl or C$_1$-C$_4$ hydroxyalkyl radicals,
X3 denotes
  a hydrogen atom
  a linear C1-C4 or branched C3-C4 alkyl radical,
R denotes
  a hydrogen atom
  a linear C1-C4 alkyl radical.

A subject of the invention is also a composition for dyeing keratin fibres, comprising, in a suitable dyeing medium, at least one compound of formula (I) as defined above. A subject of the invention is also a process for dyeing keratin fibres, which consists in applying this composition to the said fibres.

Another subject of the invention is the use of the composition of the present invention for dyeing keratin fibres, in particular human keratin fibres such as the hair.

The invention also relates to multi-compartment devices comprising compositions containing one or more couplers chosen from the compound of formula (I) or an addition salt thereof.

Finally, a subject of the invention is a dyeing kit comprising, on the one hand, a dye composition containing a compound of formula (I) and, on the other hand, a composition containing an oxidizing agent.

The compounds of the present invention make it possible in particular to obtain compositions for dyeing keratin fibres that are suitable for use in oxidation dyeing and that make it possible to obtain a hair colouring that has improved dyeing properties in terms of intensity or chromaticity and/or selectivity and/or resistance to external agents such as shampoo, sweat, permanent reshaping and light.

Within the meaning of the present invention and unless otherwise indicated:
- an "alkyl radical" is a linear or branched $C_1$-$C_{20}$ and preferably $C_1$-$C_8$ hydrocarbon-based radical;
- an "alkenylene radical" is an unsaturated hydrocarbon-based divalent radical as defined previously, which may contain from 1 to 4 conjugated or unconjugated double bonds —C=C—; the alkenylene group particularly contains 1 or 2 unsaturations;
- the term "optionally substituted" applied to the alkyl radical means that the said alkyl radical may be substituted with one or more radicals chosen from the following radicals: i) hydroxyl, ii) $C_1$-$C_4$ alkoxy, iii) acylamino, iv) amino optionally substituted with one or two identical or different $C_1$-$C_4$ alkyl radicals, the said alkyl radicals possibly forming with the nitrogen atom that bears them a 5- to 7-membered heterocycle, optionally comprising another nitrogen or non-nitrogen heteroatom; v) or a quaternary ammonium group —N$^+$R'R''R''', M$^-$ for which R', R'' and R''', which may be identical or different, represent a hydrogen atom or a $C_1$-$C_4$ alkyl group, or else —N$^+$R'R''R''' forms a heteroaryl such as imidazolium optionally substituted with a $C_1$-$C_4$ alkyl group, and M$^-$ represents the counterion of the corresponding organic acid, mineral acid or halide;
- an "alkoxy radical" is an alkyl-oxy radical for which the alkyl radical is a linear or branched $C_1$-$C_{16}$ and preferentially $C_1$-$C_8$ hydrocarbon-based radical;
- when the alkoxy group is optionally substituted, this implies that the alkyl group is optionally substituted as defined hereinabove;
- the term "at least one" is equivalent to the term "one or more"; and
- the term "inclusively" for a range of concentrations means that the limits of that range are included in the defined range.

It should be noted that, in the text hereinbelow, unless otherwise indicated, the limits of a range of values are included in that range.

Compound of Formula (I)

One subject of the invention is thus a 1,2,3,4-tetrahydro-pyrido[2,3-b]pyrazin-7-amine compound of formula (I) below, addition salts thereof, optical isomers, geometrical isomers and tautomers thereof and/or solvates thereof:

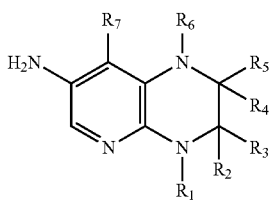

in which:
$R_2$, $R_3$, $R_4$, $R_5$, and $R_7$ independently represent:
- a hydrogen or halogen atom;
- a $C_1$-$C_4$ alkyl radical;
- a $C_1$-$C_4$ hydroxyalkyl radical;
- a carboxyl radical;
- a ($C_1$-$C_4$)alkoxycarbonyl radical;

R1 and R6, which may be identical or different, represent:
- a hydrogen atom;
- a $C_1$-$C_{10}$ and preferably $C_1$-$C_6$ alkyl radical,
  - optionally interrupted with one or more heteroatoms chosen from O and S or with one or more groups —NR and/or
  - optionally terminating with at least one group —NX$_1$X$_2$ or a group —OX$_3$, $X_1$ and $X_2$ independently denote
- a hydrogen atom, a linear $C_1$-$C_6$ alkyl radical, a branched $C_3$-$C_6$ alkyl radical, a linear $C_1$-$C_6$ hydroxyalkyl radical or a branched $C_3$-$C_6$ hydroxyalkyl radical,
- X1 and X2 may form, with the nitrogen atom that bears them, a saturated or unsaturated 5- to 8-membered heterocycle, in which one of the ring members may be a heteroatom chosen from O, S and N; the said heterocycle possibly being substituted with one or more linear or branched $C_1$-$C_4$ alkyl or $C_1$-$C_4$ hydroxyalkyl radicals,
- a ($C_1$-$C_4$)alkoxycarbonyl radical, X3 denotes
- a hydrogen atom
- a linear C1-C4 or branched C3-C4 alkyl radical, R denotes
- a hydrogen atom
- a linear C1-C4 alkyl radical.

As examples of saturated or unsaturated 5- to 8-membered heterocyclic radicals in which one of the ring members may be a heteroatom chosen from O, S and N, mention may be made of imidazole, pyridine, piperazine, pyrrolidine, morpholine, pyrimidine, thiazole, benzimidazole, benzothiazole, oxazole, benzotriazole, triazole, benzoxazole and piperidine rings.

Preferably, $R_2$, $R_3$, $R_4$, $R_5$ and $R_7$, which may be identical or different, represent a hydrogen atom or a $C_1$-$C_4$ alkyl radical.

Even more preferably, $R_2$, $R_3$, $R_4$, $R_5$ and $R_7$ are identical and represent a hydrogen atom.

Preferably:
R1 and R6, which may be identical or different, represent:
- a hydrogen atom;
- a C1-C6 alkyl radical;
  - optionally interrupted with a heteroatom chosen from O and S or with a group —NR; and/or
  - optionally terminating with at least one group —NX1X2 or at least one group —OX$_3$, and
X1 and X2 independently denote
- a linear C1-C4 alkyl radical or a branched C3-C4 alkyl radical,
- a linear C1-C4 hydroxyalkyl radical or a branched C3-C4 hydroxyalkyl radical,
- X1 and X2 may form, with the nitrogen atom that bears them, a saturated or unsaturated 5- to 7-membered heterocycle, in which one of the ring members may be a heteroatom chosen from O, S and N; the said heterocycle possibly being substituted with one or more linear or branched $C_1$-$C_4$ alkyl or $C_1$-$C_4$ hydroxyalkyl radicals.

Preferably, the said saturated or unsaturated 5- to 7-membered heterocyclic radical in which one of the ring members may be a heteroatom chosen from O, S and N is chosen from imidazole, piperazine, pyrrolidine, morpholine and piperidine rings.

More preferably, X3 denotes a hydrogen atom.

Preferably, R denotes a hydrogen atom or a linear $C_1$-$C_4$ alkyl radical.

According to one embodiment, in formula (I):
$R_2$, $R_3$, $R_4$, $R_5$ and $R_7$ are identical and represent a hydrogen atom.

R1 and R6, which may be identical or different, represent:
a hydrogen atom;
a C1-C6 alkyl radical
optionally interrupted with a heteroatom chosen from O and S or with a group —NR and/or
optionally terminating with at least one group —NX1X2 or a group —OX₃,
and
X1 and X2 independently denote
a linear C1-C4 alkyl radical or a branched C3-C4 alkyl radical,
a linear C1-C4 hydroxyalkyl radical or a branched C3-C4 hydroxyalkyl radical,
X1 and X2 may form, with the nitrogen atom that bears them, a saturated or unsaturated 5- to 7-membered heterocycle, in which one of the ring members may be a heteroatom chosen from O, S and N; the said heterocycle possibly being substituted with one or more linear or branched $C_1$-$C_4$ alkyl or $C_1$-$C_4$ hydroxyalkyl radicals,
X3 denotes a hydrogen atom and
R denotes a hydrogen atom or a linear $C_1$-$C_4$ alkyl radical, preferably a hydrogen atom or a methyl radical.

Preferably, the said saturated or unsaturated 5- to 7-membered heterocyclic radical in which one of the ring members may be a heteroatom chosen from O, S and N is chosen from imidazole, piperazine, pyrrolidine, morpholine and piperidine rings.

The compounds of general formula (I) may be in free form or in the form of salts, such as addition salts with a mineral acid preferably chosen from hydrochloric acid, hydrobromic acid, sulfuric acid and phosphoric acid or with an organic acid such as, for example, citric acid, succinic acid, tartaric acid, lactic acid, 4-toluylsulfonic acid, benzenesulfonic acid, acetic acid, para-toluenesulfonic acid, formic acid and methanesulfonic acid.

The compounds of general formula (I) may also be in the form of solvates, for example a hydrate or a solvate of a linear or branched alcohol such as ethanol or isopropanol.

I/ According to a first particular embodiment of the invention, the compounds of formula (I) are such that:
R₂, R₃, R₄, R₅ and R₇ are identical and represent a hydrogen atom,
R1 and R6 are identical and represent a hydrogen atom or a C1-C6 alkyl radical, optionally terminating with at least one, preferably one, group chosen from —NX1X2 and —OH, and
X1 and X2 independently denote
a linear C1-C4 alkyl radical or a branched C3-C4 alkyl radical,
a linear C1-C4 hydroxyalkyl radical or a branched C3-C4 hydroxyalkyl radical,
X1 and X2 possibly forming, with the nitrogen atom that bears them, a saturated or unsaturated 5- to 7-membered heterocycle, in which one of the ring members may be a heteroatom chosen from O, S and N; the said heterocycle possibly being substituted with one or more linear or branched $C_1$-$C_4$ alkyl or $C_1$-$C_4$ hydroxyalkyl radicals.

The saturated or unsaturated 5- to 7-membered heterocyclic radical in which one of the ring members may be a heteroatom chosen from O, S and N may be chosen from imidazole, piperazine, pyrrolidine, morpholine and piperidine rings.

According to this first embodiment, the compounds that are particularly preferred are the following:

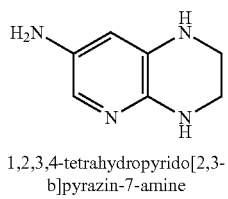

1,2,3,4-tetrahydropyrido[2,3-b]pyrazin-7-amine

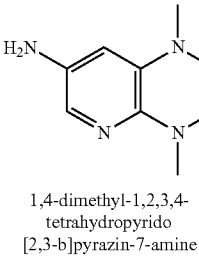

1,4-dimethyl-1,2,3,4-tetrahydropyrido[2,3-b]pyrazin-7-amine

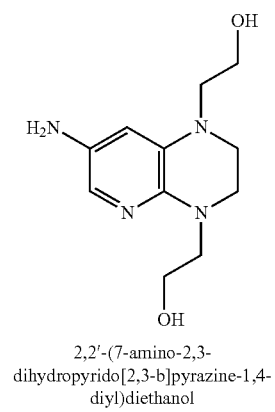

2,2'-(7-amino-2,3-dihydropyrido[2,3-b]pyrazine-1,4-diyl)diethanol

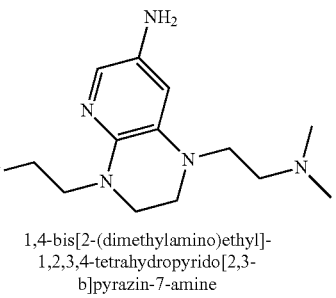

1,4-bis[2-(dimethylamino)ethyl]-1,2,3,4-tetrahydropyrido[2,3-b]pyrazin-7-amine

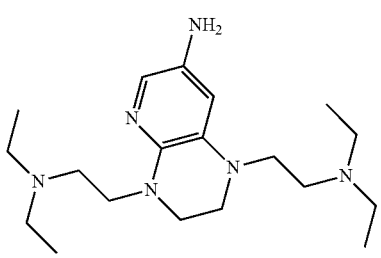

11,4-bis[2-(diethylamino)ethyl]-1,2,3,4-tetrahydropyrido[2,3-b]pyrazin-7-amine

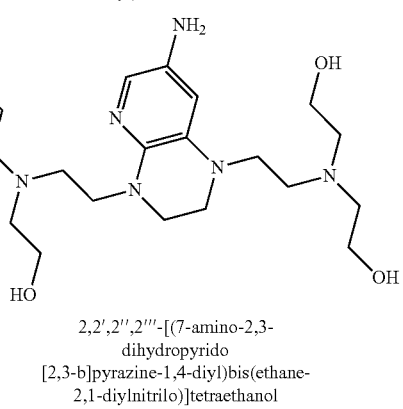

2,2',2'',2'''-[(7-amino-2,3-dihydropyrido[2,3-b]pyrazine-1,4-diyl)bis(ethane-2,1-diylnitrilo)]tetraethanol

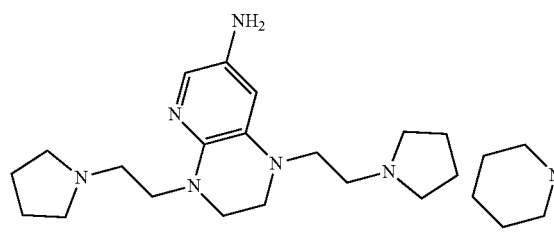

1,4-bis[2-(pyrrolidin-1-yl)ethyl]-1,2,3,4-tetrahydropyrido[2,3-b]pyrazin-7-amine

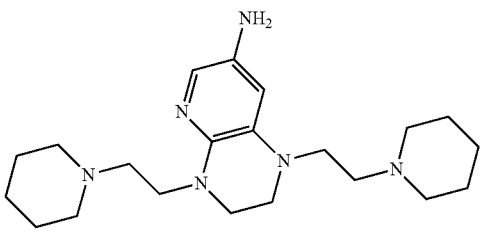

1,4-bis[2-(piperidin-1-yl)ethyl]-1,2,3,4-tetrahydropyrido[2,3-b]pyrazin-7-amine

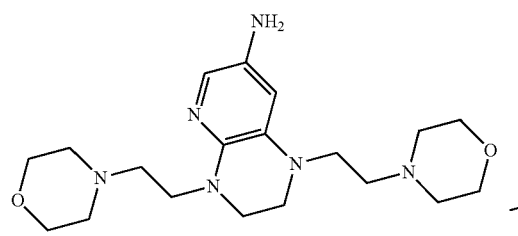

1,4-bis[2-(morpholin-4-yl)ethyl]-1,2,3,4-tetrahydropyrido[2,3-b]pyrazin-7-amine

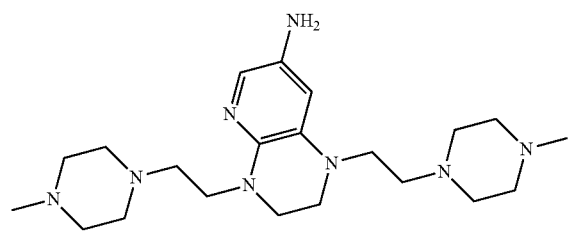

1,4-bis[2-(4-methylpiperazin-1-yl)ethyl]-1,2,3,4-tetrahydropyrido[2,3-b]pyrazin-7-amine

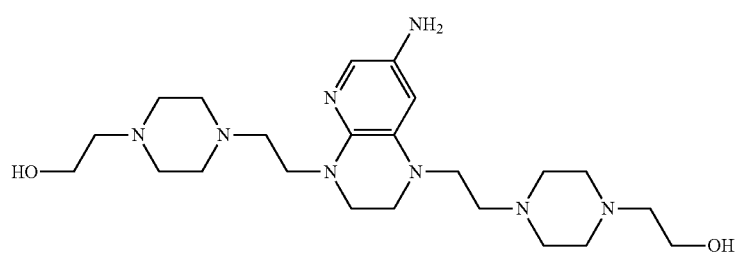

2,2'-[(7-amino-2,3-dihydropyrido[2,3-b]pyrazine-1,4-diyl)bis(ethane-2,1-diylpiperazine-4,1-diyl)]diethanol

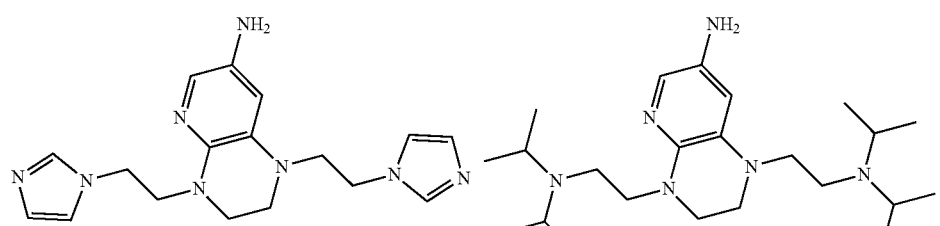

1,4-bis[2-(1H-imidazol-1-yl)ethyl]-1,2,3,4-tetrahydropyrido[2,3-b]pyrazin-7-amine

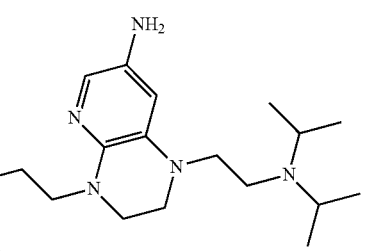

1,4-bis[2-(dipropan-2-ylamino)ethyl]-1,2,3,4-tetrahydropyrido[2,3-b]pyrazin-7-amine

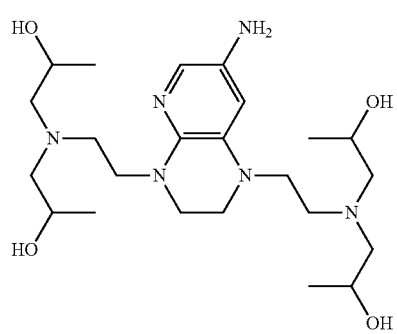

1,1',1'',1'''-[(7-amino-2,3-dihydropyrido[2.3-b]pyrazine-1,4-diyl)bis(ethane-2,1-diylnitrilo)]tetrapropan-2-ol-1-ol

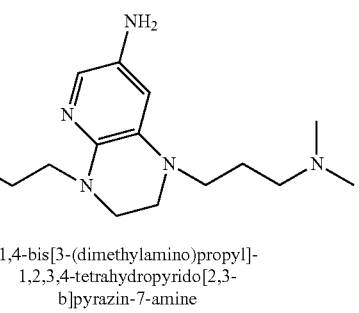

1,4-bis[3-(dimethylamino)propyl]-1,2,3,4-tetrahydropyrido[2,3-b]pyrazin-7-amine

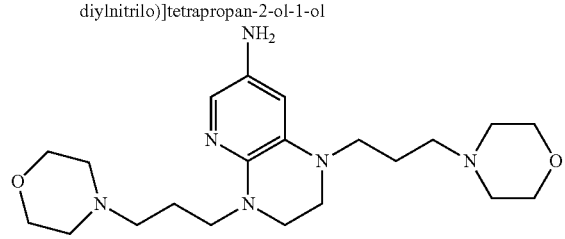

,4-bis[3-(morpholin-4-yl)propyl]-1,2,3,4-tetrahydropyrido[2,3-b]pyrazin-7-amine

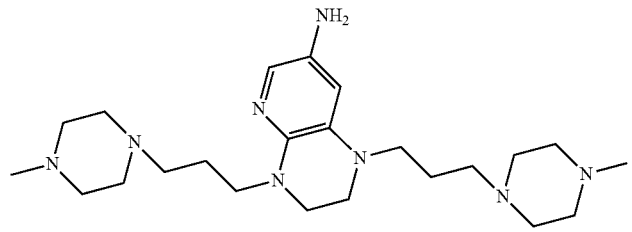

1,4-bis[3-(4-methylpiperazin-1-yl)propyl]-1,2,3,4-tetrahydropyrido[2,3-b]pyrazin-7-amine

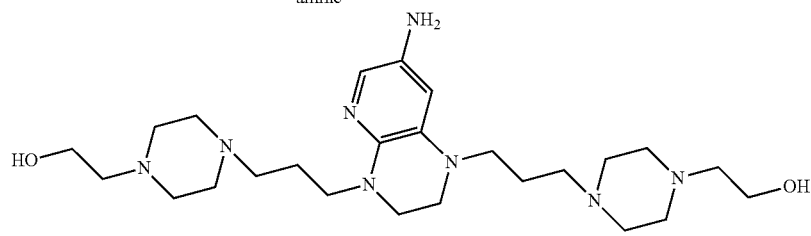

2,2'-[(7-amino-2,3-dihydropyrido[2,3-b]pyrazine-1,4-diyl)bis(propane-3,1-diylpiperazine-4,1-diyl)]diethanol and also the addition salts, optical isomers, geometrical isomers, tautomers and/or solvates thereof.

II/ According to a second embodiment of the invention, the compounds of formula (I) are such that:

$R_2$, $R_3$, $R_4$, $R_5$ and $R_7$ are identical and represent a hydrogen atom, R1 and R6 are identical and represent a C1-C6 alkyl radical interrupted with an oxygen atom or an NH group, optionally terminating with at least one, preferably one, group chosen from —NX1X2 and —OH, and X1 and X2 independently denote
a linear C1-C4 alkyl radical or a branched C3-C4 alkyl radical,
a linear C1-C4 hydroxyalkyl radical or a branched C3-C4 hydroxyalkyl radical,
X1 and X2 possibly forming, with the nitrogen atom that bears them, a saturated or unsaturated 5- to 7-membered heterocycle, in which one of the ring members may be a heteroatom chosen from O, S and N; the said heterocycle possibly being substituted with one or more linear or branched $C_1$-$C_4$ alkyl or $C_1$-$C_4$ hydroxyalkyl radicals.

The saturated or unsaturated 5- to 7-membered heterocyclic radical in which one of the ring members may be a heteroatom chosen from O, S and N may be chosen from imidazole, piperazine, pyrrolidine, morpholine and piperidine rings.

According to this embodiment, the compounds that are particularly preferred are chosen from:

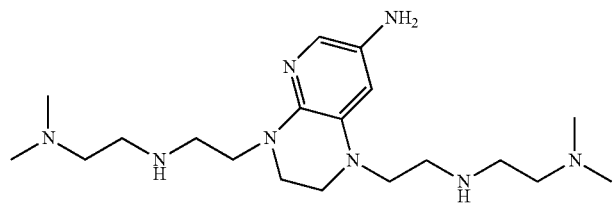

N1,N1'-[(7-amino-2,3-
dihydropyrido[2,3-b]pyrazine-1,4-
diyl)diethane-2,1-diyl]bis(N2,N2-
dimethylethane-1,2-diamine)

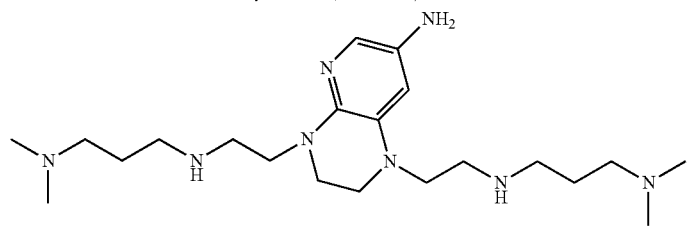

N1,N1'-[(7-amino-2,3-
dihydropyrido[2,3-b]pyrazine-1,4-
diyl)diethane-2,1-diyl]bis(N3,N3-
dimethylpropane-1,3-diamine)

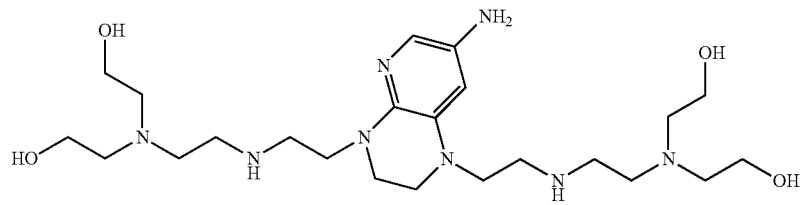

2,2',2'',2'''-[(7-amino-2,3-
dihydropyrido[2,3-b]pyrazine-1,4-
diyl)bis(ethane-2,1-
diyliminoethane-2,1-
diylnitrilo)]tetraethanol

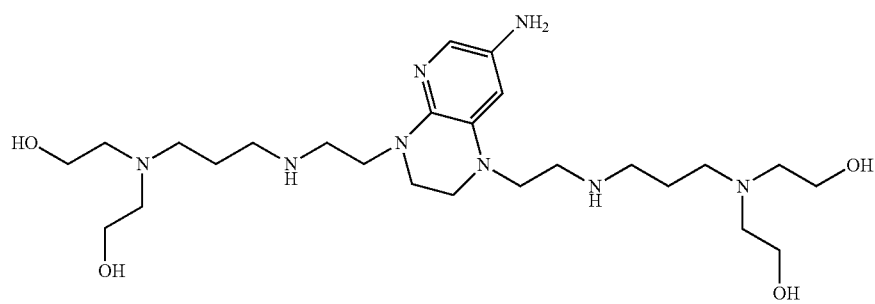

2,2',2'',2'''-[(7-amino-2,3-
dihydropyrido[2,3-b]pyrazine-1,4-
diyl)bis(ethane-2,1-
diyliminopropane-3,1-
diylnitrilo)]tetraethanol -continued

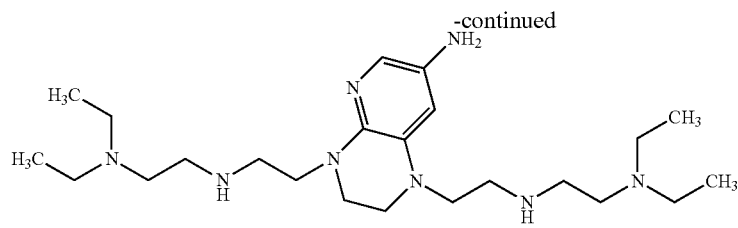

N1,N1'-[(7-amino-2,3-
dihydropyrido[2,3-b]pyrazine-1,4-
diyl)diethane-2,1-diyl]bis(N2,N2-
diethylethane-1,2-diamine)

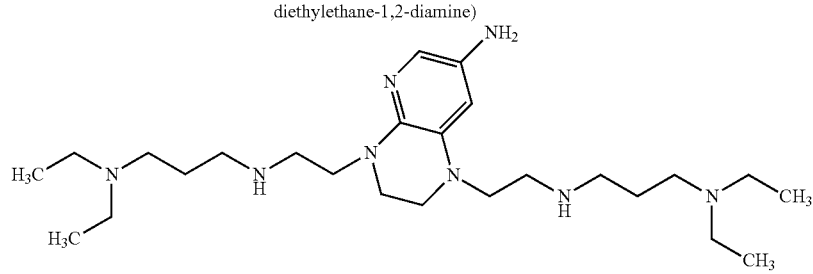

N1,N1'-[(7-amino-2,3-
dihydropyrido[2,3-b]pyrazine-1,4-
diyl)diethane-2,1-diyl]bis(N3,N3-
diethylpropane-1,3-diamine)

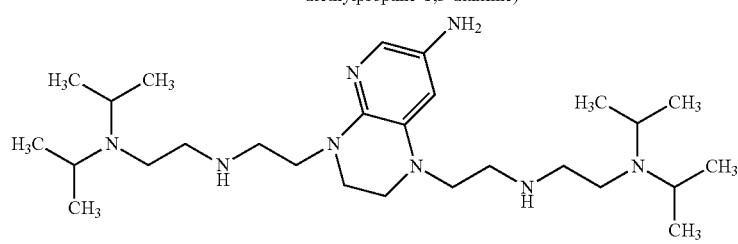

N1,N1'-[(7-amino-2,3-
dihydropyrido[2,3-b]pyrazine-1,4-
diyl)diethane-2,1-diyl]bis[N2,N2-
di(propan-2-yl)ethane-1,2-
diamine]

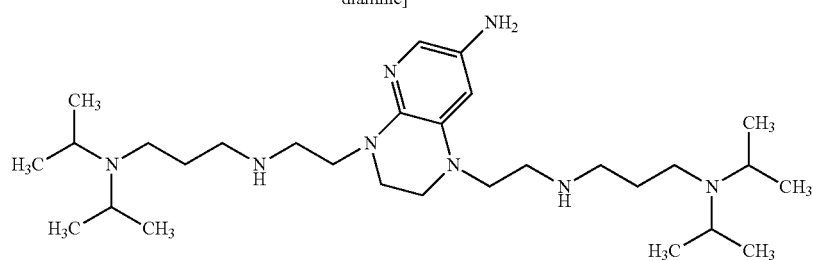

N1,N1'-[(7-amino-2,3-
dihydropyrido[2,3-b]pyrazine-1,4-
diyl)diethane-2,1-diyl]bis[N3,N3-
di(propan-2-yl)propane-1,3-
diamine]

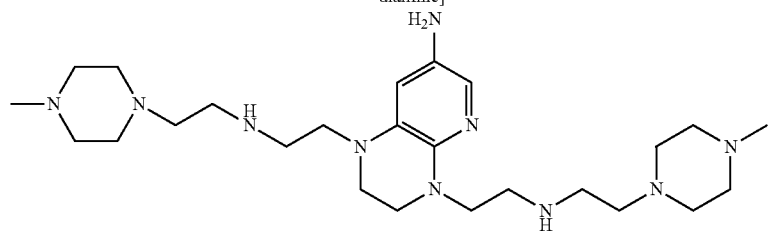

1,4-bis(2-{[2-(4-methylpiperazin-
1-yl)ethyl]amino}ethyl)-1,2,3,4-
tetrahydropyrido[2,3-b]pyrazin-7-
amine

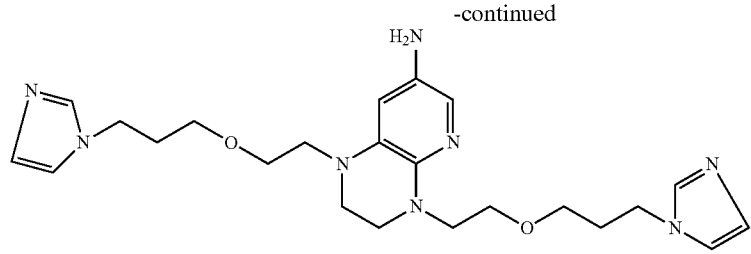

1,4-bis{2-[2-(1H-imidazol-1-yl)ethoxy]ethyl}-1,2,3,4-tetrahydropyrido[2,3-b]pyrazin-7-amine

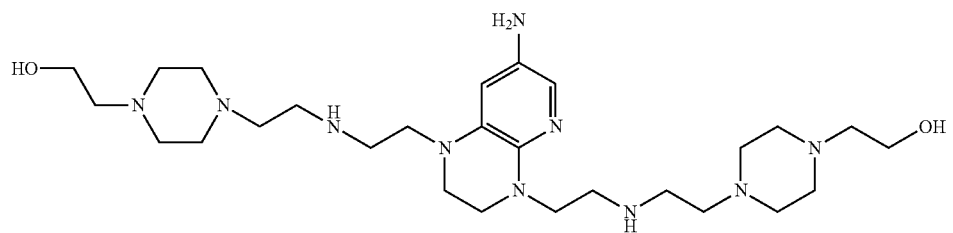

2,2'-[(7-amino-2,3-dihydropyrido[2,3-b]pyrazine-1,4-diyl)bis(ethane-2,1-diyliminoethane-2,1-diylpiperazine-4,1-diyl)]diethanol

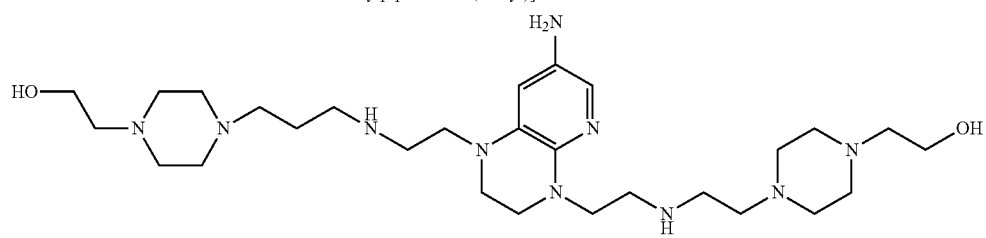

2,2'-[(7-amino-2,3-dihydropyrido[2,3-b]pyrazine-1,4-diyl)bis(ethane-2,1-diyliminoproane-3,1-diylpiperazine-4,1-diyl)]diethanol

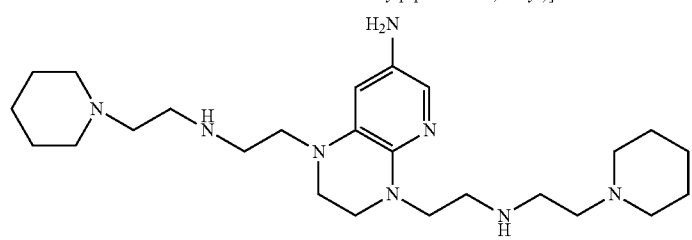

1,4-bis(2-{[2-(piperidin-1-yl)ethyl]amino}ethyl)-1,2,3,4-tetrahydropyrido[2,3-b]pyrazin-7-amine

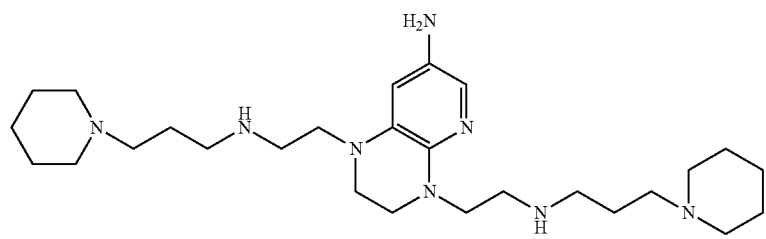

1,4-bis(2-{[3-(piperidin-1-yl)propyl]amino}ethyl)-1,2,3,4-tetrahydropyrido[2,3-b]pyrazin-7-amine -continued

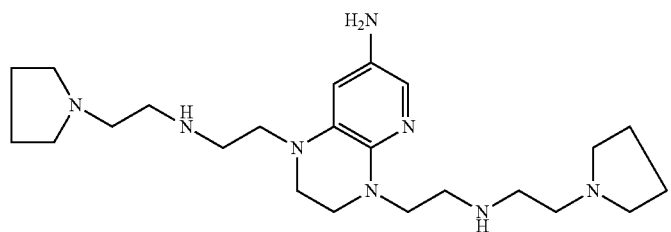

1,4-bis(2-{[2-(pyrrolidin-1-
yl)ethyl]amino}ethyl)-1,2,3,4-
tetrahydropyrido[2,3-b]pyrazin-7-
amine

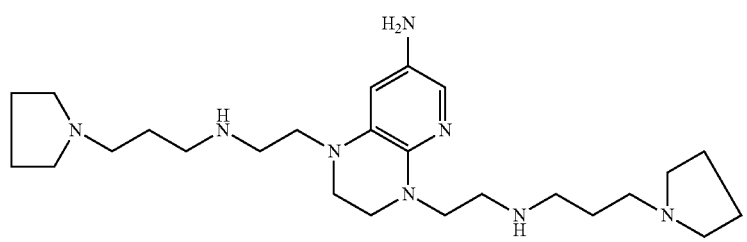

1,4-bis(2-{[3-(pyrrolidin-1-
yl)propyl]amino}ethyl)-1,2,3,4-
tetrahydropyrido[2,3-b]pyrazin-7-
amine

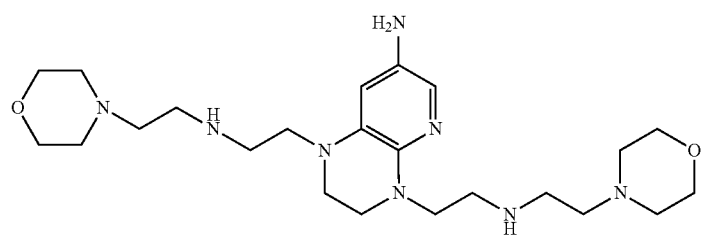

1,4-bis(2-{[2-(morpholin-4-
yl)ethyl]amino}ethyl)-1,2,3,4-
tetrahydropyrido[2,3-b]pyrazin-7-
amine

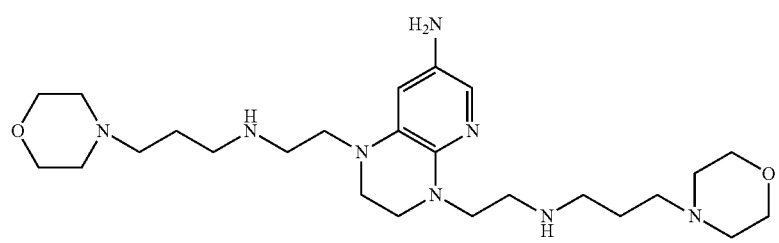

1,4-bis(2-{[3-(morpholin-4-
yl)propyl]amino}ethyl)-1,2,3,4-
tetrahydropyrido[2,3-b]pyrazin-7-
amine

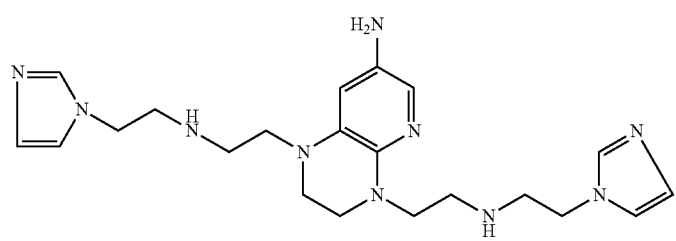

1,4-bis(2-{[2-(1H-imidazol-1-
yl)ethyl]amino}ethyl)-1,2,3,4-
tetrahydropyrido[2,3-b]pyrazin-7-
amine

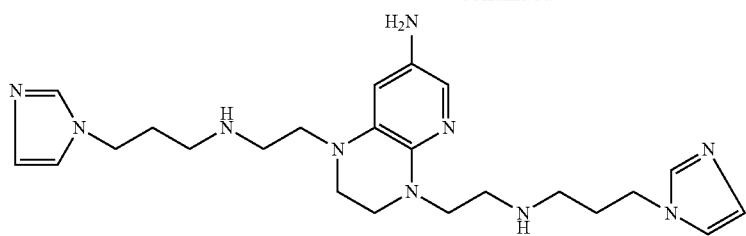

1,4-bis(2-{[3-(1H-imidazol-1-yl)propyl]amino}ethyl)-1,2,3,4-tetrahydropyrido[2,3-b]pyrazin-7-amine

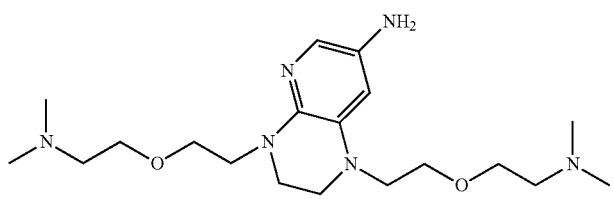

1,4-bis{2-[2-(dimethylamino)ethoxy]ethyl}-1,2,3,4-tetrahydropyrido[2,3-b]pyrazin-7-amine

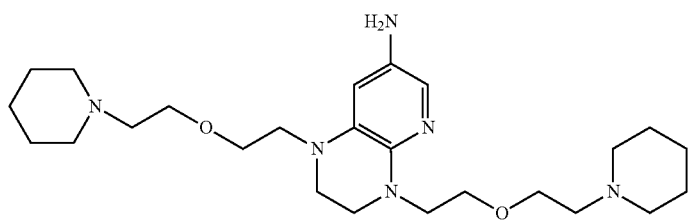

1,4-bis{2-[2-(piperidin-1-yl)ethoxy]ethyl}-1,2,3,4-tetrahydropyrido[2,3-b]pyrazin-7-amine

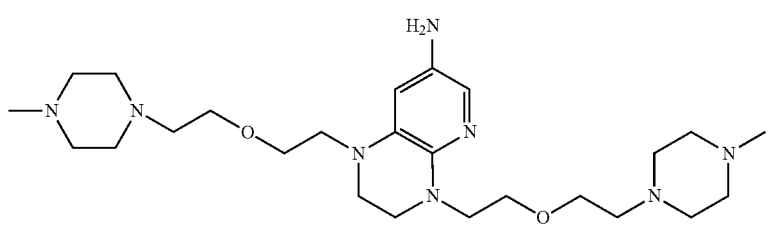

1,4-bis{2-[2-(4-methylpiperazin-1-yl)ethoxy]ethyl}-1,2,3,4-tetrahydropyrido[2,3-b]pyrazin-7-amine

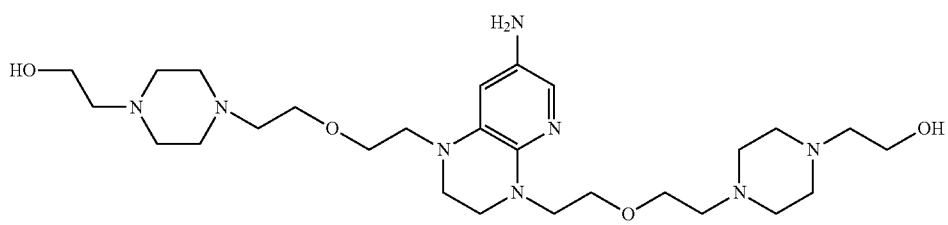

2,2'-[(7-amino-2,3-dihydropyrido[2,3-b]pyrazine-1,4-diyl)bis(ethane-2,1-diyloxyethane-2,1-diylpiperazine-4,1-diyl)]diethanol -continued
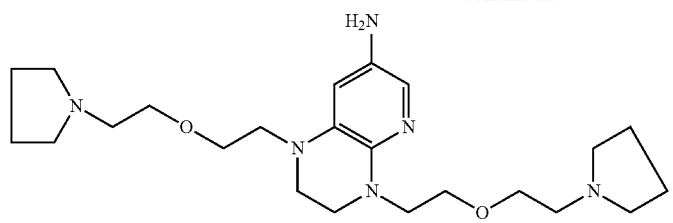
1,4-bis{2-[2-(pyrrolidin-1-
yl)ethoxy]ethyl}-1,2,3,4-
tetrahydropyrido[2,3-b]pyrazin-7-
amine
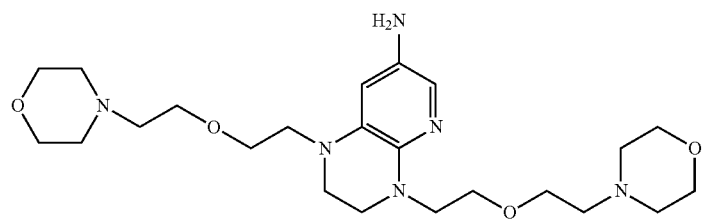
1,4-bis(2-{[2-morpholin-4-
yl]ethyl]amino}ethyl)-1,2,3,4-
tetrahydropyrido[2,3-b]pyrazin-7-
amine
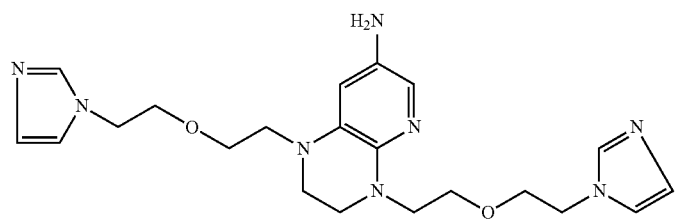
1,4-bis{2-[2-(1H-imidazol-1-
yl)ethoxy]ethyl}-1,2,3,4-
tetrahydropyrido[2,3-b]pyrazin-7-
amine
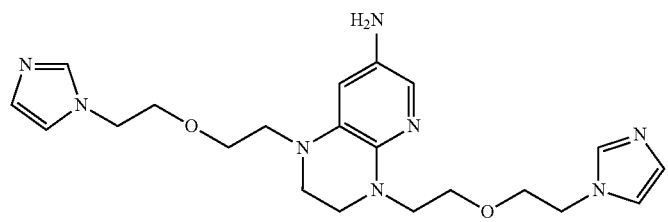
1,4-bis{2-[2-(1H-imidazol-1-
yl)ethoxy]ethyl}-1,2,3,4-
tetrahydropyrido[2,3-b]pyrazin-7-
amine
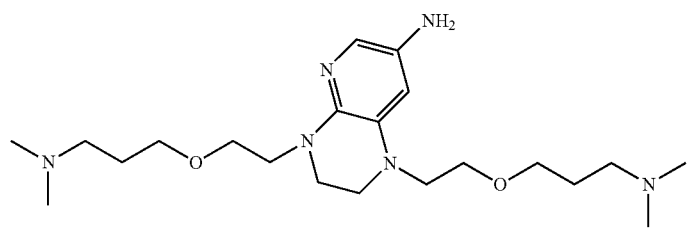
1,4-bis{2-[3-
(dimethylamino)propoxy]ethyl}-
1,2,3,4-tetrahydropyrido[2,3-
b]pyrazin-7-amine

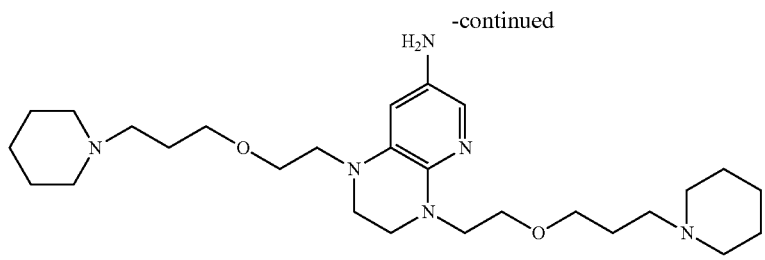

11,4-bis{2-[3-(piperidin-1-yl)propoxy]ethyl}-1,2,3,4-tetrahydropyrido[2,3-b]pyrazin-7-amine

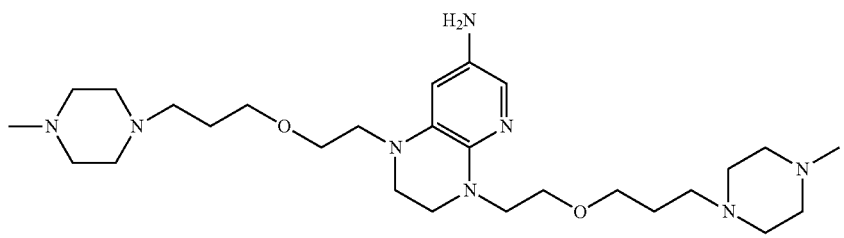

1,4-bis{2-[3-(4-methylpiperazin-1-yl)propoxy]ethyl}-1,2,3,4-tetrahydropyrido[2,3-b]pyrazin-7-amine

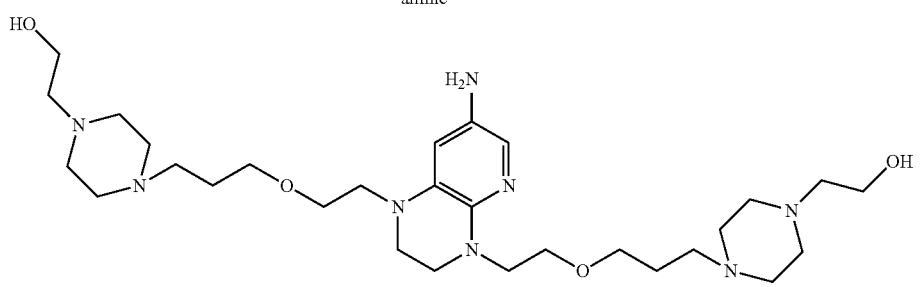

2,2'-[(7-amino-2,3-dihydropyrido[2,3-b]pyrazine-1,4-diyl)bis(ethane-2,1-diyloxypropane-3,1-diylpiperazine-4,1-diyl)]diethanol

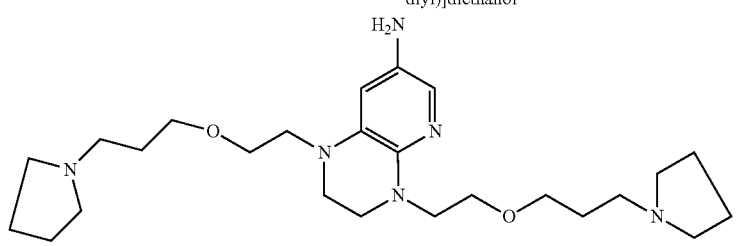

1,4-bis{2-[3-(pyrrolidin-1-yl)propoxy]ethyl}-1,2,3,4-tetrahydropyrido[2,3-b]pyrazin-7-amine

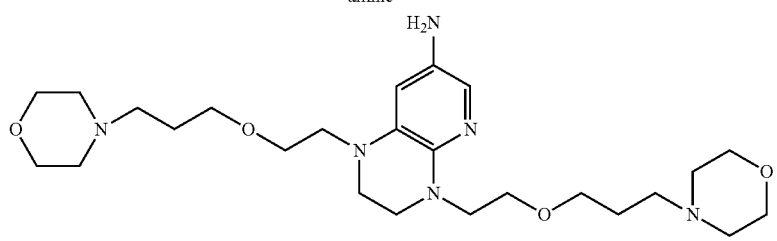

11,4-bis{2-[3-(morpholin-4-yl)propoxy]ethyl}-1,2,3,4-tetrahydropyrido[2,3-b]pyrazin-7-amine

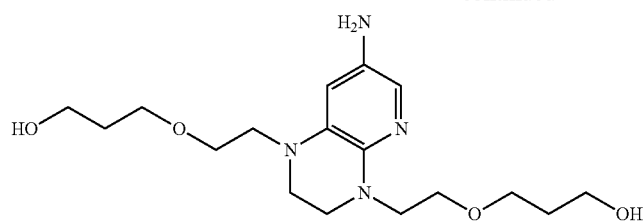

3,3'-[(7-amino-2,3-dihydropyrido[2,3-b]pyrazine-1,4-diyl)bis(ethane-2,1-diyloxy)]dipropan-1-ol

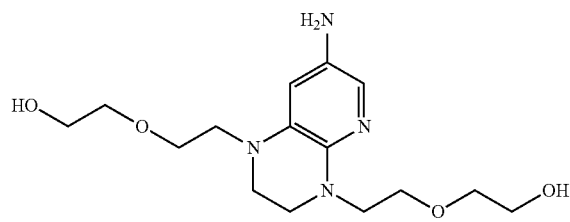

2,2'-[(7-amino-2,3-dihydropyrido[2,3-b]pyrazine-1,4-diyl)bis(ethane-2,1-diyloxy)]diethanol

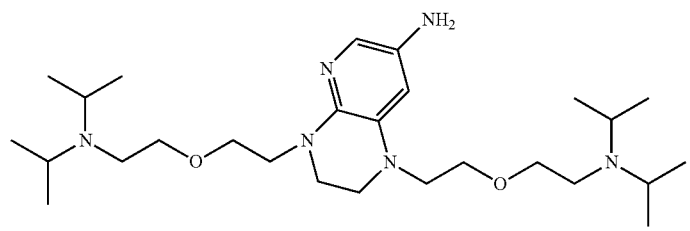

1,4-bis{2-[2-(dipropan-2-ylamino)ethoxy]ethyl}-1,2,3,4-tetrahydropyrido[2,3-b]pyrazin-7-amine

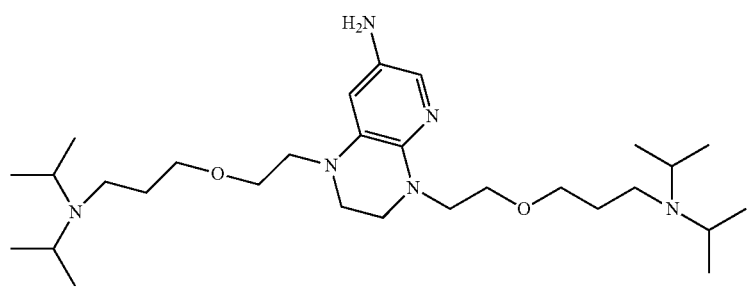

1,4-bis{2-[3-(dipropan-2-ylamino)propoxy]ethyl}-1,2,3,4-tetrahydropyrido[2,3-b]pyrazin-7-amine

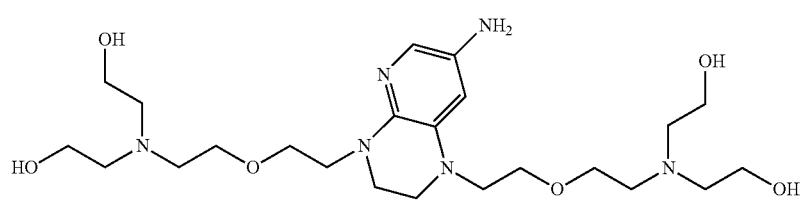

2,2',2'',2'''-[(7-amino-2,3-dihydropyrido[2,3-b]pyrazine-1,4-diyl)bis(ethane-2,1-diyloxyethane-2,1-diylnitrilo)]tetraethanol

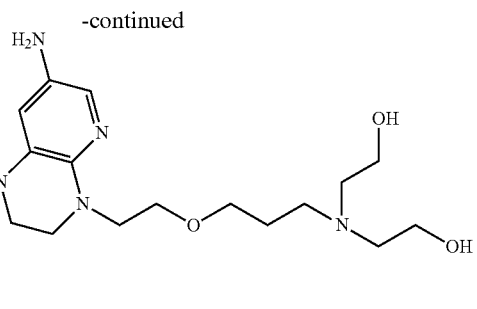

2,2′,2″,2‴-[(7-amino-2,3-
dihydropyrido[2,3-b]pyrazine-1,4-
diyl)bis(ethane-2,1-diyloxypropane-
3,1-diylnitrilo)]tetraethanol and also the addition salts, optical isomers, geometrical isomers, tautomers and/or solvates thereof.

III/ According to a third embodiment of the invention, the compounds of formula (I) are such that:

$R_2$, $R_3$, $R_4$, $R_5$ and $R_7$ are identical and represent a hydrogen atom, R1 and R6 are different and represent, independently, a hydrogen atom or a C1-C6 alkyl radical, optionally terminating with at least one, preferably one, group chosen from NX1X2 and OH, preferably optionally terminating with an OH group, X1 and X2 independently denote a linear C1-C4 alkyl radical or a branched C3-C4 alkyl radical, a linear C1-C4 hydroxyalkyl radical or a branched C3-C4 hydroxyalkyl radical, X1 and X2 possibly forming, with the nitrogen atom that bears them, a saturated or unsaturated 5- to 7-membered heterocycle, in which one of the ring members may be a heteroatom chosen from O, S and N; the said heterocycle possibly being substituted with one or more linear or branched $C_1$-$C_4$ alkyl or $C_1$-$C_4$ hydroxyalkyl radicals.

The saturated or unsaturated 5- to 7-membered heterocyclic radical in which one of the ring members may be a heteroatom chosen from O, S and N may be chosen from imidazole, piperazine, pyrrolidine, morpholine and piperidine rings.

According to this embodiment, the compounds that are particularly preferred are chosen from:

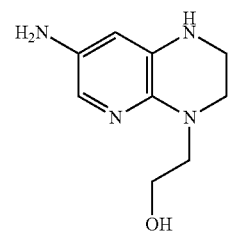

2-(7-amino-2,3-
dihydropyrido[2,3b]pyrazin-4(1H)-
yl)ethanol

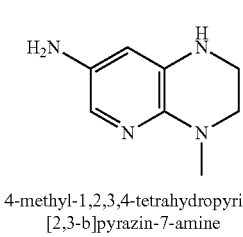

4-methyl-1,2,3,4-tetrahydropyrido
[2,3-b]pyrazin-7-amine

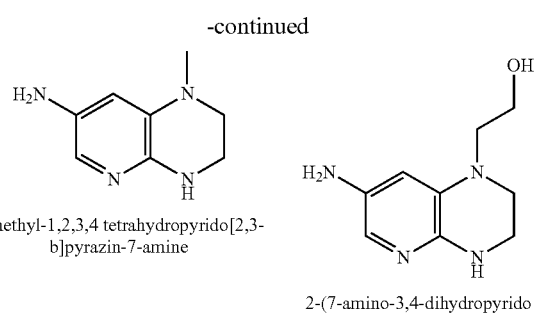

1-methyl-1,2,3,4 tetrahydropyrido[2,3-
b]pyrazin-7-amine 2-(7-amino-3,4-dihydropyrido
[2,3-b]pyrazin-1(2H)-yl)ethanol

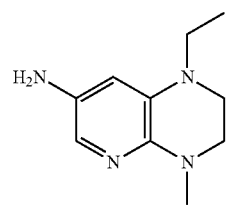

1-ethyl-4-methyl-1,2,3,4-
tetrahydropyrido[2,3-b]pyrazin-7-
amine

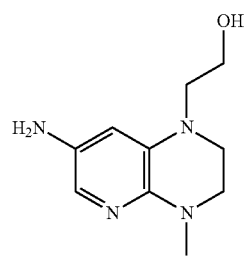

22-(7-amino-4-methyl-3,4-
dihydropyrido
[2,3-b]pyrazin-1(2H)-yl)ethanol

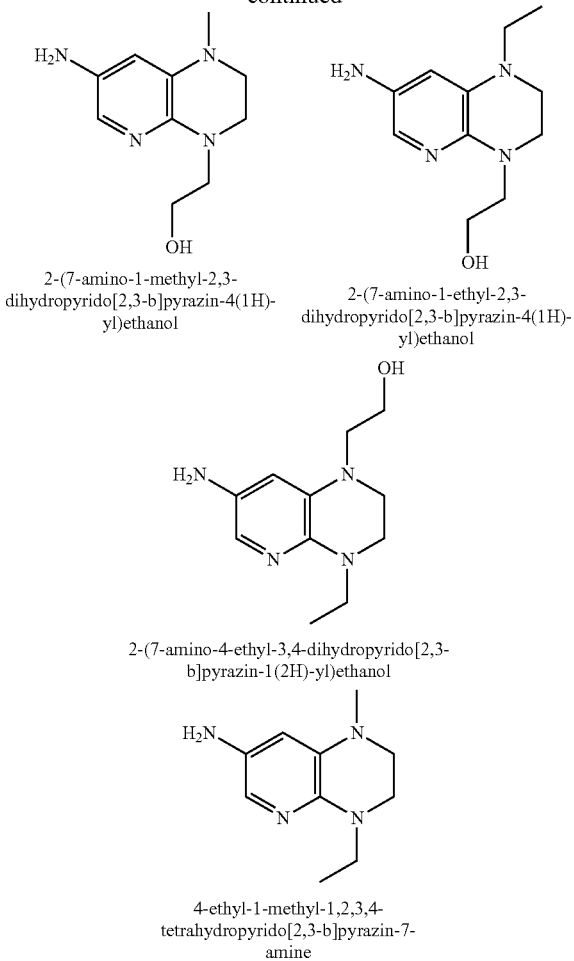

2-(7-amino-1-methyl-2,3-dihydropyrido[2,3-b]pyrazin-4(1H)-yl)ethanol 2-(7-amino-1-ethyl-2,3-dihydropyrido[2,3-b]pyrazin-4(1H)-yl)ethanol 2-(7-amino-4-ethyl-3,4-dihydropyrido[2,3-b]pyrazin-1(2H)-yl)ethanol 4-ethyl-1-methyl-1,2,3,4-tetrahydropyrido[2,3-b]pyrazin-7-amine and also the addition salts, optical isomers, geometrical isomers, tautomers and/or solvates thereof.

According to a particularly preferred embodiment, the 1,2,3,4-tetrahydropyrido[2,3-β]pyrazin-7-amine compounds according to the invention are chosen from the compounds of general formula (I), and also the addition salts, optical isomers, geometrical isomers, tautomers and/or solvates thereof:

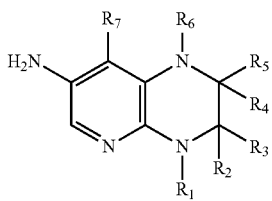

in which:

$R_2$, $R_3$, $R_4$, $R_5$ and $R_7$ are identical and represent a hydrogen atom, R1 and R6 are identical and represent a hydrogen atom or a C1-C6 alkyl radical, optionally terminating with at least one group —NX1X2 or an —OH radical, and X1 and X2 independently denote
a linear C1-C4 alkyl radical or a branched C3-C4 alkyl radical,
a linear C1-C4 hydroxyalkyl radical or a branched C3-C4 hydroxyalkyl radical, X1 and X2 possibly forming, with the nitrogen atom that bears them, a saturated or unsaturated 5- to 7-membered heterocycle, in which one of the ring members may be a heteroatom chosen from O, S and N; the said heterocycle possibly being substituted with one or more linear or branched $C_1$-$C_4$ alkyl or $C_1$-$C_4$ hydroxyalkyl radicals.

The saturated or unsaturated 5- to 7-membered heterocyclic radical in which one of the ring members may be a heteroatom chosen from O, S and N may be chosen from imidazole, piperazine, pyrrolidine, morpholine and piperidine rings.

Preferably, in this embodiment, R1 and R6 are identical and represent a C1-C6 alkyl radical, optionally terminating with an —OH radical.

Dye Composition

Another subject of the invention is a composition for dyeing keratin fibres comprising, in a suitable medium, at least one compound of formula (I) as defined above.

The compound of formula (I) may be present in the composition in an amount of between 0.001% and 10%, preferably between 0.005% and 6%, by weight approximately of the total weight of the dye composition.

The composition may also comprise at least one oxidation base. These bases may be chosen especially from para-phenylenediamines, bis(phenyl)alkylenediamines, para-aminophenols, ortho-aminophenols and heterocyclic bases, and the addition salts thereof.

Among the para-phenylenediamines, examples that may be mentioned more particularly include para-phenylenediamine, para-tolylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N,N-bis(β-hydroxyethyl)amino-2-methylaniline, 4-N,N-bis(β-hydroxyethyl)amino-2-chloroaniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N-ethyl-N-(β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-β-hydroxyethyloxy-para-phenylenediamine, 2-β-acetylaminoethyloxy-para-phenylenediamine, N-(β-methoxyethyl)-para-phenylenediamine, 4 aminophenylpyrrolidine, 2-thienyl-para-phenylenediamine, 2-β-hydroxyethylamino-5-aminotoluene, 3-hydroxy-1-(4'-aminophenyl)pyrrolidine, 6-(4-aminophenylamino)hexan-1-ol, N-(4-amino-3-methylphenyl)-N-[3-(1H-imidazol-1-yl)propyl]amine and N-(4-aminophenyl)-N-[3-(1H-imidazol-1-yl)propyl]amine, and the addition salts thereof with an acid.

Among the para-phenylenediamines mentioned above, para-phenylenediamine, para-tolylenediamine, 2-isopropyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloro-para-phenylenediamine, 2-β-acetylaminoethyloxy-paraphenylenediamine and 2-[{2-[(4-aminophenyl)amino]ethyl}(2-hydroxyethyl)amino]ethanol, and the addition salts thereof with an acid, are particularly preferred.

Among the bis(phenyl)alkylenediamines, examples that may be mentioned include N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)tetramethylenediamine, N,N'-bis(β-hydroxyethyl)-N,N'-bis(4-aminophenyl)tetramethylenediamine, N,N'-bis(4-methylaminophenyl)tetramethylenediamine, N,N'-bis(ethyl)-N,N'-bis(4'-amino-3'-methylphenyl)ethylenediamine and 1,8-bis(2,5-diaminophenoxy)-3,6-dioxaoctane, and the addition salts thereof with an acid.

Among the para-aminophenols, examples that may be mentioned include para-aminophenol, 4-amino-3-methylphenol, 4-amino-3-fluorophenol, 4-amino-2-chlorophenol, 4-amino-3-chlorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol, 4-amino-2-fluorophenol, 4-amino-2,6-dichlorophenol, 4-amino-6-[((5'-amino-2'-hydroxy-3'-methyl)phenyl)methyl]-2-methylphenol and bis[(5'-amino-2'-hydroxy)phenylmethane, and the addition salts thereof with an acid.

Among the ortho-aminophenols, examples that may be mentioned include 2-aminophenol, 2-amino-5-methylphenol, 2-amino-6-methylphenol and 5-acetamido-2-aminophenol, and the addition salts thereof with an acid.

Among the heterocyclic bases, examples that may be mentioned include pyridine derivatives, pyrimidine derivatives and pyrazole derivatives.

Among the pyridine derivatives, mention may be made of the compounds described, for example, in patents GB 1 026 978 and GB 1 153 196, such as 2,5-diaminopyridine, 2-(4-methoxyphenyl)amino-3-aminopyridine, 3,4-diaminopyridine, and the addition salts thereof with an acid.

Other pyridine oxidation bases that are useful in the present invention are the 3-aminopyrazolo[1,5-a]pyridine oxidation bases or the addition salts thereof, described, for example, in patent application FR 2 801 308. Examples that may be mentioned include pyrazolo[1,5-a]pyrid-3-ylamine, 2-acetylaminopyrazolo[1,5-a]pyrid-3-ylamine, 2-(morpholin-4-yl)pyrazolo[1,5-a]pyrid-3-ylamine, 3-aminopyrazolo[1,5-a]pyridine-2-carboxylic acid, 2-methoxypyrazolo[1,5-a]pyrid-3-ylamine, (3-aminopyrazolo[1,5-a]pyrid-7-yl)methanol, 2-(3-aminopyrazolo[1,5-a]pyrid-5-yl)ethanol, 2-(3-aminopyrazolo[1,5-a]pyrid-7-yl)ethanol, (3-aminopyrazolo[1,5-a]pyrid-2-yl)methanol, 3,6-diaminopyrazolo[1,5-a]pyridine, 3,4-diaminopyrazolo[1,5-a]pyridine, pyrazolo[1,5-a]pyridine-3,7-diamine, 7-(morpholin-4-yl)pyrazolo[1,5-a]pyrid-3-ylamine, pyrazolo[1,5-a]pyridine-3,5-diamine, 5-(morpholin-4-yl)pyrazolo[1,5-a]pyrid-3-ylamine, 2-[(3-aminopyrazolo[1,5-a]pyrid-5-yl)(2-hydroxyethyl)amino]ethanol, 2-[(3-aminopyrazolo[1,5-a]pyrid-7-yl)(2-hydroxyethyl)amino]ethanol, 3-aminopyrazolo[1,5-a]pyridin-5-ol, 3-aminopyrazolo[1,5-a]pyridin-4-ol, 3-aminopyrazolo[1,5-a]pyridin-6-ol and 3-aminopyrazolo[1,5-a]pyridin-7-ol, and addition salts thereof with an acid.

Among the pyridine bases that are of use in the present invention, mention may also be made of the compounds described in patent applications EP 1792903 and EP 1792606 and the addition salts thereof.

Among the pyrimidine derivatives, mention may be made of the compounds described, for example, in patents DE 2359399, JP 88169571, JP 05-63124 and EP 0 770 375 or patent application WO 96/15765, such as 2,4,5,6-tetraaminopyrimidine, 4-hydroxy-2,5,6-triaminopyrimidine, 2-hydroxy-4,5,6-triaminopyrimidine, 2,4-dihydroxy-5,6-diaminopyrimidine, 2,5,6-triaminopyrimidine and the addition salts thereof, and the tautomeric forms thereof, when a tautomeric equilibrium exists.

Among the pyrazolopyrimidine derivatives, mention may be made of the compounds described, for example, in patent applications EP 0847271, EP 0926149 and EP 1147109 and the addition salts thereof.

Among the pyrazole derivatives, mention may be made of the compounds described in patents DE 3843892, DE 4133957 and patent applications WO 94/08969, WO 94/08970, FR-A-2 733 749 and DE 195 43 988, such as 4,5-diamino-1-methylpyrazole, 4,5-diamino-1-(β-hydroxyethyl)pyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl)amino-1,3-dimethylpyrazole, 3,4,5-triamino-pyrazole, 1-methyl-3,4,5-triaminopyrazole, 3,5-diamino-1-methyl-4-methylaminopyrazole, 3,5-diamino-4-(β-hydroxyethyl)amino-1-methylpyrazole, and the addition salts thereof.

As oxidation bases, mention may also be made of the diamino-N,N-dihydropyrazolone derivatives of formula (III) or an addition salt or solvate thereof:

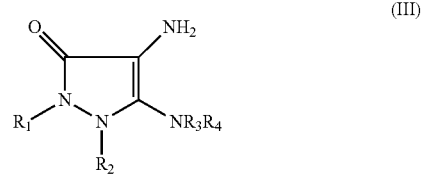

(III)

in which:

R$_1$, R$_2$, R$_3$ and R$_4$, which may be identical or different, represent:
  a linear or branched C$_1$-C$_6$ alkyl radical optionally substituted with one or more radicals chosen from the group consisting of a radical OR$_5$, a radical NR$_6$R$_7$, a carboxyl radical, a sulfonic radical, a carboxamido radical CONR$_6$R$_7$, a sulfonamido radical SO$_2$NR$_6$R$_7$, a heteroaryl, an aryl optionally substituted with a (C$_1$-C$_4$)alkyl, hydroxyl, C$_1$-C$_2$ alkoxy, amino or (di)alkyl (C$_1$-C$_2$)amino group;
  an aryl radical optionally substituted with one or more (C$_1$-C$_4$)alkyl, hydroxyl, C$_1$-C$_2$ alkoxy, amino or (di)alkyl(C$_1$-C$_2$)amino;
  a 5- or 6-membered heteroaryl radical, optionally substituted with one or more radicals chosen from (C$_1$-C$_4$) alkyl and (C$_1$-C$_2$)alkoxy;

R$_3$ and R$_4$ may also represent a hydrogen atom;

R$_5$, R$_6$ and R$_7$, which may be identical or different, represent a hydrogen atom; a linear or branched C$_1$-C$_4$ alkyl radical optionally substituted with one or more radicals chosen from the group consisting of a hydroxyl, a C$_1$-C$_2$ alkoxy, a carboxamido CONR$_8$R$_9$, a sulfonyl SO$_2$R$_8$, an aryl optionally substituted with a $(C_1-C_4)$alkyl, a hydroxyl, a $C_1-C_2$ alkoxy, an amino or a (di)$(C_1-C_2)$alkylamino; an aryl optionally substituted with a $(C_1-C_4)$alkyl, a hydroxyl, a $C_1-C_2$ alkoxy, an amino or a (di)$(C_1-C_2)$alkylamino;

$R_6$ and $R_7$, which may be identical or different, may also represent a carboxamido radical $CONR_8R_9$; a sulfonyl radical $SO_2R_8$;

$R_8$ and $R_9$, which may be identical or different, represent a hydrogen atom; a linear or branched $C_1-C_4$ alkyl radical optionally substituted with one or more hydroxyl or $C_1-C_2$ alkoxy;

$R_1$ and $R_2$, on the one hand, and $R_3$ and $R_4$, on the other hand, may form, with the nitrogen atoms to which they are attached, a saturated or unsaturated 5- to 7-membered heterocycle optionally substituted with one or more radicals chosen from the group consisting of halogen atoms and amino, (di)alkyl$(C_1-C_4)$amino, hydroxyl, carboxyl, carboxamido and $(C_1-C_2)$alkoxy radicals, $C_1-C_4$ alkyl radicals optionally substituted with one or more hydroxyl, amino, (di)alkylamino, alkoxy, carboxyl or sulfonyl radicals;

$R_3$ and $R_4$ may also form, together with the nitrogen atom to which they are attached, a 5- or 7-membered heterocycle, the carbon atoms of which may be replaced with an optionally substituted oxygen or nitrogen atom.

These diamino-N,N-dihydropyrazolone derivatives are more particularly described in patent application FR 2866338, a particularly preferred derivative being 2,3-diamino-6,7-dihydro-1H,5H-pyrazolo[1,2-a]pyrazol-1-one dimethanesulfonate.

Oxidation bases that may also be mentioned include the diamino-N,N-dihydropyrazolone derivatives of formula (IV) or an addition salt or solvate thereof:

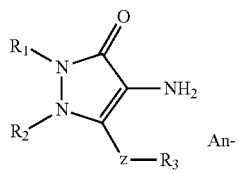

(IV)

in which:
z represents independently:
a single covalent bond,
a divalent radical chosen from
an oxygen atom,
a radical —$NR_6$, with $R_6$ representing a hydrogen atom or a $C_1-C_6$ alkyl radical, or $R_6$, with $R_3$, forming, together with the nitrogen atom to which they are attached, a substituted or unsubstituted, saturated or unsaturated, aromatic or non-aromatic, 5- to 8-membered heterocycle, optionally containing one or more other heteroatoms or groups chosen from N, O, S, $SO_2$ and —CO—, it being possible for the heterocycle to be cationic and/or substituted with a cationic radical,
a radical —$N+R_7R_8$— with $R_7$ and $R_8$ independently representing an alkyl radical; the alkyl radical may be substituted with an OH or an —Oalkyl,
$R_3$ represents:
a hydrogen,
a $C_1-C_{10}$ alkyl radical, which is optionally substituted, the alkyl radical possibly being interrupted with a heteroatom or a group chosen from O, N, Si, S, SO and $SO_2$,
a $C_1-C_{10}$ alkyl radical substituted and/or interrupted with a cationic radical,
a halogen,
an $SO_3H$ radical,
a substituted or unsubstituted, saturated, unsaturated or aromatic, 5- to 8-membered ring, optionally containing one or more heteroatoms or groups chosen from N, O, S, $SO_2$ and —CO—, it being possible for the ring to be cationic and/or substituted with a cationic radical, $R_1$ and $R_2$, which may be identical or different, represent:
a linear or branched $C_1-C_6$ alkyl radical optionally substituted with one or more radicals chosen from a radical $OR_5$, a radical $NR_9R_{10}$, a carboxyl radical, a sulfonic radical, a carboxamido radical $CONR_9R_{10}$, a sulfonamido radical $SO_2NR_9R_{10}$, a heteroaryl, an aryl optionally substituted with a $(C_1-C_4)$alkyl, hydroxyl, $C_1-C_2$ alkoxy, amino or (di)alkyl$(C_1-C_2)$amino group;
an aryl radical optionally substituted with one or more $(C_1-C_4)$alkyl, hydroxyl, $C_1-C_2$ alkoxy, amino or (di)alkyl$(C_1-C_2)$amino;
a 5- or 6-membered heteroaryl radical, optionally substituted with one or more radicals chosen from $(C_1-C_4)$ alkyl monosubstituted or polysubstituted with an OH or an —Oalkyl or $(C_1-C_2)$alkoxy;

$R_1$ and $R_2$ may form, with the nitrogen atoms to which they are attached, a saturated or unsaturated 5- to 7-membered heterocycle optionally substituted with one or more radicals chosen from the group consisting of halogen atoms and amino, (di)alkyl$(C_1-C_4)$amino, hydroxyl, carboxyl, carboxamido and $(C_1-C_2)$alkoxy radicals, $C_1-C_4$ alkyl radicals optionally substituted with one or more hydroxyl, amino, (di)alkylamino, alkoxy, carboxyl or sulfonyl radicals;

An—represents an anion or a group of anions that ensures the electrical neutrality of the compounds of formula (V),
on the condition that at least one of the groups Z and $R_3$ represents a cationic radical.

These derivatives of diamino-N,N-dihydropyrazolone are described in patent application FR 2 927 078.

In general, the concentration of the oxidation base(s) ranges from 0.0001% to 20% and preferably from 0.005% to 6% by weight relative to the total weight of the composition.

Couplers

The dye composition according to the invention may contain and preferably contains one or more additional oxidation couplers, other than the compounds of general formula (I), that are conventionally used for dyeing keratin fibres. Among these couplers, mention may be made especially of meta-phenylenediamines, meta-aminophenols, meta-diphenols, naphthalene couplers and heterocyclic couplers, and the addition salts thereof.

Examples of additional couplers that may be mentioned include 2-methyl-5-aminophenol, 5-N-(β-hydroxyethyl) amino-2-methylphenol, 6-chloro-2-methyl-5-aminophenol, 3-aminophenol, 2,4-dichloro-3-aminophenol, 5-amino-4-chloro-o-cresol, 1,3-dihydroxybenzene, 1,3-dihydroxy-2-methylbenzene, 4-chloro-1,3-dihydroxybenzene, 2,4-diamino-1-(β-hydroxyethyloxy)benzene, 2-amino-4-(β-hydroxyethylamino)-1-methoxybenzene, 1,3-diaminobenzene, 1,3-bis(2,4-diaminophenoxy)propane, 3-ureidoaniline, 3-ureido-1-dimethylaminobenzene, sesamol, 1-β-hydroxyethylamino-3,4-methylenedioxybenzene, α-naphthol, 2-methyl-1-naphthol, 1,5-dihydroxynaphthalene, 2,7-naphthalenediol, 1-acetoxy-2-methylnaphthalene, 6-hydroxyindole, 4-hydroxyindole, 4-hydroxy-N-methylindole, 2-amino-3-hydroxypyridine, 6-hydroxybenzomorpholine, 3,5-diamino-2,6-dimethoxypyridine, 2,6-dihydroxy-3-4-dimethylpyridine, 3-amino-2-methylamino-6-methoxypyridine, 1-N-(β-hydroxyethyl)amino-3,4- methylenedioxybenzene, 2,6-bis(β-hydroxyethylamino) toluene and 3-methyl-1-phenyl-5-pyrazolone and the addition salts thereof with an acid.

In the dye composition of the present invention, the additional coupler(s), if they are present, generally represent an amount of between 0.001% and 10% by weight approximately and preferably between 0.005% and 6% by weight of the total weight of the composition.

The dye composition in accordance with the invention may also contain one or more direct dyes that may in particular be chosen from nitrobenzene dyes, azo direct dyes and methine direct dyes. These direct dyes may be of nonionic, anionic or cationic nature.

The medium that is suitable for dyeing, also known as the dye support, generally comprises water or a mixture of water and of one or more solvents, for instance $C_1$-$C_4$ lower alkanols such as ethanol and isopropanol, polyols, for instance propylene glycol, dipropylene glycol or glycerol, and polyol ethers, for instance dipropylene glycol monomethyl ether.

The solvent(s) are generally present in proportions that may be between 1% and 40% by weight approximately and more preferably between 3% and 30% by weight approximately relative to the total weight of the dye composition.

The dye composition in accordance with the invention may also contain various adjuvants conventionally used in hair dye compositions, such as anionic, cationic, nonionic, amphoteric or zwitterionic surfactants or mixtures thereof, anionic, cationic, nonionic, amphoteric or zwitterionic polymers or mixtures thereof, mineral or organic thickeners, and in particular anionic, cationic, nonionic and amphoteric polymeric associative thickeners, antioxidants, penetrants, sequestrants, fragrances, buffers, dispersants, conditioning agents, for instance volatile or non-volatile, modified or unmodified silicones, film-forming agents, ceramides, preserving agents and opacifiers.

The above adjuvants are generally present in an amount for each of them of between 0.01% and 20% by weight relative to the weight of the composition.

Needless to say, a person skilled in the art will take care to select this or these optional additional compound(s) such that the advantageous properties intrinsically associated with the oxidation dye composition in accordance with the invention are not, or are not substantially, adversely affected by the envisaged addition(s).

The pH of the dye composition in accordance with the invention is generally between 3 and 12 approximately and preferably between 5 and 11 approximately. It may be adjusted to the desired value by means of acidifying or basifying agents customarily used in the dyeing of keratin fibres, or alternatively using standard buffer systems.

Among the acidifying agents, examples that may be mentioned include mineral or organic acids, for instance hydrochloric acid, orthophosphoric acid, sulfuric acid, carboxylic acids, for instance acetic acid, tartaric acid, citric acid and lactic acid, and sulfonic acids.

Among the basifying agents, examples that may be mentioned include aqueous ammonia, alkali metal carbonates, alkanolamines such as monoethanolamine, diethanolamine and triethanolamine, and also derivatives thereof, sodium hydroxide, potassium hydroxide and the compounds of formula (III) below:

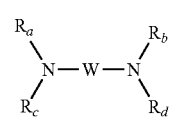

(III)

in which W is a propylene residue optionally substituted with a hydroxyl group or a $C_1$-$C_4$ alkyl radical; $R_a$, $R_b$, $R_c$ and $R_d$, which may be identical or different, represent a hydrogen atom or a $C_1$-$C_4$ alkyl or $C_1$-$C_4$ hydroxyalkyl radical.

The composition according to the invention may comprise one or more oxidizing agents.

The oxidizing agents are those conventionally used for the oxidation dyeing of keratin fibres, for example hydrogen peroxide, urea peroxide, alkali metal bromates, persalts such as perborates and persulfates, peracids and oxidase enzymes, among which mention may be made of peroxidases, 2-electron oxidoreductases such as uricases, and 4-electron oxygenases, for instance laccases. Hydrogen peroxide is particularly preferred.

The dye composition with or without oxidizing agent according to the invention may be in various forms, such as in the form of liquids, creams or gels, or in any other form that is suitable for dyeing keratin fibres, and especially human hair.

It may result from the mixing, at the time of use, of several compositions.

In particular, it results from the mixing of at least two compositions, one comprising at least one compound of formula (I), optionally one or more additional oxidation bases, and optionally one or more additional couplers other than the compounds of formula (I), or salts thereof, and a second composition comprising one or more oxidizing agents as described previously.

The composition of the invention is thus applied to the hair for the dyeing of keratin fibres, either as is or in the presence of one or more oxidizing agents for the dyeing of keratin fibres.

The process of the present invention is a process in which the composition according to the present invention as defined previously is applied to the fibres, either alone or in the presence of an oxidizing agent, for a time that is sufficient to develop the desired colouring. The colour may be developed at acidic, neutral or alkaline pH, and the oxidizing agent may be added to the composition of the invention just at the time of use, or it may be used starting from an oxidizing composition which comprises it and which is applied simultaneously with or sequentially to the composition of the invention.

According to a particular embodiment, the composition is free of oxidizing agent and is mixed, preferably at the time of use, with a composition containing, in a medium that is suitable for dyeing, one or more oxidizing agents, these oxidizing agents being present in an amount sufficient to develop a colouring. The mixture obtained is then applied to the keratin fibres. After a leave-in time of approximately 3 to 50 minutes, preferably approximately 5 to 30 minutes, the keratin fibres are rinsed, washed with shampoo, rinsed again and then dried.

The oxidizing agents are those indicated above.

The oxidizing composition may also contain various adjuvants conventionally used in compositions for dyeing the hair and as defined above.

The pH of the oxidizing composition containing the oxidizing agent is such that, after mixing with the dye composition, the pH of the resulting composition applied to the keratin fibres preferably varies between 3 and 12 approximately and more preferably still between 5 and 11. It may be adjusted to the desired value by means of acidifying or basifying agents usually used in the dyeing of keratin fibres and as defined previously.

The ready-to-use composition that is finally applied to the keratin fibres may be in various forms, such as in the form of liquids, creams or gels or in any other form that is suitable for dyeing keratin fibres, and especially human hair.

Another subject of the invention is a dyeing "kit" or multi-compartment device in which a first compartment contains the dye composition devoid of oxidizing agent of the present invention defined above, comprising one or more oxidation bases chosen from the compound of formula (I) or the addition salts thereof with an acid, and a second compartment contains one or more oxidizing agents.

These devices may be equipped with a means for dispensing the desired mixture on the hair, such as the devices described in patent FR-2 586 913 in the name of the Applicant.

Preparation of the Compound of Formula (I)

The synthesis of the compounds of formula (I) may be performed, for example, according to the following procedures:

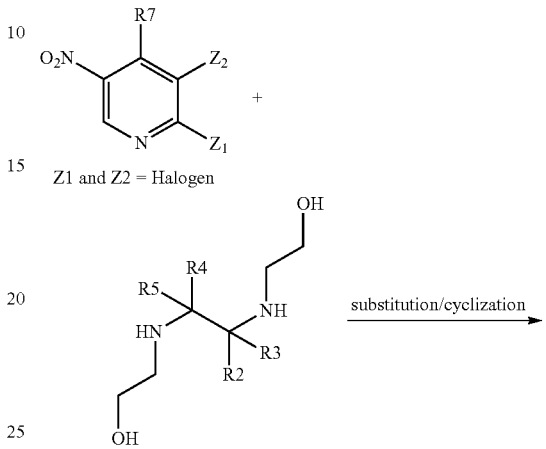

By way of example, when $R_1$ and/or $R_6$ represents a $C_1$-$C_{10}$ alkyl radical interrupted with one or more heteroatoms chosen from S or O or NR and optionally terminating with at least one group NX1X2 or OX3, then the synthetic process used may be as follows:

in a first stage:

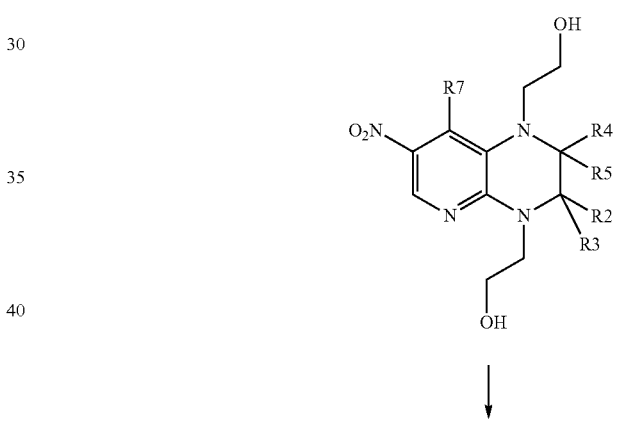

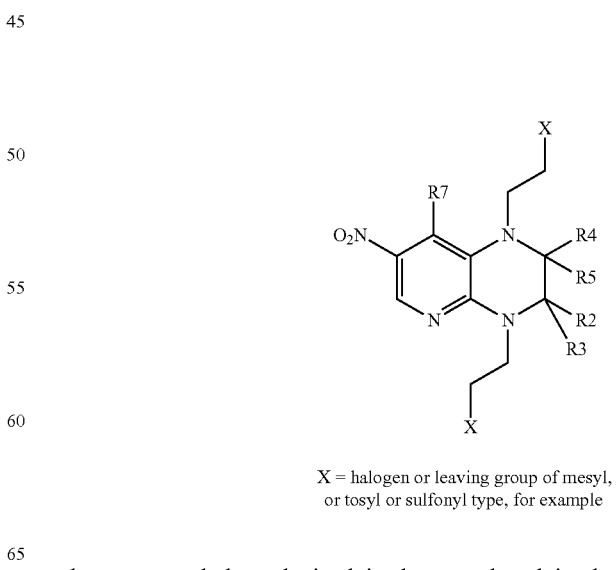

X = halogen or leaving group of mesyl, or tosyl or sulfonyl type, for example the compound thus obtained is then employed in the following reaction scheme:

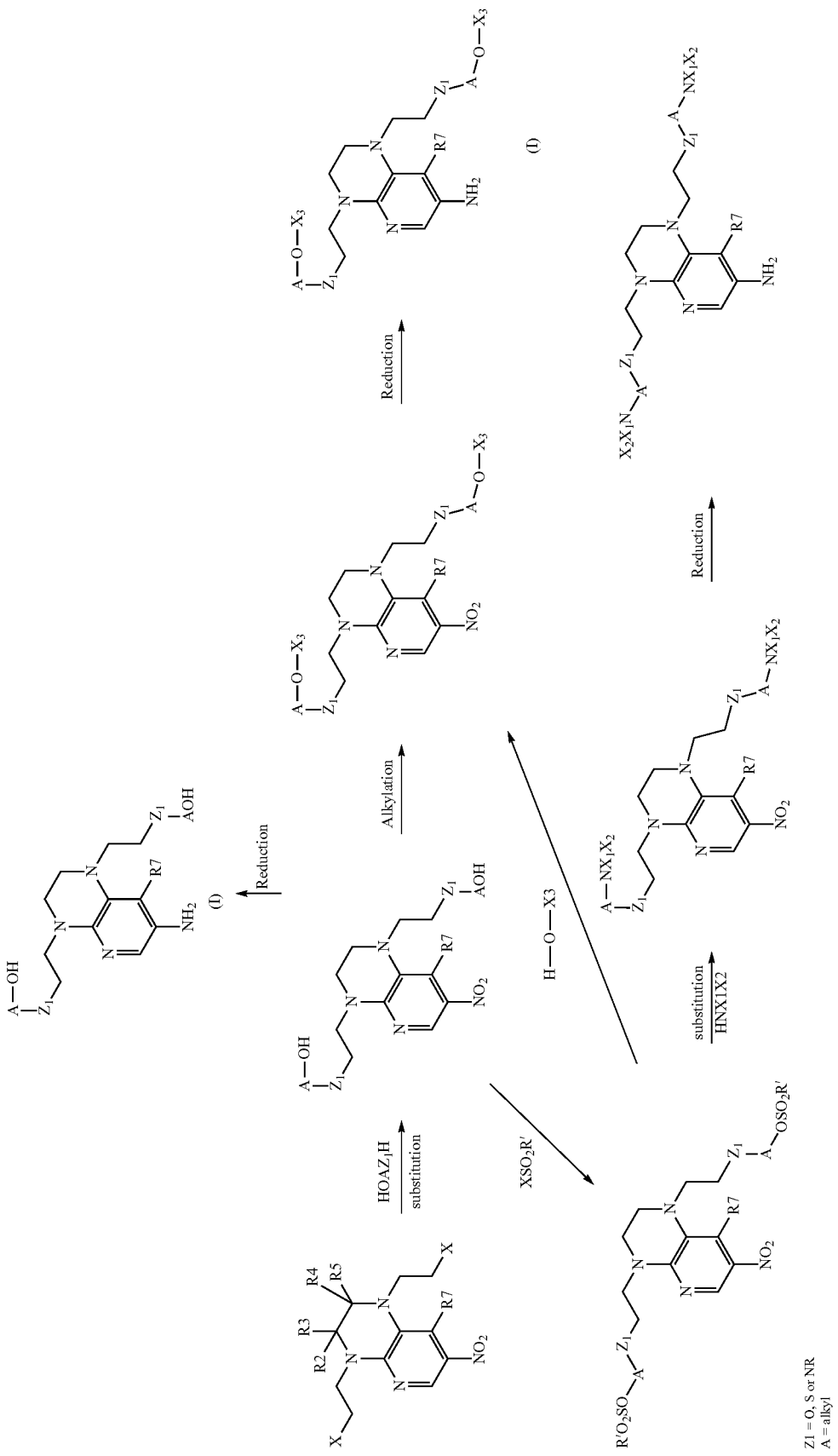

The substitution reaction is performed in a dipolar solvent such as acetonitrile, THF or in DMF or NMP, or in an alcohol such as ethanol, for example, in the presence of a base such as triethylamine, ethyldiisopropylamine, sodium hydroxide or potassium hydroxide, for example, and one or more equivalents of HOZ1 H for 1 to 24 hours at a temperature from 20° C. to the reflux temperature of the solvent.

At this stage, the compound obtained is reduced or the hydroxyl function thus introduced is then substituted with a halide (for example mesyl or tosyl halide) in a solvent such as acetonitrile or THF or in an alcohol such as ethanol, for example, in the presence of a base such as triethylamine, ethyldiisopropylamine, sodium hydroxide or potassium hydroxide, for example, for 1 to 24 hours at a temperature from 20° C. to the reflux temperature of the solvent.

The substitution of the leaving group introduced in the preceding step is performed either by reaction with an amine HNX1X2 or an alcohol HOX3 in a solvent such as THF or acetonitrile or dioxane or ethyl acetate, for 15 minutes to 24 hours at a temperature ranging from 15° C. to the reflux temperature of the solvent.

The reduction of the nitro group is performed under standard conditions, for example by performing a hydrogenation reaction under heterogeneous catalysis in the presence of Pd/C, Pd(II)/C, Ni/Ra, etc., or alternatively by performing a reduction reaction with a metal, for example with zinc, iron, tin, etc. (see *Advanced Organic Chemistry*, 3rd Edition, J. March, 1985, Wiley Interscience and *Reduction in Organic Chemistry*, M. Hudlicky, 1983, Ellis Horwood Series Chemical Science).

The examples which follow serve to illustrate the invention without, however, exhibiting a limiting nature.

EXAMPLES

Examples of Synthesis

Example 1: Synthesis of 1,4-dimethyl-1,2,3,4-tetrahydropyrido[2,3-b]pyrazin-7-amine dihydrochloride

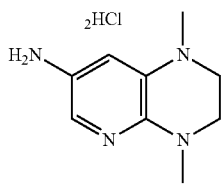

Synthesis of 1,4-dimethyl-7-nitro-1,2,3,4-tetrahydropyrido[2,3-b]pyrazine

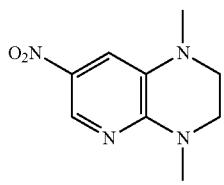

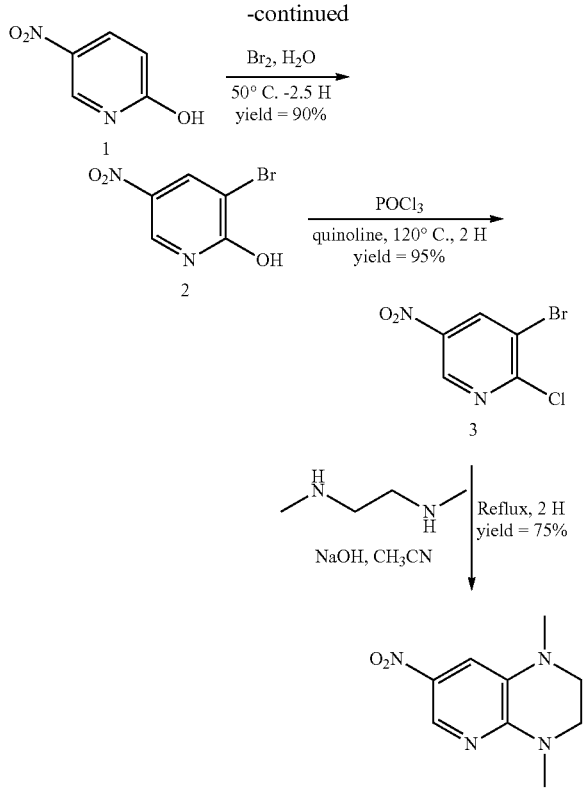

First Step

A solution of bromine (2.1 ml, 39.3 mmol) was added dropwise to a solution of compound 1 (5 g, 35.8 mmol) in 700 ml of water. The reaction medium was stirred at 5° C. for 2.5 hours and then maintained at room temperature.

The resulting precipitate was collected by filtration, washed with water and dried to give compound 2 (yellow solid, 7.25 g, yield: 93%).

The NMR analyses ($^1$H 400 MHz DMSO-$d_6$) are in accordance with the expected structure.

Second Step

POCl3 (3 ml) was added at 0° C. to the mixture of compound 2 (7.25 g, 33 mmol) and quinoline (2 ml, 16.5 mmol). This reaction medium was heated at 120° C. for 2.5 hours and then, after cooling to room temperature, 20 ml of water were added. The precipitate formed was collected by filtration and dried to give the expected compound 3 in the form of a brown solid, in a yield of 95% (7.5 g).

The NMR analyses ($^1$H 400 MHz DMSO-$d_6$) are in accordance with the expected structure.

Third Step

A solution of compound 3 (7.11 g, 30 mmol) in MeCN (200 ml) was added dropwise to a suspension of N,N-dimethylenediamine (5.28 g, 60 mmol) and NaHCO$_3$ (10.08 g, 120 mmol) in MeCN (500 ml).

The mixture was stirred at reflux for 2 hours. After cooling to room temperature, the mixture was evaporated under reduced pressure and the residue was then dissolved in 300 ml of 1N HCl.

The mixture was filtered and the filtrate was adjusted to pH ~10 by adding sodium hydroxide solution. The precipitate obtained was collected by filtration to give the expected product in the form of an orange-coloured solid (4.8 g), in a yield of 77%.

The NMR analyses (¹H 400 MHz DMSO-d₆) are in accordance with the expected structure.

Analysis by mass spectrometry confirms the structure of the expected compound C9H12N4O2. The quasi-molecular ions [M+H]+, [M+Na]+, [M−H]− of the expected molecule are mainly detected.

Synthesis of 1,4-dimethyl-1,2,3,4-tetrahydropyrido[2,3-b]pyrazin-7-amine dihydrochloride

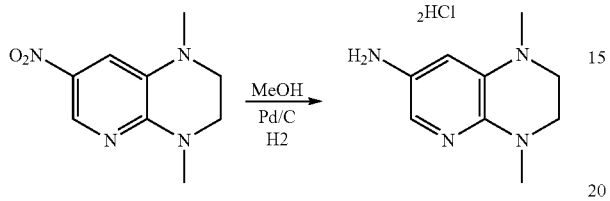

100 ml of ethanol, 1.6 g (0.0772 mol) of 1,4-dimethyl-7-nitro-1,2,3,4-tetrahydropyrido[2,3-b]pyrazine, 10 ml of cyclohexene and 500 mg of palladium-on-charcoal are placed in a 250 ml three-necked flask equipped with a condenser, a thermometer and a bubbler.

This reaction medium is refluxed for 3 hours.

The heating is stopped and the reaction medium is then filtered on a sinter funnel packed with Celite over a vacuum flask containing 50 ml of 6.0N hydrochloric isopropanol. The Celite is washed with 50 ml of ethanol and the beige-coloured precipitate formed in the filtrate is in turn filtered off on a sinter funnel under an argon atmosphere and washed with 25 ml of isopropanol and then 2×25 ml of diisopropyl ether. The beige-coloured solid thus obtained is then placed in a desiccator (P₂O₅, vacuum, 45° C.) to constant weight. The expected compound is isolated in the form of a pale beige-violet powder in a mass of 108 mg, corresponding to the expected compound.

The NMR analyses (¹H 400 MHz DMSO-d₆) are in accordance with the expected structure.

Analysis by mass spectrometry confirms the structure of the expected compound C9H14N4. The quasi-molecular ions [M+H]+, [M+Na]+, [M−H]− of the expected molecule are mainly detected.

Example 2: Synthesis of 2,2'-(7-amino-2,3-dihydropyrido[2,3-b]pyrazine-1,4-diyl)diethanol dihydrochloride

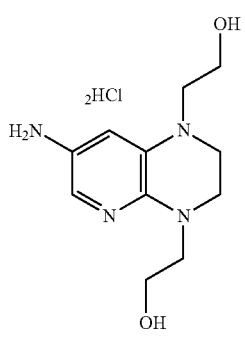 [SMILES: Nc1cnc2c(c1)N(CCO)CCN2CCO]

First Step

Synthesis of 2,2'-(7-nitro-2,3-dihydropyrido[2,3-b]pyrazine-1,4-diyl)diethanol

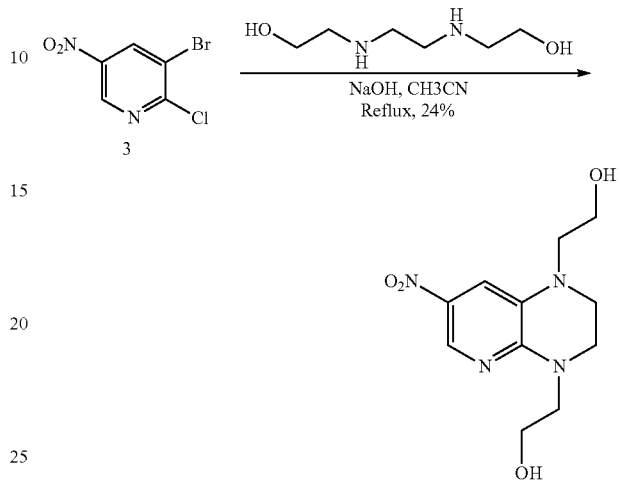

8.88 g (60 mmol) of N,N'-bis(2-hydroxyethyl)ethylenediamine and 10.08 g (120 mmol) of NaHCO₃ were placed in 500 ml of MeCN, followed by dropwise addition of a solution of 2-chloro-3-bromo-5-nitropyridine (7.11 g, 30 mmol) in 200 ml of MeCN.

The mixture was refluxed for 24 hours and then cooled to room temperature and filtered. The filtrate was evaporated under reduced pressure and the residue obtained was purified by chromatography on a column of silica gel (eluent: ethyl acetate/petroleum ether=5/1) to give the expected compound in the form of an orange solid (1.7 g; 20% yield).

The NMR analyses (¹H 400 MHz DMSO-d₆) are in accordance with the expected structure.

Analysis by mass spectrometry confirms the structure of the expected compound C11H16N4O4. The quasi-molecular ions [M+H]+, [M+Na]+, [M−H]− of the expected molecule are mainly detected.

Second Step 2,2-(7-Amino-2,3-dihydropyrido[2,3-b]pyrazine-1,4-diethanol dihydrochloride

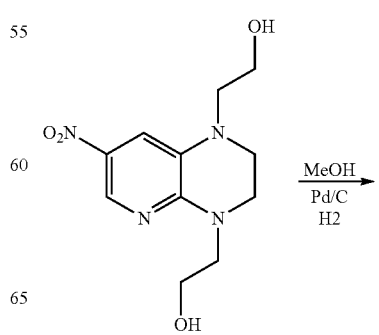

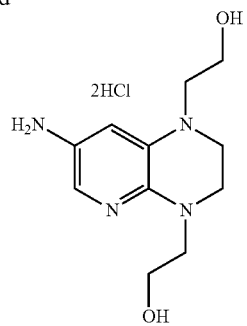

This reduction is performed using an H-Cube hydrogenator containing a 90×4 mm cartridge of 10% Pd/C.

A solution of 2.10 g (0.0155 mol) of 2,2'-(7-nitro-2,3-dihydropyrido[2,3-b]pyrazine-1,4-diyl)diethanol in 155 ml of ethanol is introduced at a flow rate of 1 ml per minute onto a cartridge of palladium catalyst at 80° C. under a pressure of 50 bar in the H-Cube system in the presence of hydrogen.

At the machine outlet, the product solution is recovered in a solution of 50 ml of 6N hydrochloric isopropanol. The medium is concentrated and then taken up in 200 ml of isopropanol, concentrated again and then taken up in 200 ml of isopropanol until a precipitate appears.

This mixture is then cooled to 0° C. for 30 minutes and the precipitate formed is then isolated by filtration on a sinter funnel washed with a minimum amount of isopropanol and then with 2×100 ml of diisopropyl ether, filtered off by suction under argon and then placed in a desiccator ($P_2O_5$, vacuum, 45° C.) to constant weight. 0.620 g (28.5% yield) of the expected compound is thus isolated in the form of a grey powder.

The NMR analyses ($^1$H 400 MHz DMSO-$d_6$) are in accordance with the expected structure.

Analysis by mass spectrometry confirms the structure of the expected compound C11H18N4O2. The quasi-molecular ions [M+H]+, [M+Na]+, [M−H]− of the expected molecule are mainly detected.

Examples of Dyeing

Example 1

The following dye compositions were prepared:

| | Example 1 | | | |
|---|---|---|---|---|
| 2,2'-(7-Amino-2,3-dihydropyrido[2,3-b]pyrazine-1,4-diyl)diethanol dihydrochloride | $10^{-3}$ mol | $10^{-3}$ mol | $10^{-3}$ mol | $10^{-3}$ mol |
| 4-Aminophenylamine dihydrochloride | $10^{-3}$ mol | | | |
| 4-Aminophenol | | $10^{-3}$ mol | | |
| 4-Amino-2-[(2-hydroxyethoxy)methyl]phenol hydrochloride | | | $10^{-3}$ mol | |
| 2,3-Diamino-6,7-dihydro-1H,5H-pyrazolo[1,2-a]pyrazol-1-one dimethanesulfonate | | | | $10^{-3}$ mol |
| Dye support (1) | (*) | (*) | (*) | (*) |
| Demineralized water qs | 100 g | 100 g | 100 g | 100 g |
| Shade observed | Strong dark grey | Bright orange-red | Bright orange-red | Bright chromatic coppery red |

| | Example 2 | | | |
|---|---|---|---|---|
| 1,4-Dimethyl-1,2,3,4-tetrahydropyrido[2,3-b]pyrazin-7-amine dihydrochloride | $10^{-3}$ mol | $10^{-3}$ mol | $10^{-3}$ mol | $10^{-3}$ mol |
| 4-Aminophenylamine dihydrochloride | $10^{-3}$ mol | | | |
| 4-Aminophenol | | $10^{-3}$ mol | | |
| 4-Amino-2-[(2-hydroxyethoxy)methyl]phenol hydrochloride | | | $10^{-3}$ mol | |
| 2,3-Diamino-6,7-dihydro-1H,5H-pyrazolo[1,2-a]pyrazol-1-one dimethanesulfonate | | | | $10^{-3}$ mol |
| Dye support (1) | (*) | (*) | (*) | (*) |
| Demineralized water qs | 100 g | 100 g | 100 g | 100 g |
| Shade observed | Very strong dark grey | Bright red | Bright orange-red | Bright chromatic coppery red |

(*): dye support (1) pH 9.5
96° ethyl alcohol 20.8 g
35% aqueous sodium metabisulfite solution 0.23 g AM

| | |
|---|---|
| Pentasodium salt of diethylenetriaminepentaacetic acid as an aqueous 40% solution | 0.48 g AM |
| C8-C10 alkyl polyglucoside as an aqueous 60% solution | 3.6 g AM |
| Benzyl alcohol | 2.0 g |
| Polyethylene glycol containing 8 units of ethylene oxide | 3.0 g |
| NH$_4$Cl | 4.32 g |
| Aqueous ammonia containing 20% NH$_3$ | 2.94 g |

At the time of use, each composition is mixed with an equal weight of 20-volumes aqueous hydrogen peroxide solution (6% by weight). A final pH of 9.5 is obtained.

Each mixture obtained is applied to locks of grey hair containing 90% white hairs. After a leave-in time of 30 minutes, the locks are rinsed, washed with a standard shampoo, rinsed again and then dried, to give the shades mentioned.

Example 2

The following dye compositions were prepared

| | Composition according to the invention | | | |
|---|---|---|---|---|
| | A1 | A2 | A3 | A4 |
| 2,2'-(7-Amino-2,3-dihydropyrido[2,3-b]pyrazine-1,4-diyl)diethanol dihydrochloride | 10$^{-3}$ mol | 10$^{-3}$ mol | 10$^{-3}$ mol | 10$^{-3}$ mol |
| 4-Aminophenol | 10$^{-3}$ mol | | | |
| Paraphenylene diamine | | 10$^{-3}$ mol | | |
| 2,3-Diamino-6,7-dihydro-1H,5H-pyrazolo[1,2-a]pyrazol-1-one dimethanesulfonate | | | 10$^{-3}$ mol | |
| 2-[(3-aminopyrazolo[1,5-a]pyridin-2-yl)oxy]ethanol hydrochloride | | | | 10$^{-3}$ mol |
| Dye support (1) | (*) | (*) | (*) | (*) |
| Demineralized water qs | 100 g | 100 g | 100 g | 100 g |

| | Composition | | | |
|---|---|---|---|---|
| | B1 | B2 | B3 | B4 |
| 1,4-dimethyl-1,2,3,4-tetrahydropyrido[2,3-b]pyrazin-7-amine hydrochloride | 10$^{-3}$ mol | 10$^{-3}$ mol | 10$^{-3}$ mol | 10$^{-3}$ mol |
| 4-Aminophenol | 10$^{-3}$ mol | | | |
| Paraphenylene diamine | | 10$^{-3}$ mol | | |
| 2,3-Diamino-6,7-dihydro-1H,5H-pyrazolo[1,2-a]pyrazol-1-one dimethanesulfonate | | | 10$^{-3}$ mol | |
| 2-[(3-aminopyrazolo[1,5-a]pyridin-2-yl)oxy]ethanol hydrochloride | | | | 10$^{-3}$ mol |
| Dye support (1) | (*) | (*) | (*) | (*) |
| Demineralized water qs | 100 g | 100 g | 100 g | 100 g |

| | Compositions according to the prior art | | | |
|---|---|---|---|---|
| | C1 | C2 | C3 | C4 |
| 1,2,3,4-Tetrahydroquinoxaline | 10$^{-3}$ mol | 10$^{-3}$ mol | 10$^{-3}$ mol | 10$^{-3}$ mol |
| 4-Aminophenol | 10$^{-3}$ mol | | | |
| Paraphenylene diamine | | 10$^{-3}$ mol | | |
| 2,3-Diamino-6,7-dihydro-1H,5H-pyrazolo[1,2-a]pyrazol-1-one dimethanesulfonate | | | 10$^{-3}$ mol | |
| 2-[(3-aminopyrazolo[1,5-a]pyridin-2-yl)oxy]ethanol hydrochloride | | | | 10$^{-3}$ mol |
| Dye support (1) | (*) | (*) | (*) | (*) |
| Demineralized water qs | 100 g | 100 g | 100 g | 100 g |

(*): dye support (1) pH 9.5

| | |
|---|---|
| 96° ethyl alcohol | 20.8 g |
| 35% aqueous sodium metabisulfite solution | 0.23 g AM |
| Pentasodium salt of diethylenetriaminepentaacetic acid as an aqueous 40% solution | 0.48 g AM |
| C8-C10 alkyl polyglucoside as an aqueous 60% solution | 3.6 g AM |
| Benzyl alcohol | 2.0 g |
| Polyethylene glycol containing 8 units of ethylene oxide | 3.0 g |
| NH$_4$Cl | 4.32 g |
| Aqueous ammonia containing 20% NH$_3$ | 2.94 g |

At the time of use, each composition is mixed with an equal weight of 20-volumes aqueous hydrogen peroxide solution (6% by weight).

Each mixture obtained is applied to locks of grey hair containing 90% white hairs. After a leave-in time of 30 minutes, the locks are rinsed, washed with a standard shampoo, rinsed again and then dried.

The colorimetric measurements were carried out using a Minolta 3600D spectrocolorimeter (illuminant D65, angle 10°, specular component included) in the CIELab system.

According to this system, L indicates the lightness. The lowest is the value of L, the most intense is the color of the hair.

The following results were obtained

| Composition | L* |
|---|---|
| A1 | 27.65 |
| A2 | 19.34 |
| A3 | 16.82 |
| A4 | 18.8 |
| B1 | 23.05 |
| B2 | 15.42 |
| B3 | 16.34 |
| B4 | 17.76 |
| C1 | 52.06 |
| C2 | 33.08 |
| C3 | 52.57 |
| C4 | 37.06 |

The compositions according to the invention allow to obtain a lower value of L*, i.e. a more intense color than the compositions according to the prior art.

The invention claimed is:
1. A 1,2,3,4-Tetrahydropyrido[2,3-b]pyrazin-7-amine compound chosen from those of formula (I) or the addition salts thereof, optical isomers thereof, geometrical isomers thereof, tautomers thereof, or solvates thereof:

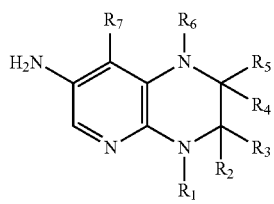

wherein:
R$_2$, R$_3$, R$_4$, R$_5$, and R$_7$, which are identical or different, are independently chosen from:
a hydrogen or halogen atom;
a C$_1$-C$_4$ alkyl group;
a C$_1$-C$_4$ hydroxyalkyl group;
a carboxyl group; or
a (C$_1$-C$_4$)alkoxycarbonyl group;
R$_1$ and R$_6$, which are identical or different, are chosen from:
a hydrogen atom; or
a C$_1$-C$_{10}$ or C$_1$-C$_6$ alkyl group, optionally interrupted with at least one heteroatom chosen from O, S, or at least one —NR group, and/or optionally terminated with at least one —NX$_1$X$_2$ group or a —OX$_3$ group,
X$_1$ and X$_2$, which are identical or different, are independently chosen from:
a hydrogen atom;
a linear C$_1$-C$_6$ alkyl group;
a branched C$_3$-C$_6$ alkyl group;
a linear C$_1$-C$_6$ hydroxyalkyl group; or
a branched C$_3$-C$_6$ hydroxyalkyl group;
or X$_1$ and X$_2$ form, together with the nitrogen atom that bears them, a saturated or unsaturated 5- to 8-membered heterocycle, wherein at least one ring member is optionally a heteroatom chosen from O, S, or N; and/or the heterocycle is optionally substituted with at least one linear or branched C$_1$-C$_4$ alkyl or C$_1$-C$_4$ hydroxyalkyl group;
X$_3$ is chosen from:
a hydrogen atom; or
a linear C$_1$-C$_4$ or branched C$_3$-C$_4$ alkyl group; and
R is chosen from:
a hydrogen atom; or
a linear C$_1$-C$_4$ alkyl group.

2. The 1,2,3,4-Tetrahydropyrido[2,3-b]pyrazin-7-amine compound according to claim 1, wherein R$_2$, R$_3$, R$_4$, R$_5$, and R$_7$, which may be identical or different, are chosen from a hydrogen atom or a C$_1$-C$_4$ alkyl group.

3. The 1,2,3,4-Tetrahydropyrido[2,3-b]pyrazin-7-amine compound according to claim 1, wherein R$_3$, R$_4$, R$_5$, and R$_7$ each represent a hydrogen atom.

4. The 1,2,3,4-Tetrahydropyrido[2,3-b]pyrazin-7-amine compound according to claim 1, wherein:
X$_1$ and X$_2$ independently denote:
a linear C$_1$-C$_4$ alkyl group or a branched C$_3$-C$_4$ alkyl group, or
a linear C$_1$-C$_4$ hydroxyalkyl group or a branched C$_3$-C$_4$ hydroxyalkyl group,
or X$_1$ and X$_2$ form, together with the nitrogen atom that bears them, a saturated or unsaturated 5- to 7-membered heterocycle, wherein at least one ring member is optionally substituted with a heteroatom chosen from O, S, or N; and/or the heterocycle is optionally substituted with at least one linear or branched C$_1$-C$_4$ alkyl or C$_1$-C$_4$ hydroxyalkyl group.

5. The 1,2,3,4-Tetrahydropyrido[2,3-b]pyrazin-7-amine compound according to claim 1, wherein:
X$_3$ is a hydrogen atom; and
R is chosen from a hydrogen atom or a methyl group.

6. The 1,2,3,4-Tetrahydropyrido[2,3-b]pyrazin-7-amine compound according to claim 5, wherein the saturated or unsaturated 5- to 7-membered heterocyclic group wherein at least one of the ring members is optionally substituted with a heteroatom chosen from O, S, or N is chosen from imidazole, piperazine, pyrrolidine, morpholine, or piperidine rings.

7. The 1,2,3,4-Tetrahydropyrido[2,3-b]pyrazin-7-amine compound according to claim 1, wherein:
X$_3$ is a hydrogen atom; and
R is a hydrogen atom.

8. The 1,2,3,4-Tetrahydropyrido[2,3-b]pyrazin-7-amine compound according to claim 1, wherein R$_1$ and R$_6$ are identical and are chosen from a hydrogen atom or a C$_1$-C$_6$ alkyl group, optionally terminating with at least one group chosen from a —NX$_1$X$_2$ group or an —OH group,
wherein X$_1$ and X$_2$ are independently chosen from:
a linear C$_1$-C$_4$ alkyl group;
a branched C$_3$-C$_4$ alkyl group;
a linear C$_1$-C$_4$ hydroxyalkyl group; or
a branched C$_3$-C$_4$ hydroxyalkyl group;
or X$_1$ and X$_2$ form, together with the nitrogen atom that bears them, a saturated or unsaturated 5- to 7-membered heterocycle, wherein at least one ring member is optionally substituted with a heteroatom chosen from O, S, or N; and/or the heterocycle is optionally substituted with at least one linear or branched C$_1$-C$_4$ alkyl or C$_1$-C$_4$ hydroxyalkyl group.

9. The 1,2,3,4-Tetrahydropyrido[2,3-b]pyrazin-7-amine compound according to claim 1, wherein R$_1$ and R$_6$ are identical and are chosen from a hydrogen atom or a C$_1$-C$_6$ alkyl group, optionally terminating with one group chosen from a —NX$_1$X$_2$ group or an —OH group,
wherein X$_1$ and X$_2$ are independently chosen from:
a linear C$_1$-C$_4$ alkyl group;
a branched C$_3$-C$_4$ alkyl group;
a linear C$_1$-C$_4$ hydroxyalkyl group; or
a branched C$_3$-C$_4$ hydroxyalkyl group;
or X$_1$ and X$_2$ form, together with the nitrogen atom that bears them, a saturated or unsaturated 5- to 7-membered heterocycle, wherein at least one ring member is optionally substituted with a heteroatom chosen from O, S, or N; and/or the heterocycle is optionally substituted with at least one linear or branched C$_1$-C$_4$ alkyl or C$_1$-C$_4$ hydroxyalkyl group.

10. The 1,2,3,4-Tetrahydropyrido[2,3-b]pyrazin-7-amine compound according to claim 1, wherein the compound is chosen from:

51 52

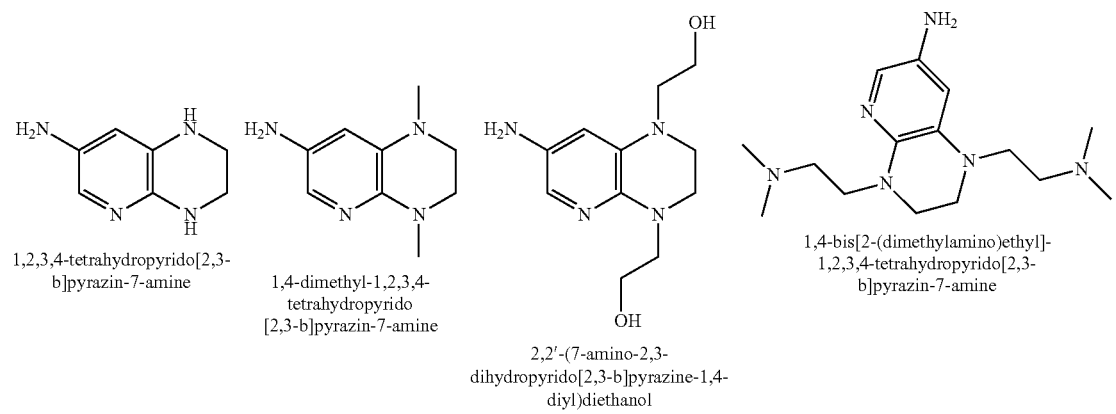

1,2,3,4-tetrahydropyrido[2,3-b]pyrazin-7-amine 1,4-dimethyl-1,2,3,4-tetrahydropyrido[2,3-b]pyrazin-7-amine 2,2'-(7-amino-2,3-dihydropyrido[2,3-b]pyrazine-1,4-diyl)diethanol 1,4-bis[2-(dimethylamino)ethyl]-1,2,3,4-tetrahydropyrido[2,3-b]pyrazin-7-amine

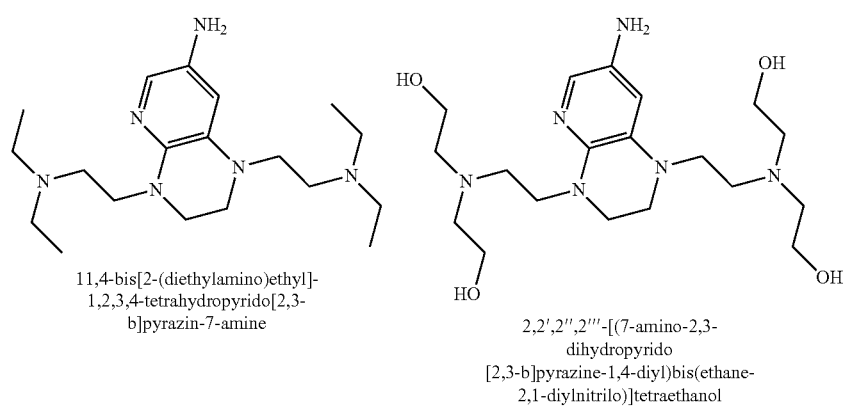

11,4-bis[2-(diethylamino)ethyl]-1,2,3,4-tetrahydropyrido[2,3-b]pyrazin-7-amine 2,2',2'',2'''-[(7-amino-2,3-dihydropyrido[2,3-b]pyrazine-1,4-diyl)bis(ethane-2,1-diylnitrilo)]tetraethanol

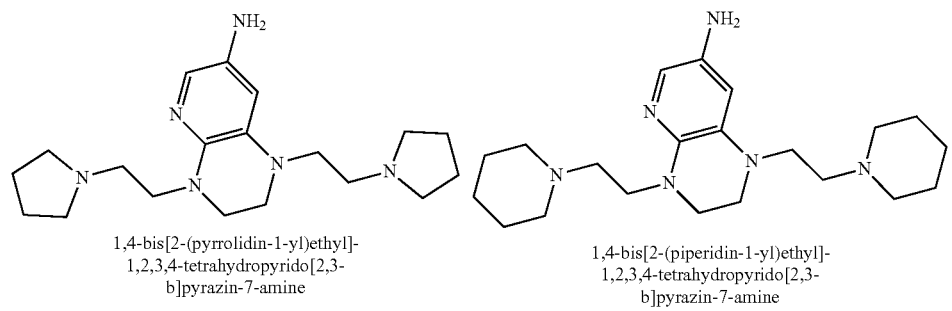

1,4-bis[2-(pyrrolidin-1-yl)ethyl]-1,2,3,4-tetrahydropyrido[2,3-b]pyrazin-7-amine 1,4-bis[2-(piperidin-1-yl)ethyl]-1,2,3,4-tetrahydropyrido[2,3-b]pyrazin-7-amine

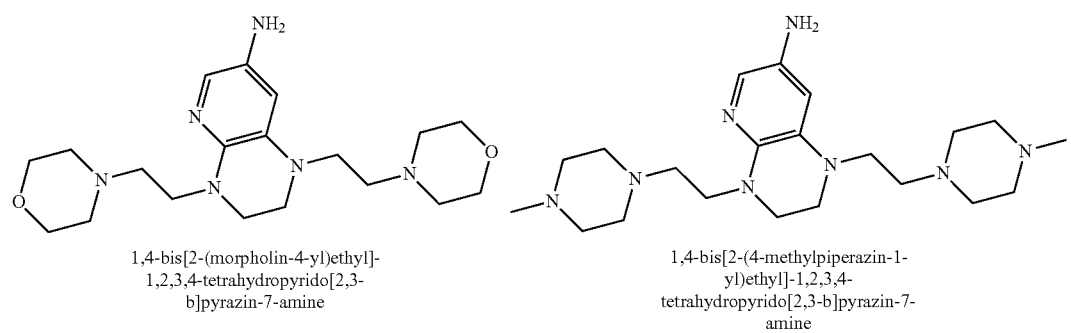

1,4-bis[2-(morpholin-4-yl)ethyl]-1,2,3,4-tetrahydropyrido[2,3-b]pyrazin-7-amine 1,4-bis[2-(4-methylpiperazin-1-yl)ethyl]-1,2,3,4-tetrahydropyrido[2,3-b]pyrazin-7-amine -continued

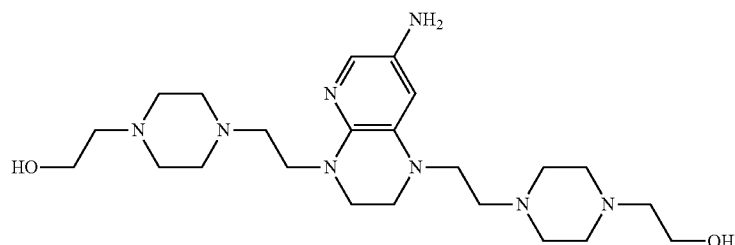

2,2'-[(7-amino-2,3-dihydropyrido[2,3-b]pyrazine-1,4-diyl)bis(ethane-2,1-diylpiperazine-4,1-diyl)]diethanol

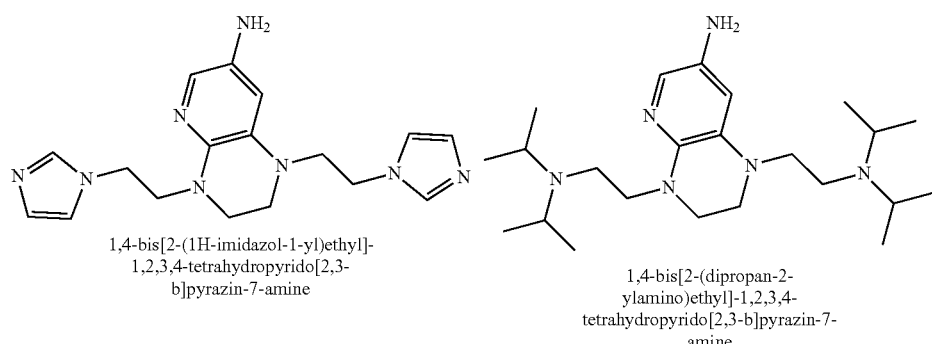

1,4-bis[2-(1H-imidazol-1-yl)ethyl]-1,2,3,4-tetrahydropyrido[2,3-b]pyrazin-7-amine 1,4-bis[2-(dipropan-2-ylamino)ethyl]-1,2,3,4-tetrahydropyrido[2,3-b]pyrazin-7-amine

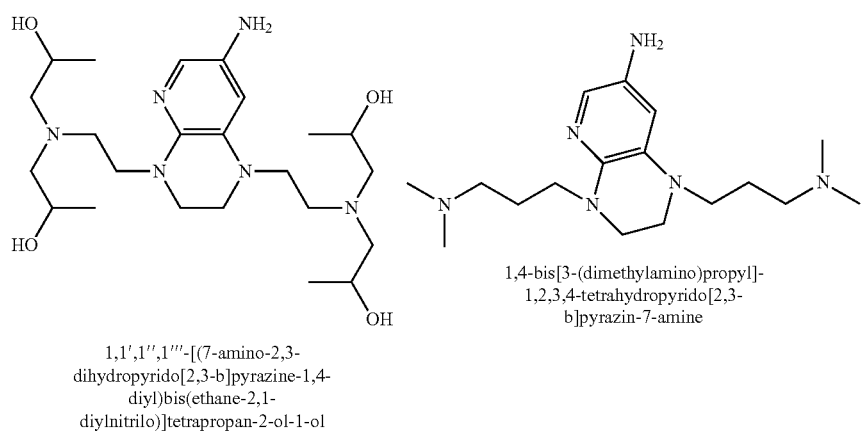

1,1',1'',1'''-[(7-amino-2,3-dihydropyrido[2,3-b]pyrazine-1,4-diyl)bis(ethane-2,1-diylnitrilo)]tetrapropan-2-ol-1-ol 1,4-bis[3-(dimethylamino)propyl]-1,2,3,4-tetrahydropyrido[2,3-b]pyrazin-7-amine

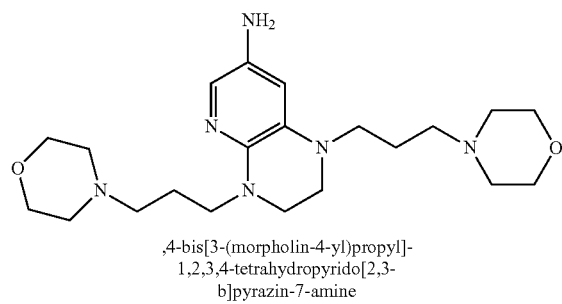

,4-bis[3-(morpholin-4-yl)propyl]-1,2,3,4-tetrahydropyrido[2,3-b]pyrazin-7-amine

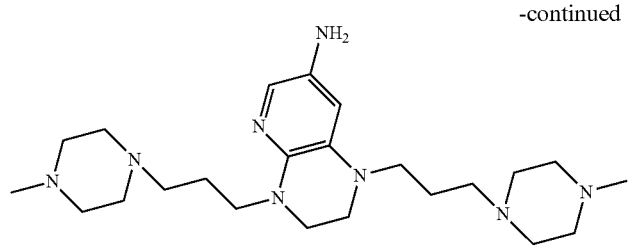

1,4-bis[3-(4-methylpiperazin-1-yl)propyl]-1,2,3,4-tetrahydropyrido[2,3-b]pyrazin-7-amine

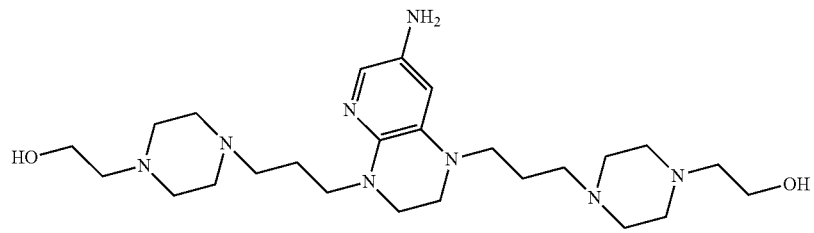

2,2'-[(7-amino-2,3-dihydropyrido[2,3-b]pyrazine-1,4-diyl)bis(propane-3,1-diylpiperazine-4,1-diyl)]diethanol or the addition salts thereof, optical isomers thereof, geometrical isomers thereof, tautomers thereof, or solvates thereof.

11. The 1,2,3,4-Tetrahydropyrido[2,3-b]pyrazin-7-amine compound according to claim 1 wherein $R_1$ and $R_6$ are identical and are chosen from a $C_1$-$C_6$ alkyl group interrupted with an oxygen atom or an NH group, and optionally terminated with at least one group chosen from an —$NX_1X_2$ group or an —OH group, wherein $X_1$ and $X_2$ are independently chosen from:
  a linear $C_1$-$C_4$ alkyl group;
  a branched $C_3$-$C_4$ alkyl group;
  a linear $C_1$-$C_4$ hydroxyalkyl group; or
  a branched $C_3$-$C_4$ hydroxyalkyl group;

or $X_1$ and $X_2$ form, together with the nitrogen atom that bears them, a saturated or unsaturated 5- to 7-membered heterocycle, wherein at least one ring member is optionally substituted with a heteroatom chosen from O, S, or N; and/or the heterocycle is optionally substituted with at least one linear or branched $C_1$-$C_4$ alkyl or $C_1$-$C_4$ hydroxyalkyl group.

12. The 1,2,3,4-Tetrahydropyrido[2,3-b]pyrazin-7-amine compound according to claim 1, wherein the compound is chosen from:

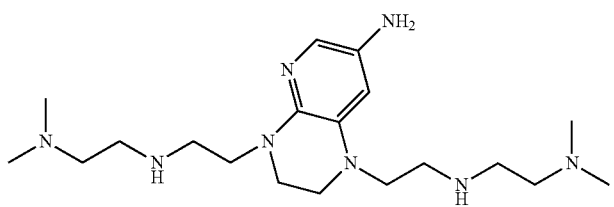

N1,N1'-[(7-amino-2,3-dihydropyrido[2,3-b]pyrazine-1,4-diyl)diethane-2,1-diyl]bis(N2,N2-dimethylethane-1,2-diamine)

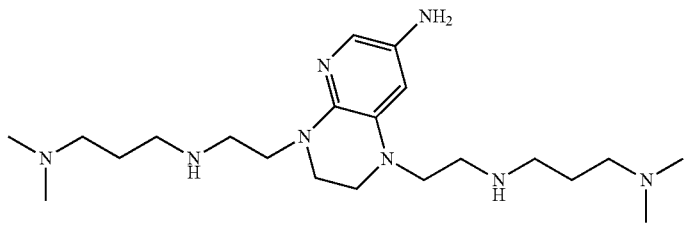

N1,N1'-[(7-amino-2,3-dihydropyrido[2,3-b]pyrazine-1,4-diyl)diethane-2,1-diyl]bis(N3,N3-dimethylpropane-1,3-diamine)

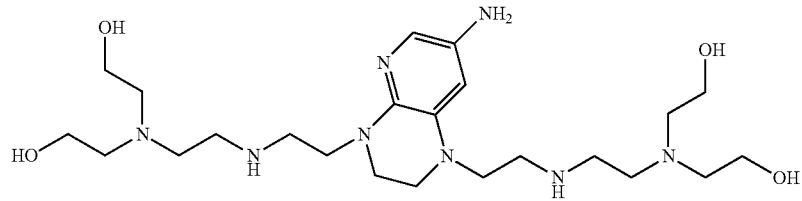

2,2',2'',2'''-[(7-amino-2,3-dihydropyrido[2,3-b]pyrazine-1,4-diyl)bis(ethane-2,1-diyliminoethane-2,1-diylnitrilo)]tetraethanol

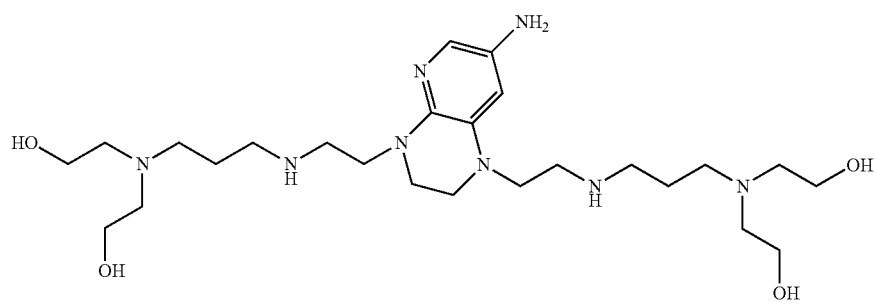

2,2',2'',2'''-[(7-amino-2,3-dihydropyrido[2,3-b]pyrazine-1,4-diyl)bis(ethane-2,1-diyliminopropane-3,1-diylnitrilo)]tetraethanol

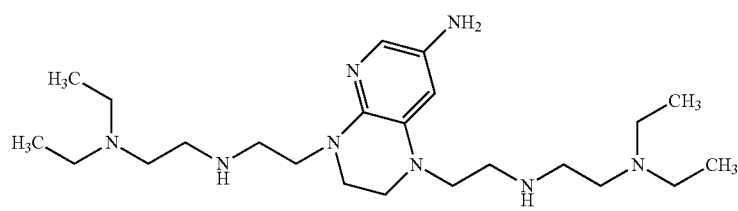

N1,N1'-[(7-amino-2,3-dihydropyrido[2,3-b]pyrazine-1,4-diyl)diethane-2,1-diyl]bis(N2,N2-diethylethane-1,2-diamine)

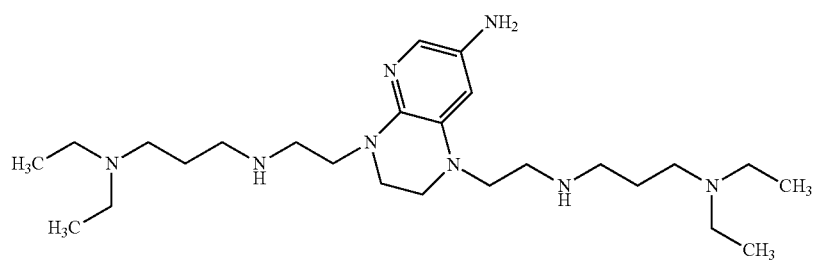

N1,N1'-[(7-amino-2,3-dihydropyrido[2,3-b]pyrazine-1,4-diyl)diethane-2,1-diyl]bis(N3,N3-diethylpropane-1,3-diamine)

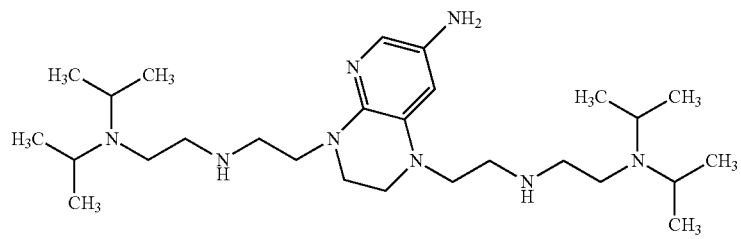
N1,N1'-[(7-amino-2,3-dihydropyrido[2,3-b]pyrazine-1,4-diyl)diethane-2,1-diyl]bis(N2,N2-di(propan-2-yl)ethane-1,2-diamine]
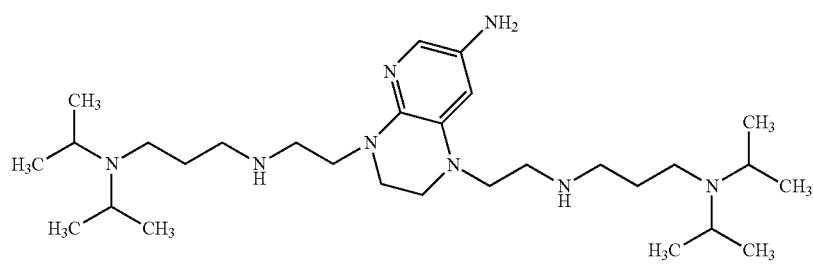
N1,N1'-[(7-amino-2,3-dihydropyrido[2,3-b]pyrazine-1,4-diyl)diethane-2,1-diyl]bis[N3,N3-di(propan-2-yl)propane-1,3-diamine]
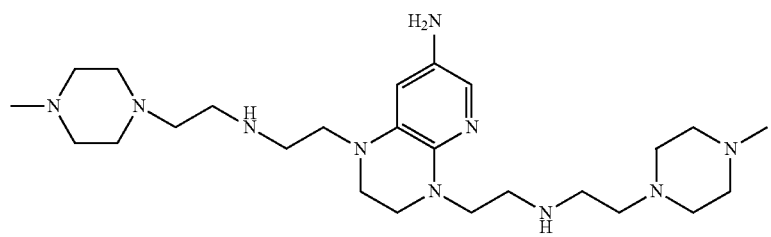
1,4-bis(2-{[2-(4-methylpiperazin-1-yl)ethyl]amino}ethyl)-1,2,3,4-tetrahydropyrido[2,3-b]pyrazin-7-amine
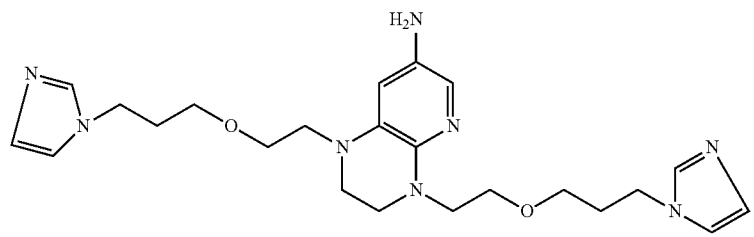
1,4-bis{2-[2-(1H-imidazol-1-yl)ethoxy]ethyl}-1,2,3,4-tetrahydropyrido[2,3-b]pyrazin-7-amine

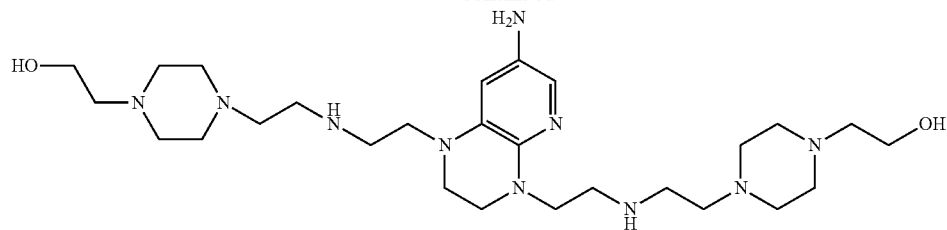

2,2'-[(7-amino-2,3-
dihydropyrido[2,3-b]pyrazine-1,4-
diyl)bis(ethane-2,1-
diyliminoethane-2,1-
diylpiperazine-4,1-diyl)]diethanol

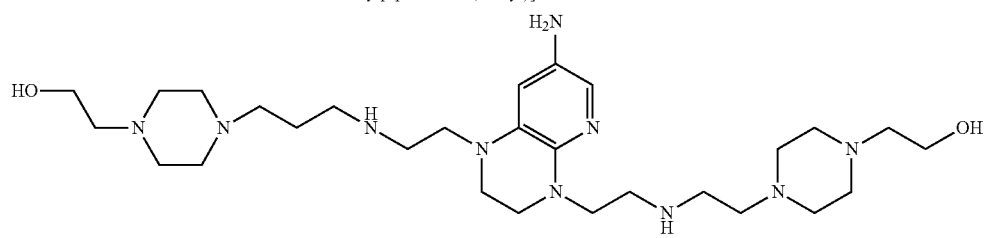

2,2'-[(7-amino-2,3-
dihydropyrido[2,3-b]pyrazine-1,4-
diyl)bis(ethane-2,1-
diyliminopropane-3,1-
diylpiperazine-4,1-diyl)]diethanol

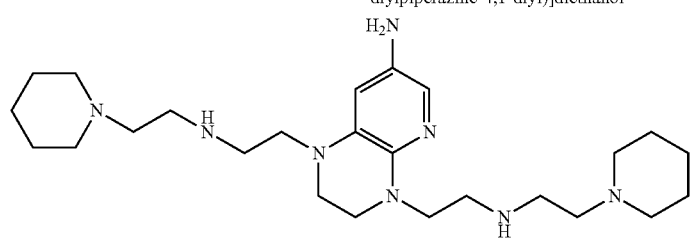

1,4-bis(2-{[2-(piperidin-1-
yl)ethyl]amino}ethyl)-1,2,3,4-
tetrahydropyrido[2,3-b]pyrazin-7-
amine

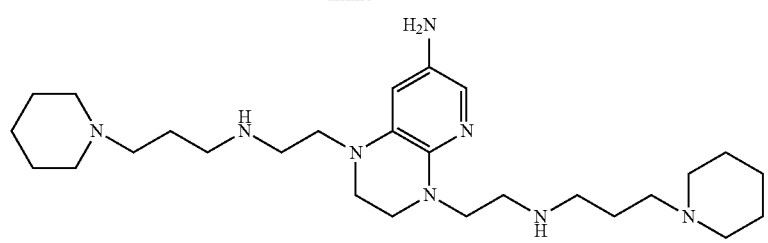

1,4-bis(2-{[3-(piperidin-1-
yl)propyl]amino}ethyl)-1,2,3,4-
tetrahydropyrido[2,3-b]pyrazin-7-
amine

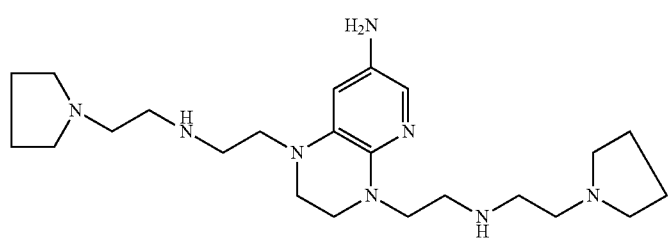

1,4-bis(2-{[2-(pyrrolidin-1-
yl)ethyl]amino}ethyl)-1,2,3,4-
tetrahydropyrido[2,3-b]pyrazin-7-
amine

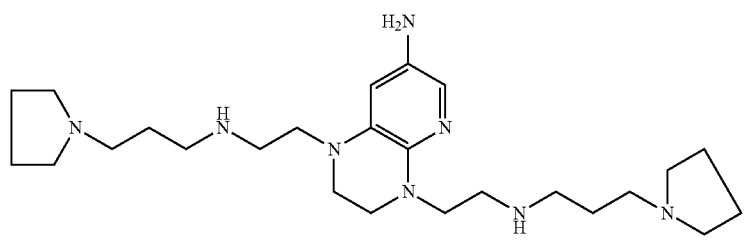
1,4-bis(2-{[3-(pyrrolidin-1-yl)propyl]amino}ethyl)-1,2,3,4-tetrahydropyrido[2,3-b]pyrazin-7-amine
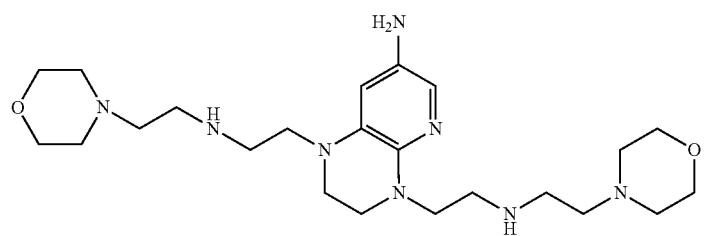
1,4-bis(2-{[2-(morpholin-4-yl)ethyl]amino}ethyl)-1,2,3,4-tetrahydropyrido[2,3-b]pyrazin-7-amine
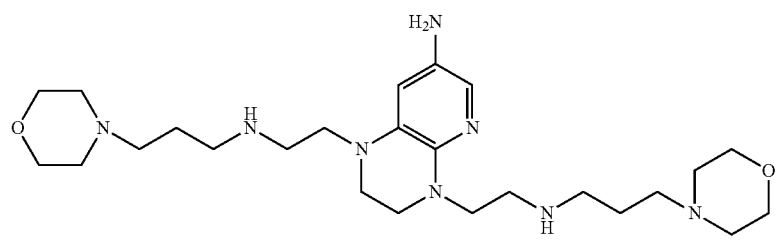
1,4-bis(2-{[3-(morpholin-4-yl)propyl]amino}ethyl)-1,2,3,4-tetrahydropyrido[2,3-b]pyrazin-7-amine
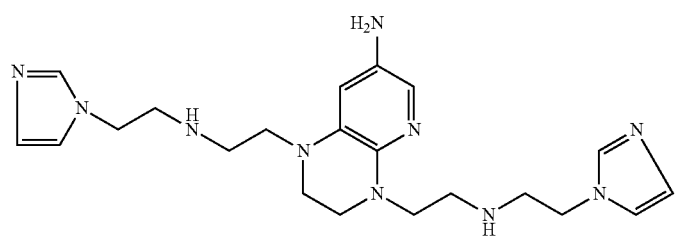
1,4-bis(2-{[2-(1H-imidazol-1-yl)ethyl]amino}ethyl)-1,2,3,4-tetrahydropyrido[2,3-b]pyrazin-7-amine
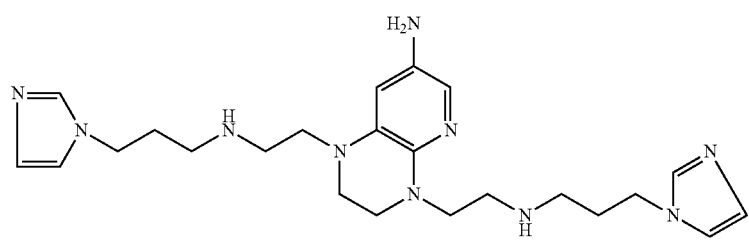
1,4-bis(2-{[3-(1H-imidazol-1-yl)propyl]amino}ethyl)-1,2,3,4-tetrahydropyrido[2,3-b]pyrazin-7-amine

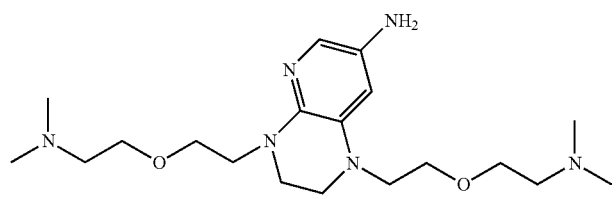

1,4-bis{2-[2-(dimethylamino)ethoxy]ethyl}-1,2,3,4-tetrahydropyrido[2,3-b]pyrazin-7-amine

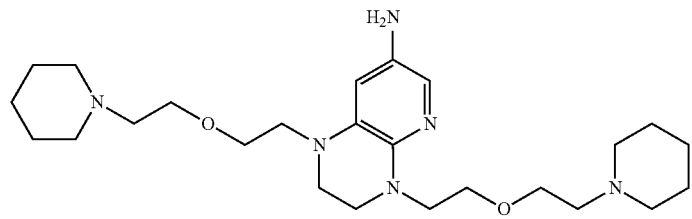

1,4-bis{2-[2-(piperidin-1-yl)ethoxy]ethyl}-1,2,3,4-tetrahydropyrido[2,3-b]pyrazin-7-amine

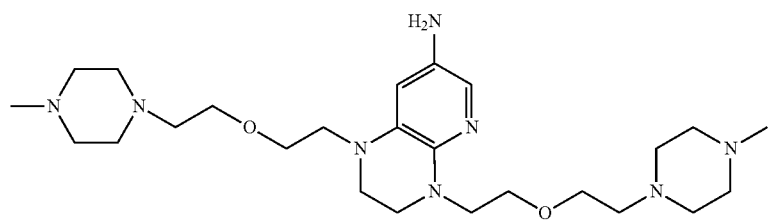

1,4-bis{2-[2-(4-methylpiperazin-1-yl)ethoxy]ethyl}-1,2,3,4-tetrahydropyrido[2,3-b]pyrazin-7-amine

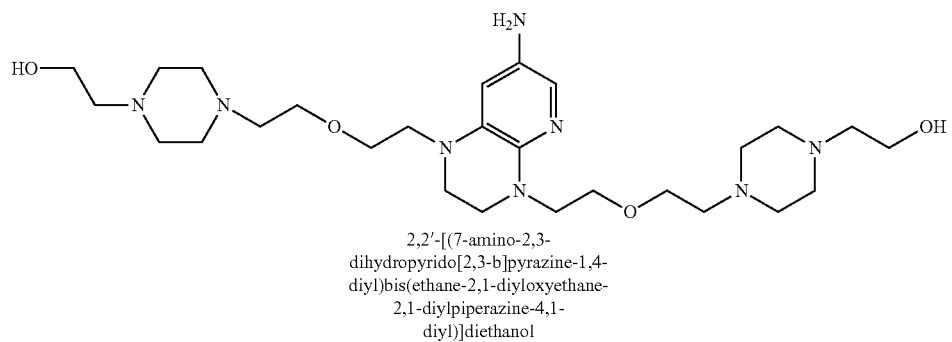

2,2'-[(7-amino-2,3-dihydropyrido[2,3-b]pyrazine-1,4-diyl)bis(ethane-2,1-diyloxyethane-2,1-diylpiperazine-4,1-diyl)]diethanol

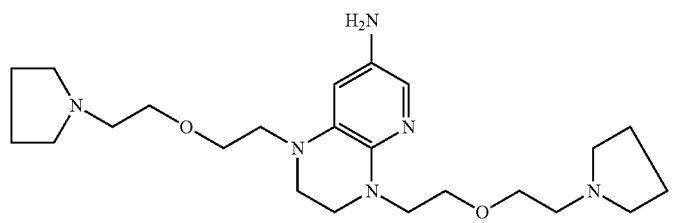

1,4-bis{2-[2-(pyrrolidin-1-yl)ethoxy]ethyl}-1,2,3,4-tetrahydropyrido[2,3-b]pyrazin-7-amine

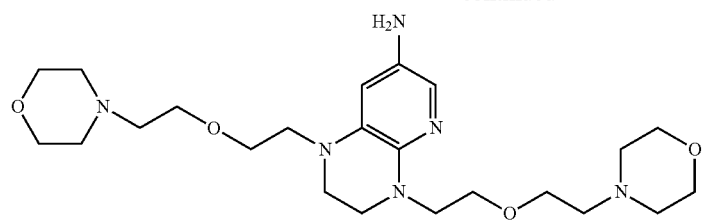
1,4-bis(2-{[2-(morpholin-4-yl)ethyl]amino}ethyl)-1,2,3,4-tetrahydropyrido[2,3-b]pyrazin-7-amine
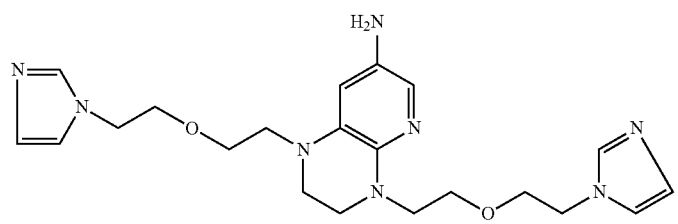
1,4-bis{2-[2-(1H-imidazol-1-yl)ethoxy]ethyl}-1,2,3,4-tetrahydropyrido[2,3-b]pyrazin-7-amine
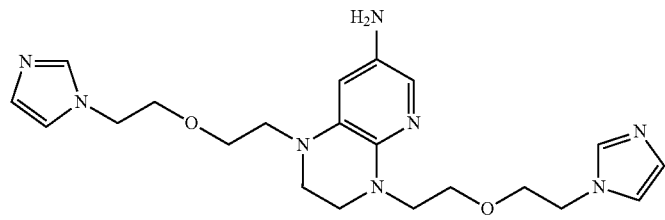
1,4-bis{2-[2-(1H-imidazol-1-yl)ethoxy]ethyl}-1,2,3,4-tetrahydropyrido[2,3-b]pyrazin-7-amine
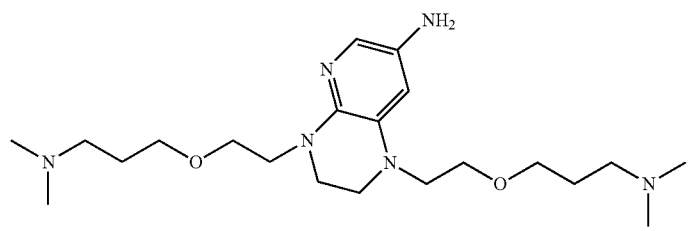
1,4-bis{2-[3-(dimethylamino)propoxy]ethyl}-1,2,3,4-tetrahydropyrido[2,3-b]pyrazin-7-amine
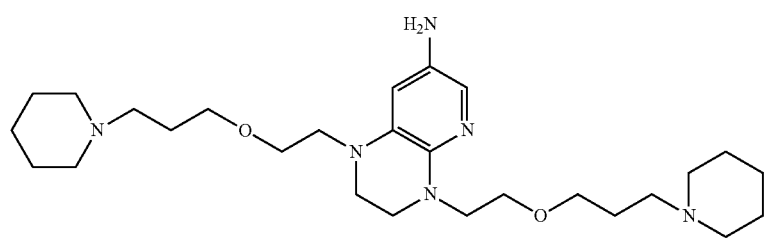
11,4-bis{2-[3-(piperidin-1-yl)propoxy]ethyl}-1,2,3,4-tetrahydropyrido[2,3-b]pyrazin-7-amine -continued

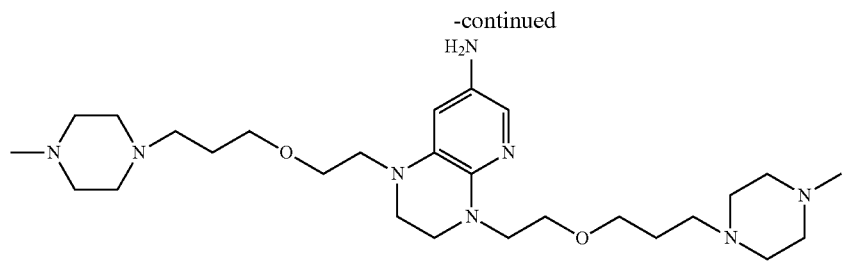

1,4-bis{2-[3-(4-methylpiperazin-1-yl)propoxy]ethyl}-1,2,3,4-tetrahydropyrido[2,3-b]pyrazin-7-amine

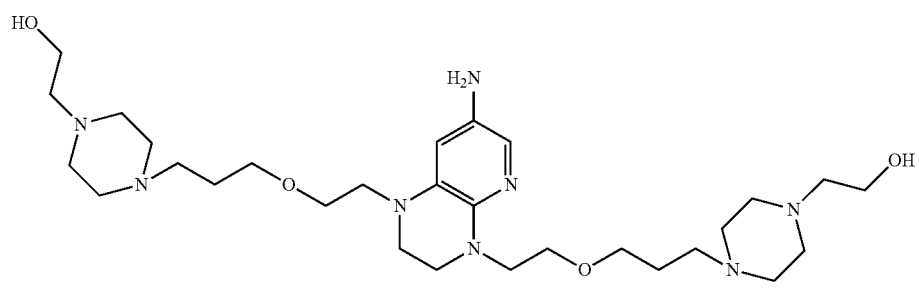

2,2'-[(7-amino-2,3-dihydropyrido[2,3-b]pyrazine-1,4-diyl)bis(ethane-2,1-diyloxypropane-3,1-diylpiperazine-4,1-diyl)]diethanol

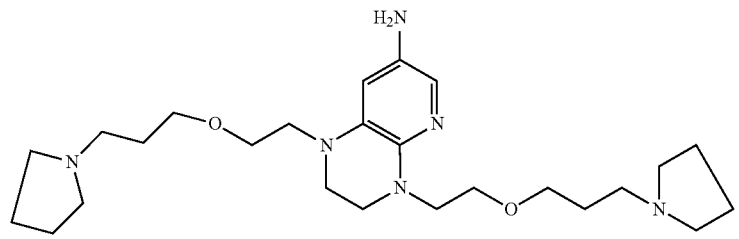

1,4-bis{2-[3-(pyrrolidin-1-yl)propoxy]ethyl}-1,2,3,4-tetrahydropyrido[2,3-b]pyrazin-7-amine

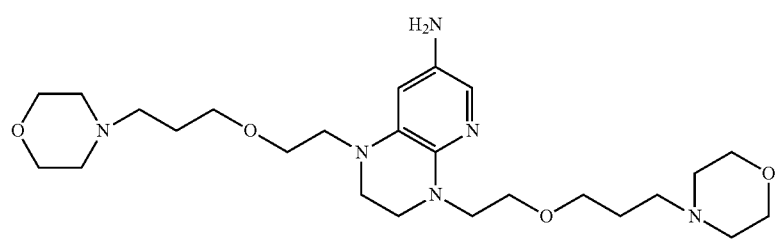

11,4-bis{2-[3-(morpholin-4-yl)propoxy]ethyl}-1,2,3,4-tetrahydropyrido[2,3-b]pyrazin-7-amine

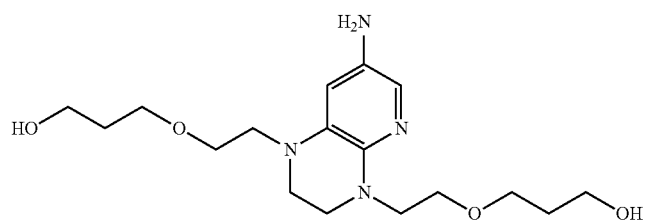

3,3'-[(7-amino-2,3-dihydropyrido[2,3-b]pyrazine-1,4-diyl)bis(ethane-2,1-diyloxy)]dipropan-1-ol

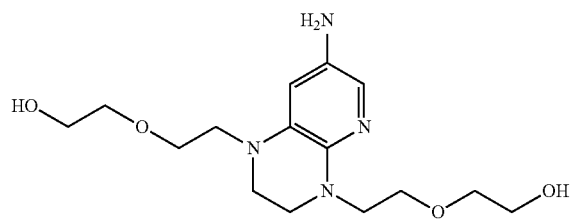
2,2'-[(7-amino-2,3-
dihydropyrido[2,3-b]pyrazine-1,4-
diyl)bis(ethane-2,1-
diyloxy)]diethanol
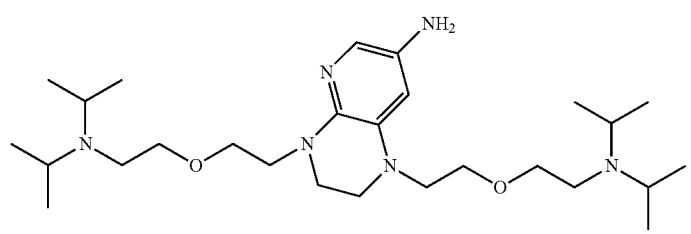
1,4-bis{2-[2-(dipropan-2-
ylamino)ethoxy]ethyl}-1,2,3,4-
tetrahydropyrido[2,3-b]pyrazin-7-
amine
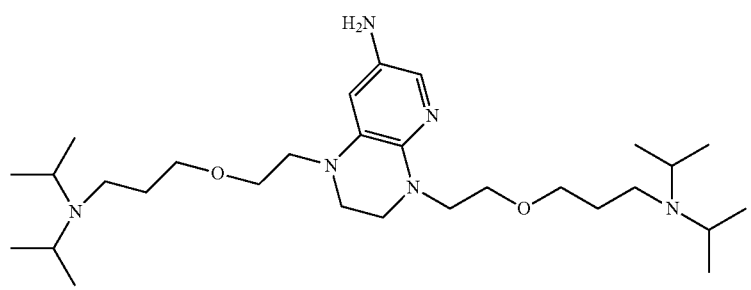
1,4-bis{2-[3-(dipropan-2-
ylamino)propoxy]ethyl}-1,2,3,4-
tetrahydropyrido[2,3-b]pyrazin-7-
amine
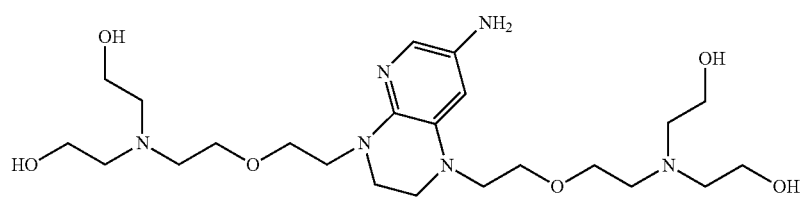
2,2',2'',2'''-[(7-amino-2,3-
dihydropyrido[2,3-b]pyrazine-1,4-
diyl)bis(ethane-2,1-diyloxyethane-
2,1-diylnitrilo)]tetraethanol

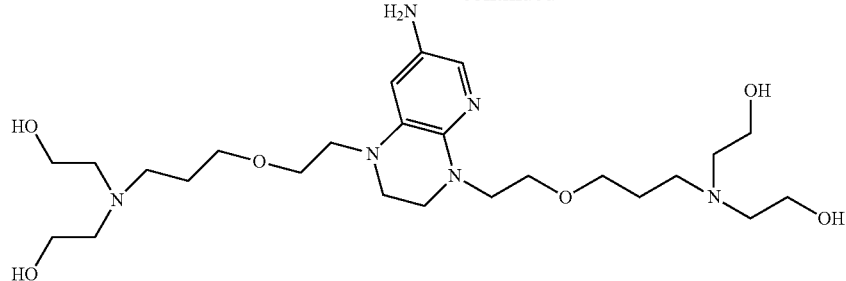

2,2′,2″,2‴-[(7-amino-2,3-dihydropyrido[2,3-b]pyrazine-1,4-diyl)bis(ethane-2,1-diyloxypropane-3,1-diylnitrilo)]tetraethanol or the addition salts thereof, optical isomers thereof, geometrical isomers thereof, tautomers thereof, or solvates thereof.

13. The 1,2,3,4-Tetrahydropyrido[2,3-b]pyrazin-7-amine compound according to claim 1, wherein $R_1$ and $R_6$ are different and are independently chosen from a hydrogen atom or a $C_1$-$C_6$ alkyl group, optionally terminated with at least one group chosen from an $NX_1X_2$ group or an OH group, wherein $X_1$ and $X_2$ are independently chosen from:
a linear $C_1$-$C_4$ alkyl group;
a branched $C_3$-$C_4$ alkyl group;
a linear $C_1$-$C_4$ hydroxyalkyl group; or
a branched $C_3$-$C_4$ hydroxyalkyl group;

or $X_1$ and $X_2$ form, together with the nitrogen atom that bears them, a saturated or unsaturated 5- to 7-membered heterocycle, wherein at least one ring member is optionally substituted with a heteroatom chosen from O, S, or N; and/or the heterocycle is optionally substituted with at least one linear or branched $C_1$-$C_4$ alkyl or $C_1$-$C_4$ hydroxyalkyl group.

14. The 1,2,3,4-Tetrahydropyrido[2,3-b]pyrazin-7-amine compound according to claim 1, wherein $R_1$ and $R_6$ are different and are independently chosen from a hydrogen atom or a $C_1$-$C_6$ alkyl group, optionally terminated with an OH group.

15. The 1,2,3,4-Tetrahydropyrido[2,3-b]pyrazin-7-amine compound according to claim 1, wherein the compound is chosen from:

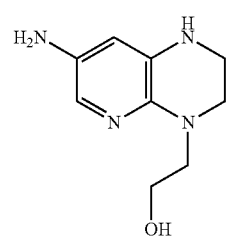

2-(7-amino-2,3-dihydropyrido[2,3b]pyrazin-4(1H)-yl)ethanol

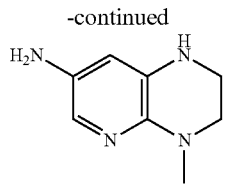

4-methyl-1,2,3,4-tetrahydropyrido[2,3-b]pyrazin-7-amine

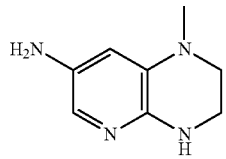

1-methyl-1,2,3,4 tetrahydropyrido[2,3-b]pyrazin-7-amine

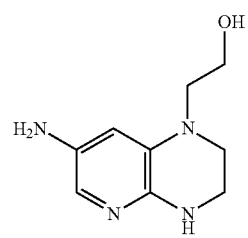

2-(7-amino-3,4-dihydropyrido[2,3-b]pyrazin-1(2H)-yl)ethanol

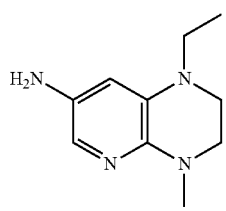

1-ethyl-4-methyl-1,2,3,4-tetrahydropyrido[2,3-b]pyrazin-7-amine

-continued

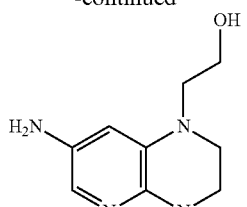

22-(7-amino-4-methyl-3,4-dihydropyrido[2,3-b]pyrazin-1(2H)-yl)ethanol

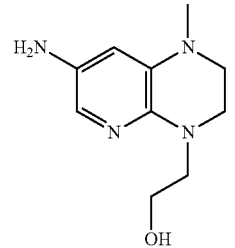

2-(7-amino-1-methyl-2,3-dihydropyrido[2,3-b]pyrazin-4(1H)-yl)ethanol

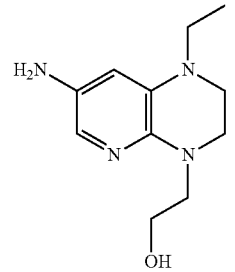

2-(7-amino-1-ethyl-2,3-dihydropyrido[2,3-b]pyrazin-4(1H)-yl)ethanol

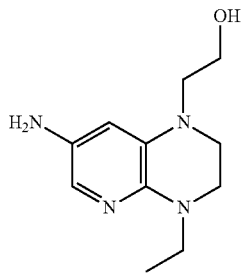

2-(7-amino-4-ethyl-3,4-dihydropyrido[2,3-b]pyrazin-1(2H)-yl)ethanol

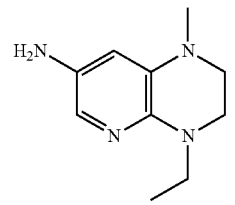

4-ethyl-1-methyl-1,2,3,4-tetrahydropyrido[2,3-b]pyrazin-7-amine or the addition salts thereof, optical isomers thereof, geometrical isomers thereof, tautomers thereof, or solvates thereof.

16. A composition for dyeing keratin fibers, the composition comprising, in a medium that is suitable for dyeing keratin fibers, at least one 1,2,3,4-Tetrahydropyrido[2,3-b]pyrazin-7-amine compound chosen from those of formula (I) or the addition salts thereof, the optical isomers or geometrical isomers thereof, or the tautomers and/or solvates thereof:

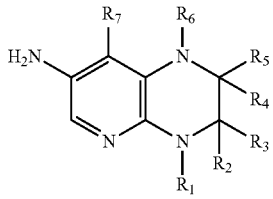

wherein:

$R_2$, $R_3$, $R_4$, $R_5$, and $R_7$, which are identical or different, are independently chosen from:

a hydrogen or halogen atom;

a $C_1$-$C_4$ alkyl group;

a $C_1$-$C_4$ hydroxyalkyl group;

a carboxyl group; or a ($C_1$-$C_4$)alkoxycarbonyl group;

$R_1$ and $R_6$, which are identical or different, are chosen from:

a hydrogen atom; or a $C_1$-$C_{10}$ or $C_1$-$C_6$ alkyl group, optionally interrupted with at least one heteroatom chosen from O, S, or at least one —NR group, and/or optionally terminated with at least one —$NX_1X_2$ group or a —$OX_3$ group, $X_1$ and $X_2$, which are identical or different, are independently chosen from:

a hydrogen atom;

a linear $C_1$-$C_6$ alkyl group;

a branched $C_3$-$C_6$ alkyl group;

a linear $C_1$-$C_6$ hydroxyalkyl group; or a branched $C_3$-$C_6$ hydroxyalkyl group;

or $X_1$ and $X_2$ form, together with the nitrogen atom that bears them, a saturated or unsaturated 5- to 8-membered heterocycle, wherein at least one ring member is optionally substituted with a heteroatom chosen from O, S, or N; and/or the heterocycle is optionally substituted with at least one linear or branched $C_1$-$C_4$ alkyl or $C_1$-$C_4$ hydroxyalkyl group;

$X_3$ is chosen from:

a hydrogen atom; or a linear $C_1$-$C_4$ or branched $C_3$-$C_4$ alkyl group; and R is chosen from:

a hydrogen atom; or a linear $C_1$-$C_4$ alkyl group.

17. The composition of claim 16, wherein the total amount of 1,2,3,4-Tetrahydropyrido[2,3-b]pyrazin-7-amine compound ranges from about 0.001% to about 10% by weight, relative to the total weight of the composition.

18. The composition of claim 16, wherein the at least one 1,2,3,4-Tetrahydropyrido[2,3-b]pyrazin-7-amine compound is chosen from:

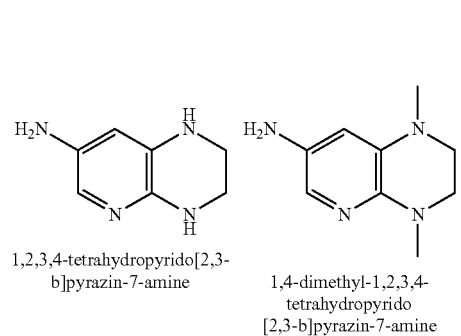
1,2,3,4-tetrahydropyrido[2,3-b]pyrazin-7-amine

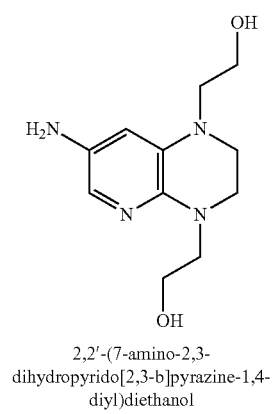
1,4-dimethyl-1,2,3,4-tetrahydropyrido[2,3-b]pyrazin-7-amine

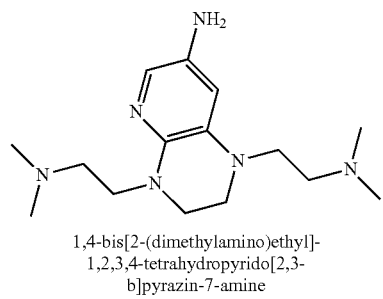
2,2'-(7-amino-2,3-dihydropyrido[2,3-b]pyrazine-1,4-diyl)diethanol 1,4-bis[2-(dimethylamino)ethyl]-1,2,3,4-tetrahydropyrido[2,3-b]pyrazin-7-amine

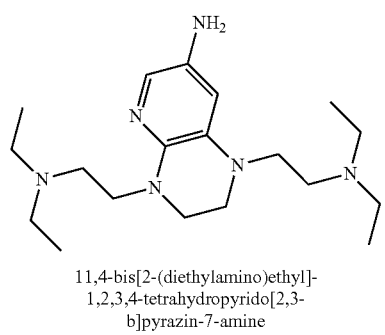
11,4-bis[2-(diethylamino)ethyl]-1,2,3,4-tetrahydropyrido[2,3-b]pyrazin-7-amine

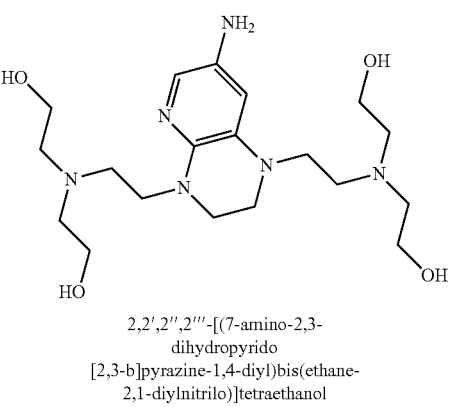
2,2',2'',2'''-[(7-amino-2,3-dihydropyrido[2,3-b]pyrazine-1,4-diyl)bis(ethane-2,1-diylnitrilo)]tetraethanol

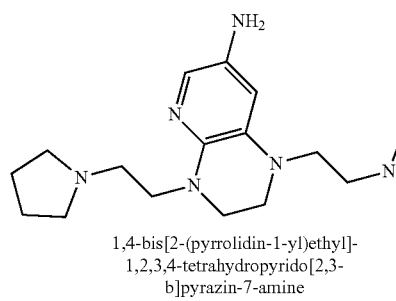
1,4-bis[2-(pyrrolidin-1-yl)ethyl]-1,2,3,4-tetrahydropyrido[2,3-b]pyrazin-7-amine

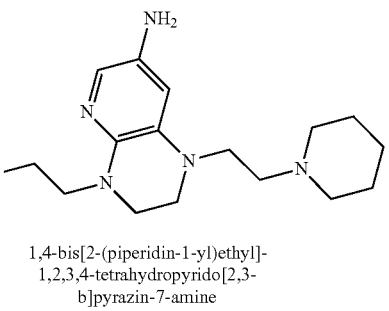
1,4-bis[2-(piperidin-1-yl)ethyl]-1,2,3,4-tetrahydropyrido[2,3-b]pyrazin-7-amine

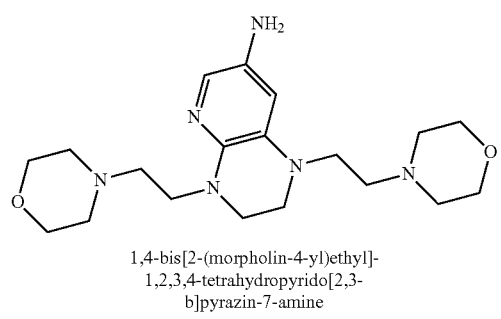
1,4-bis[2-(morpholin-4-yl)ethyl]-1,2,3,4-tetrahydropyrido[2,3-b]pyrazin-7-amine

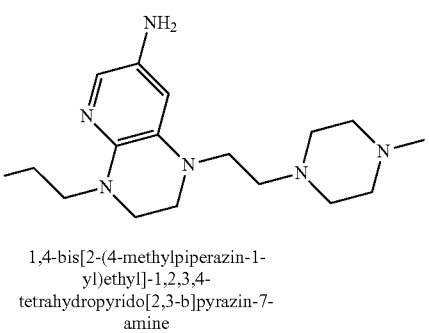
1,4-bis[2-(4-methylpiperazin-1-yl)ethyl]-1,2,3,4-tetrahydropyrido[2,3-b]pyrazin-7-amine -continued

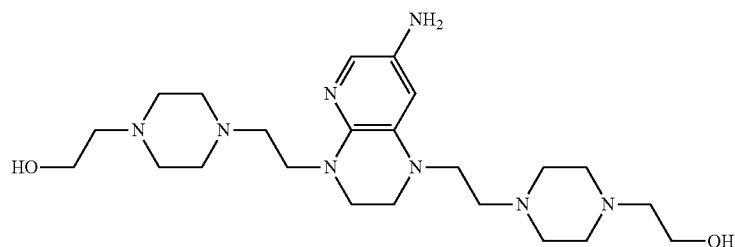

2,2'-[(7-amino-2,3-dihydropyrido[2,3-b]pyrazine-1,4-diyl)bis(ethane-2,1-diylpiperazine-4,1-diyl)]diethanol

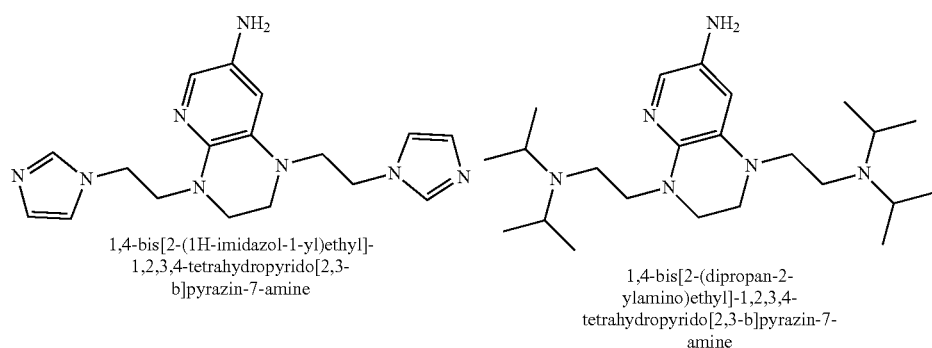

1,4-bis[2-(1H-imidazol-1-yl)ethyl]-1,2,3,4-tetrahydropyrido[2,3-b]pyrazin-7-amine 1,4-bis[2-(dipropan-2-ylamino)ethyl]-1,2,3,4-tetrahydropyrido[2,3-b]pyrazin-7-amine

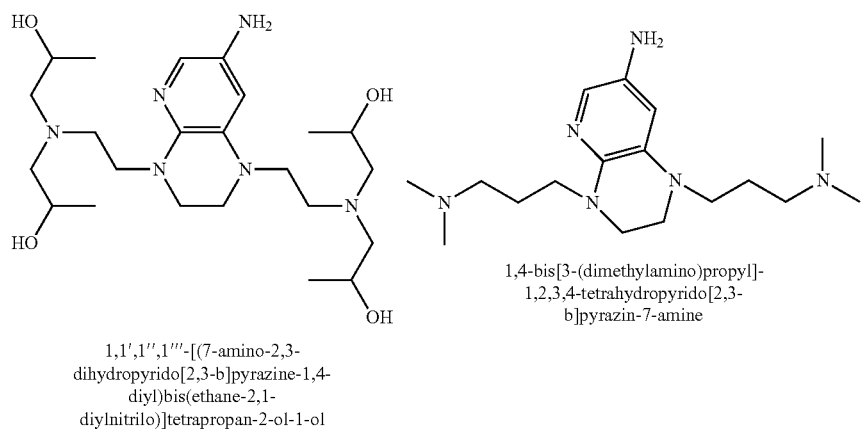

1,1',1'',1'''-[(7-amino-2,3-dihydropyrido[2,3-b]pyrazine-1,4-diyl)bis(ethane-2,1-diylnitrilo)]tetrapropan-2-ol-1-ol 1,4-bis[3-(dimethylamino)propyl]-1,2,3,4-tetrahydropyrido[2,3-b]pyrazin-7-amine

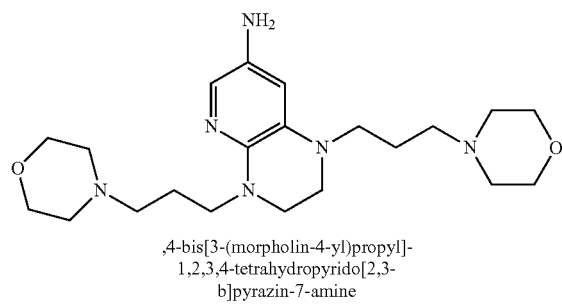

,4-bis[3-(morpholin-4-yl)propyl]-1,2,3,4-tetrahydropyrido[2,3-b]pyrazin-7-amine

-continued

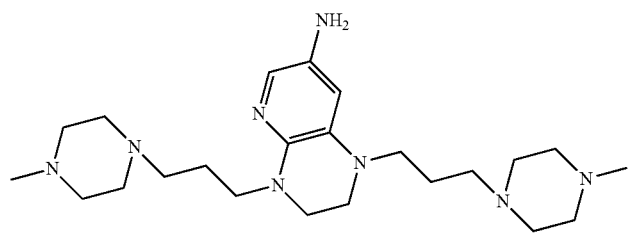

1,4-bis[3-(4-methylpiperazin-1-yl)propyl]-1,2,3,4-tetrahydropyrido[2,3-b]pyrazin-7-amine

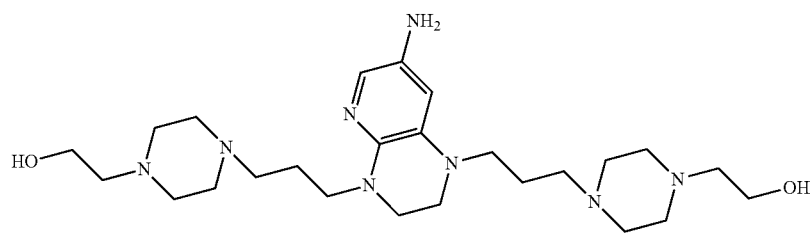

2,2'-[(7-amino-2,3-dihydropyrido[2,3-b]pyrazine-1,4-diyl)bis(propane-3,1-diylpiperazine-4,1-diyl)]diethanol

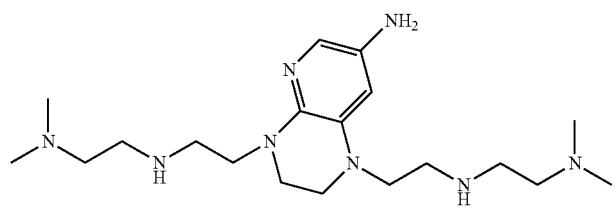

N1,N1'-[(7-amino-2,3-dihydropyrido[2,3-b]pyrazine-1,4-diyl)diethane-2,1-diyl]bis(N2,N2-dimethylethane-1,2-diamine)

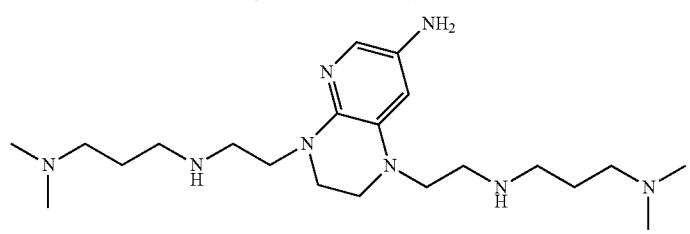

N1,N1'-[(7-amino-2,3-dihydropyrido[2,3-b]pyrazine-1,4-diyl)diethane-2,1-diyl]bis(N3,N3-dimethylpropane-1,3-diamine)

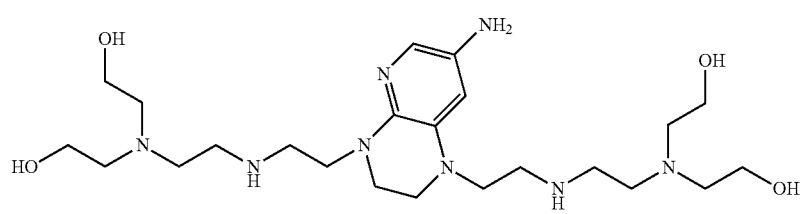

2,2',2'',2'''-[(7-amino-2,3-dihydropyrido[2,3-b]pyrazine-1,4-diyl)bis(ethane-2,1-diyliminoethane-2,1-diylnitrilo)]tetraethanol

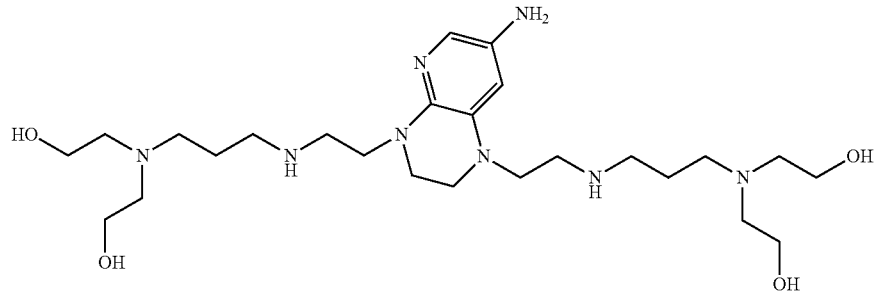
2,2′,2″,2‴-[(7-amino-2,3-
dihydropyrido[2,3-b]pyrazine-1,4-
diyl)bis(ethane-2,1-
diyliminopropane-3,1-
diylnitrilo)]tetraethanol
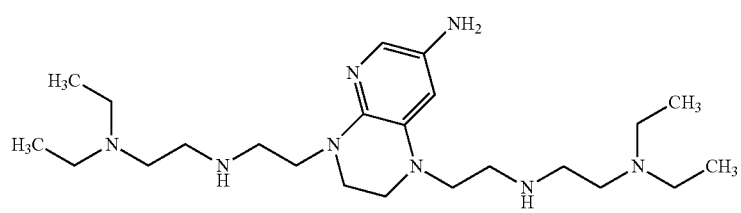
N1,N1′-[(7-amino-2,3-
dihydropyrido[2,3-b]pyrazine-1,4-
diyl)diethane-2,1-diyl]bis(N2,N2-
diethylethane-1,2-diamine)
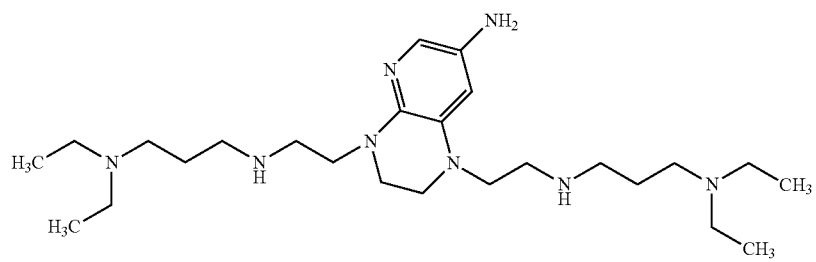
N1,N1′-[(7-amino-2,3-
dihydropyrido[2,3-b]pyrazine-1,4-
diyl)diethane-2,1-diyl]bis(N3,N3-
diethylpropane-1,3-diamine)
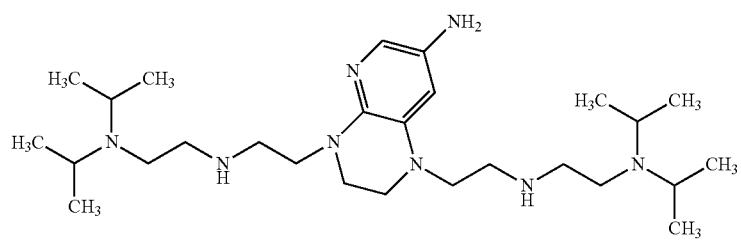
N1,N1′-[(7-amino-2,3-
dihydropyrido[2,3-b]pyrazine-1,4-
diyl)diethane-2,1-diyl]bis[N2,N2-
di(propan-2-yl)ethane-1,2-
diamine]

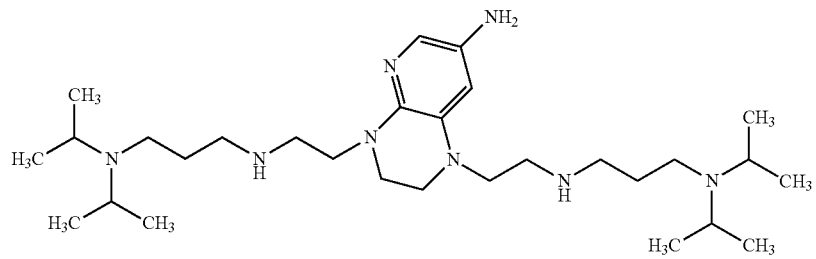
N1,N1'-[(7-amino-2,3-dihydropyrido[2,3-b]pyrazine-1,4-diyl)diethane-2,1-diyl]bis[N3,N3-di(propane-2-yl)propane-1,3-diamine]
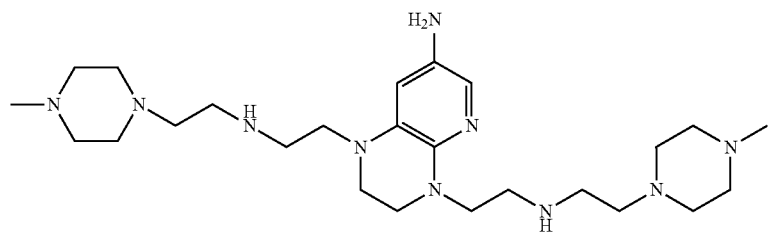
1,4-bis(2-{[2-(4-methylpiperazin-1-yl)ethyl]amino}ethyl)-1,2,3,4-tetrahydropyrido[2,3-b]pyrazin-7-amine
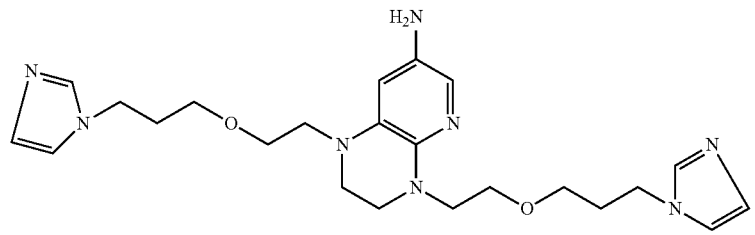
1,4-bis{2-[2-(1H-imidazol-1-yl)ethoxy]ethyl}-1,2,3,4-tetrahydropyrido[2,3-b]pyrazin-7-amine
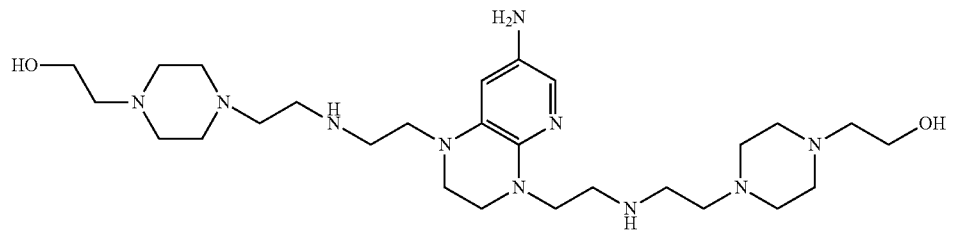
2,2'-[(7-amino-2,3-dihydropyrido[2,3-b]pyrazine-1,4-diyl)bis(ethane-2,1-diyliminoethane-2,1-diylpiperazine-4,1-diyl)]diethanol

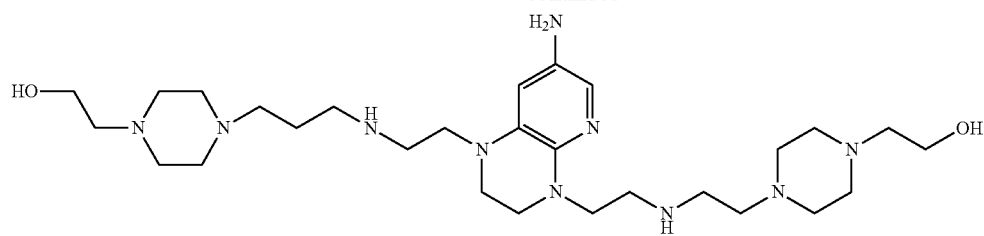

2,2'-[(7-amino-2,3-dihydropyrido[2,3-b]pyrazine-1,4-diyl)bis(ethane-2,1-diyliminopropane-3,1-diylpiperazine-4,1-diyl)]diethanol

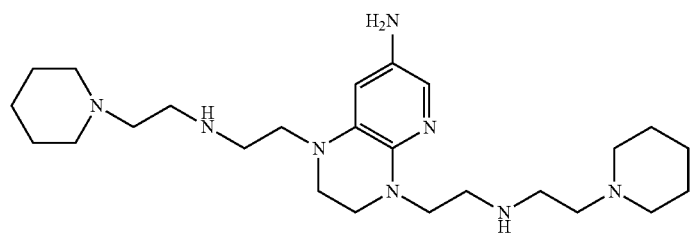

1,4-bis(2-{[2-(piperidin-1-yl)ethyl]amino}ethyl)-1,2,3,4-tetrahydropyrido[2,3-b]pyrazin-7-amine

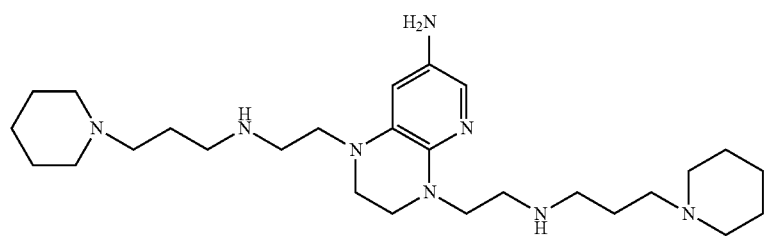

1,4-bis(2-{[3-(piperidin-1-yl)propyl]amino}ethyl)-1,2,3,4-tetrahydropyrido[2,3-b]pyrazin-7-amine

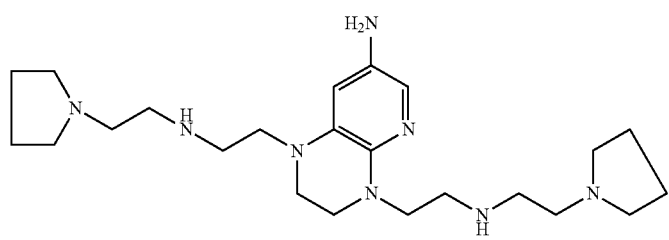

1,4-bis(2-{[2-(pyrrolidin-1-yl)ethyl]amino}ethyl)-1,2,3,4-tetrahydropyrido[2,3-b]pyrazin-7-amine

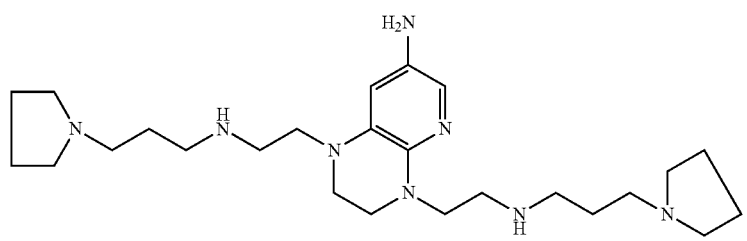

1,4-bis(2-{[3-(pyrrolidin-1-yl)propyl]amino}ethyl)-1,2,3,4-tetrahydropyrido[2,3-b]pyrazin-7-amine -continued
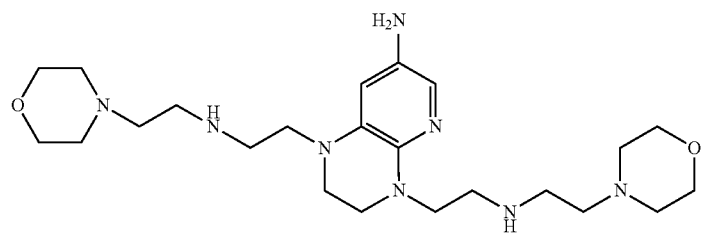
1,4-bis(2-{[2-(morpholin-4-yl)ethyl]amino}ethyl)-1,2,3,4-tetrahydropyrido[2,3-b]pyrazin-7-amine
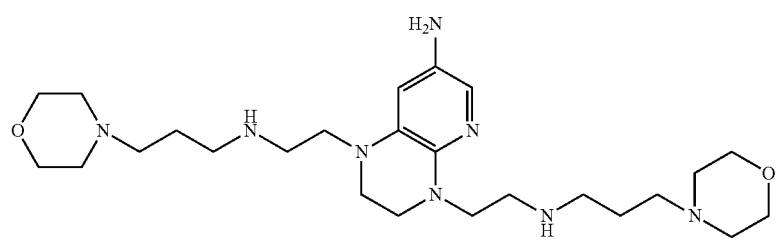
1,4-bis(2-{[3-(morpholin-4-yl)propyl]amino}ethyl)-1,2,3,4-tetrahydropyrido[2,3-b]pyrazin-7-amine
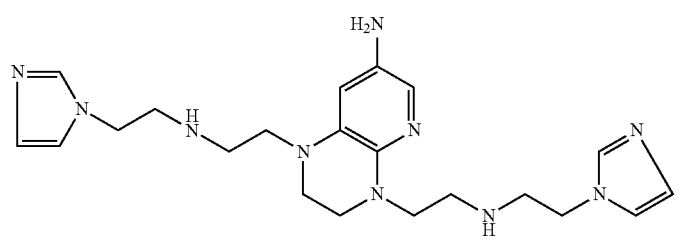
1,4-bis(2-{[2-(1H-imidazol-1-yl)ethyl]amino}ethyl)-1,2,3,4-tetrahydropyrido[2,3-b]pyrazin-7-amine
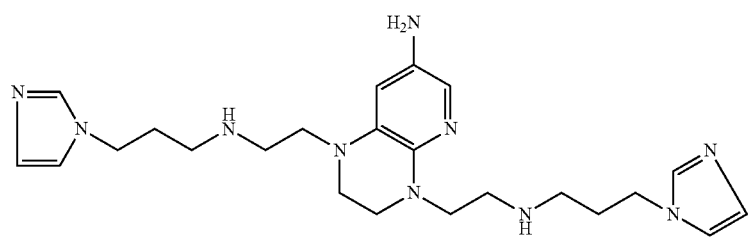
1,4-bis(2-{[3-(1H-imidazol-1-yl)propyl]amino}ethyl)-1,2,3,4-tetrahydropyrido[2,3-b]pyrazin-7-amine
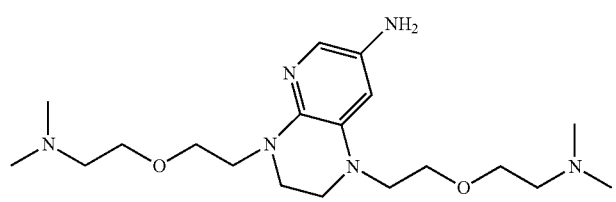
1,4-bis{2-[2-(dimethylamino)ethoxy]ethyl}-1,2,3,4-tetrahydropyrido[2,3-b]pyrazin-7-amine

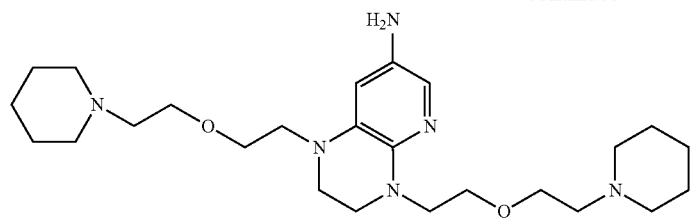

1,4-bis{2-[2-(piperidin-1-yl)ethoxy]ethyl]-1,2,3,4-tetrahydropyrido[2,3-b]pyrazin-7-amine

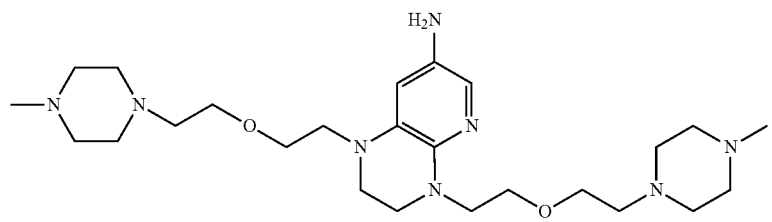

1,4-bis{2-[2-(4-methylpiperazin-1-yl)ethoxy]ethyl}-1,2,3,4-tetrahydropyrido[2,3-b]pyrazin-7-amine

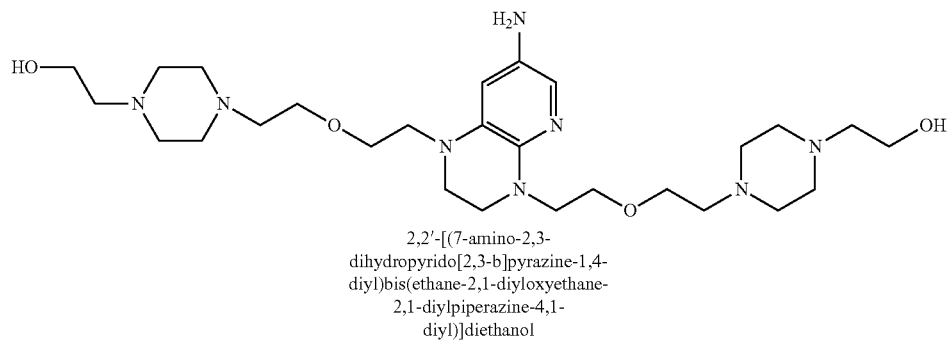

2,2'-[(7-amino-2,3-dihydropyrido[2,3-b]pyrazine-1,4-diyl)bis(ethane-2,1-diyloxyethane-2,1-diylpiperazine-4,1-diyl)]diethanol

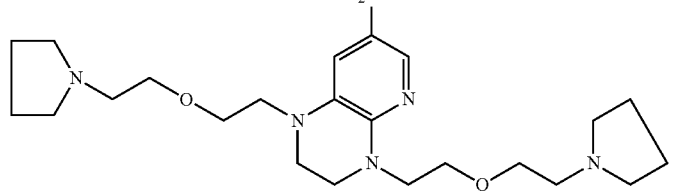

1,4-bis{2-[2-(pyrrolidin-1-yl)ethoxy]ethyl}-1,2,3,4-tetrahydropyrido[2,3-b]pyrazin-7-amine

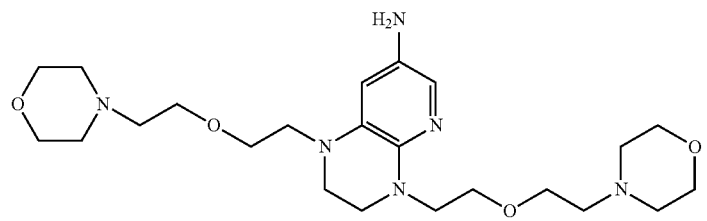

1,4-bis(2-{[2-(morpholin-4-yl)ethyl]amino}ethyl)-1,2,3,4-tetrahydropyrido[2,3-b]pyrazin-7-amine

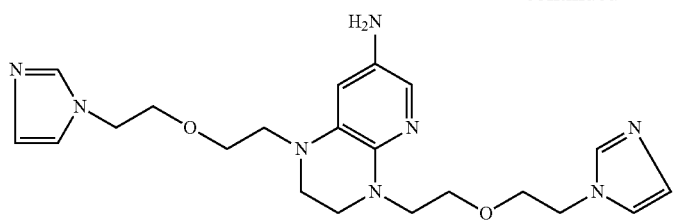
1,4-bis{2-[2-(1H-imidazol-1-yl)ethoxy]ethyl}-1,2,3,4-tetrahydropyrido[2,3-b]pyrazin-7-amine
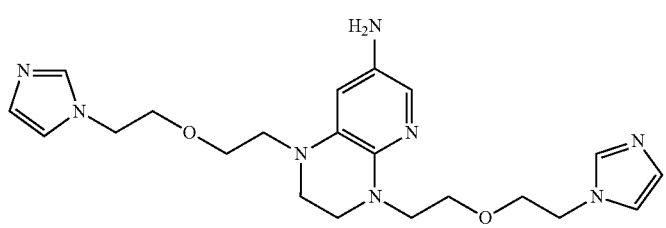
1,4-bis{2-[2-(1H-imidazol-1-yl)ethoxy]ethyl}-1,2,3,4-tetrahydropyrido[2,3-b]pyrazin-7-amine
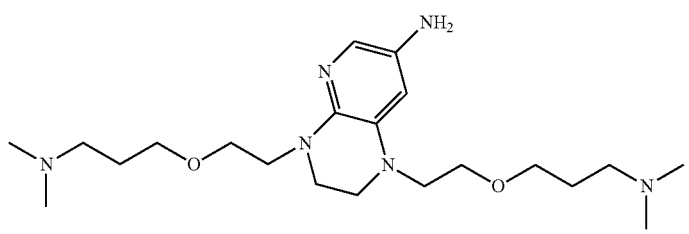
1,4-bis{2-[3-(dimethylamino)propoxy]ethyl}-1,2,3,4-tetrahydropyrido[2,3-b]pyrazin-7-amine
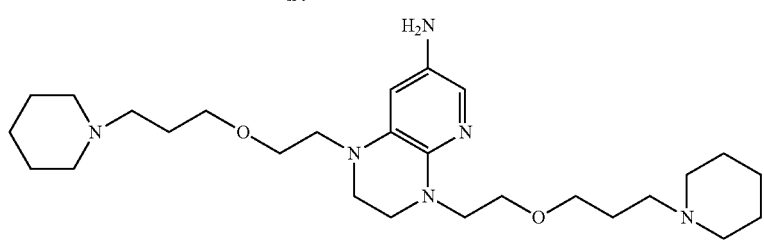
11,4-bis{2-[3-(piperidin-1-yl)propoxy]ethyl}-1,2,3,4-tetrahydropyrido[2,3-b]pyrazin-7-amine
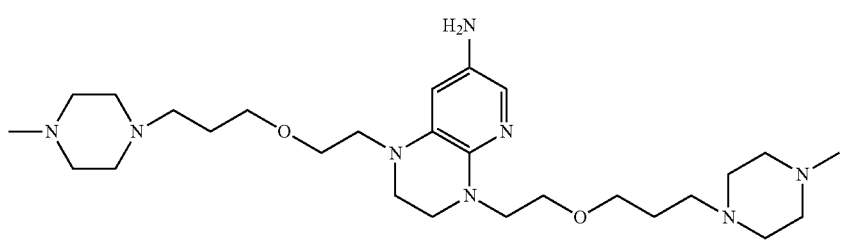
1,4-bis{2-[3-(4-methylpiperazin-1-yl)propoxy]ethyl}-1,2,3,4-tetrahydropyrido[2,3-b]pyrazin-7-amine

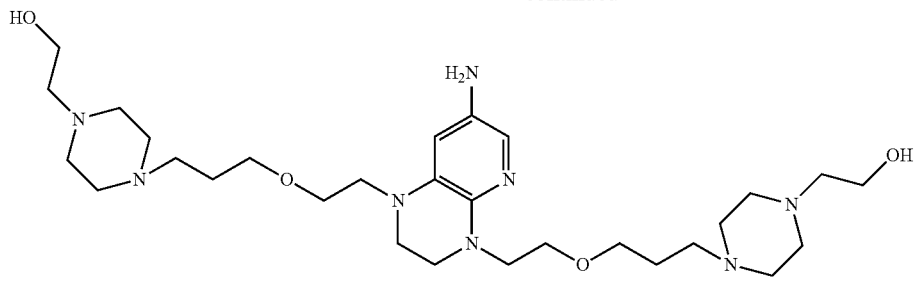

2,2'-[(7-amino-2,3-
dihydropyrido[2,3-b]pyrazine-1,4-
diyl)bis(ethane-2,1-diyloxypropane-
3,1-diyl)piperazine-4,1-
diyl)diethanol

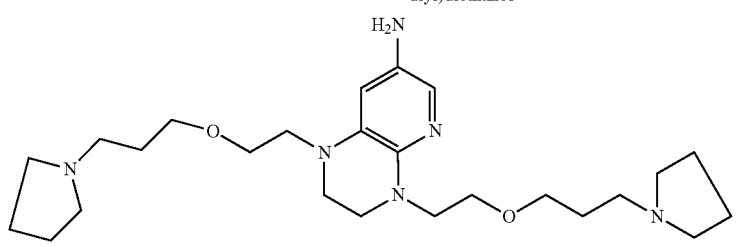

1,4-bis{2-[3-(pyrrolidin-1-
yl)propoxy]ethyl}-1,2,3,4-
tetrahydropyrido[2,3-b]pyrazin-7-
amine

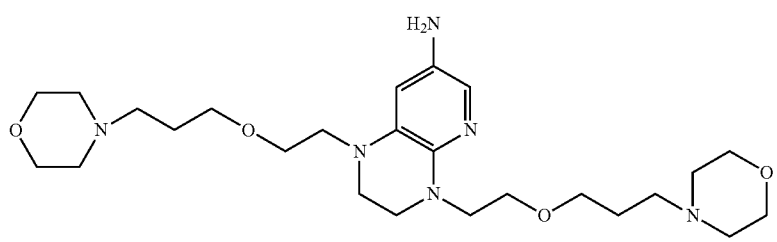

11,4-bis{2-[3-(morpholin-4-
yl)propoxy]ethyl}-1,2,3,4-
tetrahydropyrido[2,3-b]pyrazin-7-
amine

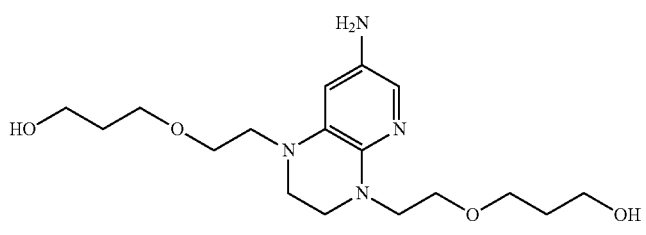

3,3'-[(7-amino-2,3-
dihydropyrido[2,3-b]pyrazine-1,4-
diyl)bis(ethane-2,1-
diyloxy)]dipropan-1-ol

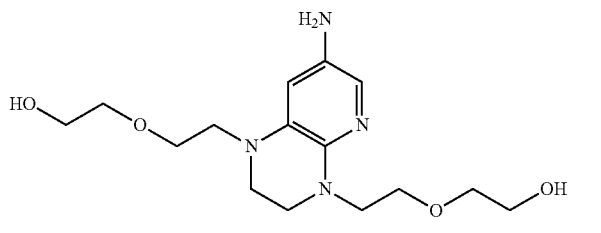

2,2'-[(7-amino-2,3-
dihydropyrido[2,3-b]pyrazine-1,4-
diyl)bis(ethane-2,1-
diyloxy))]diethanol -continued

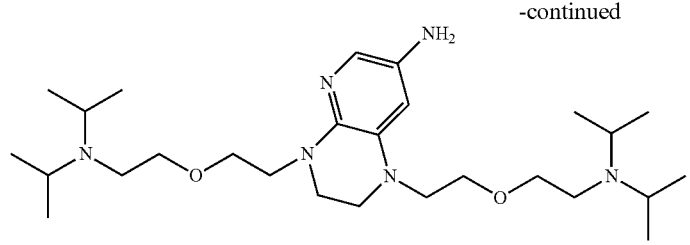

1,4-bis{2-[2-(dipropan-2-ylamino)ethoxy]ethyl}-1,2,3,4-tetrahydropyrido[2,3-b]pyrazin-7-amine

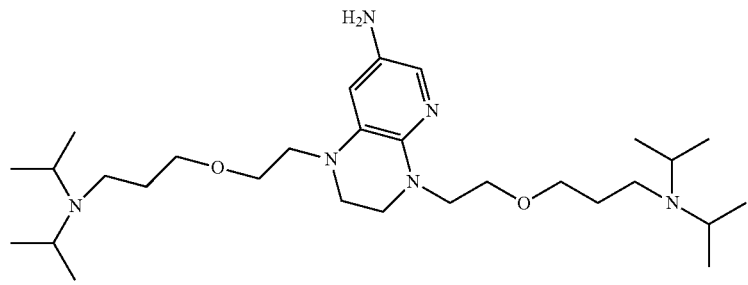

1,4-bis{2-[3-(dipropan-2-ylamino)propoxy]ethyl}-1,2,3,4-tetrahydropyrido[2,3-b]pyrazin-7-amine

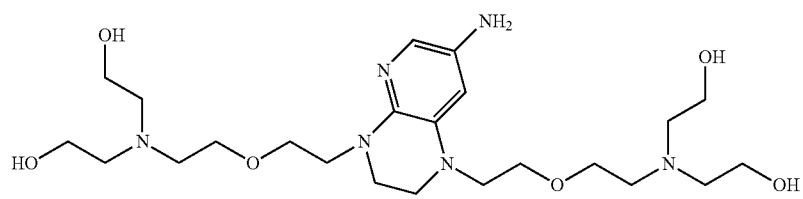

2,2',2'',2'''-[(7-amino-2,3-dihydropyrido[2,3-b]pyrazine-1,4-diyl)bis(ethane-2,1-diyloxyethane-2,1-diylnitrilo)]tetraethanol

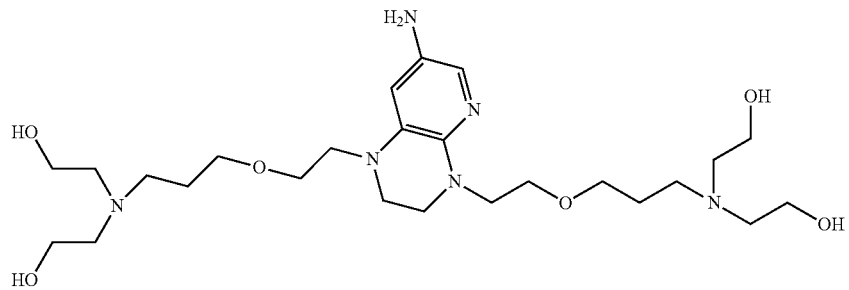

2,2',2'',2'''-[(7-amino-2,3-dihydropyrido[2,3-b]pyrazine-1,4-diyl)bis(ethane-2,1-diyloxypropane-3,1-diylnitrilo)]tetraethanol

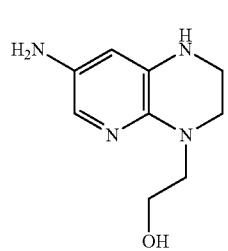

2-(7-amino-2,3-dihydropyrido[2,3b]pyrazin-4(1H)-yl)ethanol

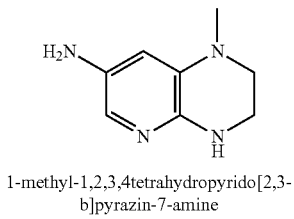

4-methyl-1,2,3,4-tetrahydropyrido[2,3-b]pyrazin-7-amine 1-methyl-1,2,3,4tetrahydropyrido[2,3-b]pyrazin-7-amine

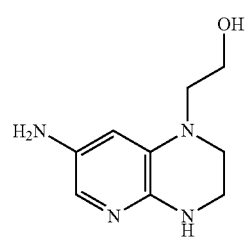
2-(7-amino-3,4-dihydropyrido[2,3-b]pyrazin-1(2H)-yl)ethanol

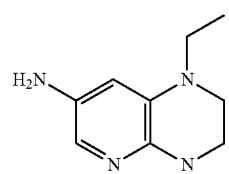
1-ethyl-4-methyl-1,2,3,4-tetrahydropyrido[2,3-b]pyrazin-7-amine

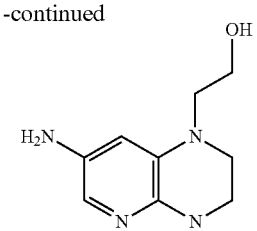
22-(7-amino-4-methyl-3,4-dihydropyrido[2,3-b]pyrazin-1(2H)-yl)ethanol

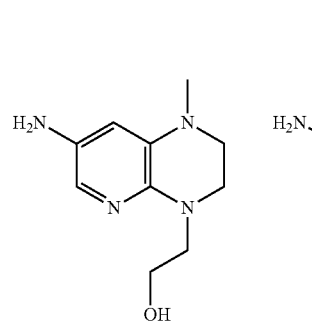
2-(7-amino-1-methyl-2,3-dihydropyrido[2,3-b]pyrazin-4(1H)-yl)ethanol

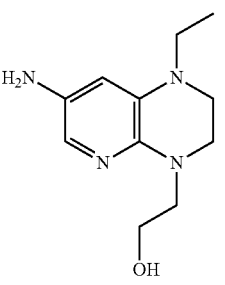
2-(7-amino-1-ethyl-2,3-dihydropyrido[2,3-b]pyrazin-4(1H)-yl)ethanol

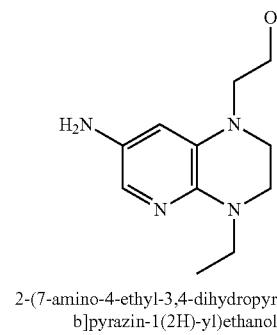
2-(7-amino-4-ethyl-3,4-dihydropyrido[2,3-b]pyrazin-1(2H)-yl)ethanol

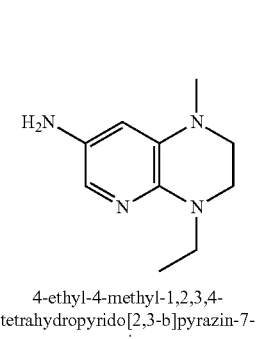
4-ethyl-4-methyl-1,2,3,4-tetrahydropyrido[2,3-b]pyrazin-7-amine or the addition salts thereof, optical isomers thereof, geometrical isomers thereof, tautomers thereof, or solvates thereof.

19. A method for dyeing keratin fibers, the method comprising:

applying to the keratin fibers, alone or in the presence of an oxidizing agent, a composition comprising at least one 1,2,3,4-Tetrahydropyrido[2,3-b]pyrazin-7-amine compound chosen from those of formula (I) or the addition salts thereof, optical isomers thereof, geometrical isomers thereof, tautomers thereof, or solvates thereof:

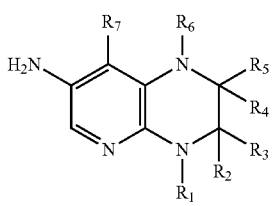

wherein:

$R_2$, $R_3$, $R_4$, $R_5$, and $R_7$, which are identical or different, are independently chosen from:
- a hydrogen or halogen atom;
- a $C_1$-$C_4$ alkyl group;
- a $C_1$-$C_4$ hydroxyalkyl group;
- a carboxyl group; or
- a $(C_1$-$C_4)$alkoxycarbonyl group;

$R_1$ and $R_6$, which are identical or different, are chosen from:
- a hydrogen atom; or
- a $C_1$-$C_{10}$ or $C_1$-$C_6$ alkyl group; optionally interrupted with at least one heteroatom chosen from O, S, or at least one —NR group and/or optionally terminated with at least one —$NX_1X_2$ group or —$OX_3$ group, $X_1$ and $X_2$, which are identical or different, are independently chosen from:
- a hydrogen atom;
- a linear $C_1$-$C_6$ alkyl group;
- a branched $C_3$-$C_6$ alkyl group;
- a linear $C_1$-$C_6$ hydroxyalkyl group; or
- a branched $C_3$-$C_6$ hydroxyalkyl group;
- or $X_1$ and $X_2$ form, together with the nitrogen atom that bears them, a saturated or unsaturated 5- to 8-membered heterocycle, wherein at least one ring member is optionally substituted with a heteroatom chosen from O, S, or N; and/or the heterocycle is optionally substituted with at least one linear or branched $C_1$-$C_4$ alkyl or $C_1$-$C_4$ hydroxyalkyl group;

$X_3$ is chosen from:
- a hydrogen atom; or
- a linear $C_1$-$C_4$ or branched $C_3$-$C_4$ alkyl group; and R is chosen from:
- a hydrogen atom; or
- a linear $C_1$-$C_4$ alkyl group; and leaving the composition on the fibers for a sufficient time to develop the desired color.

20. The method of claim 19, wherein the at least one 1,2,3,4-Tetrahydropyrido[2,3-b]pyrazin-7-amine compound is chosen from:

101
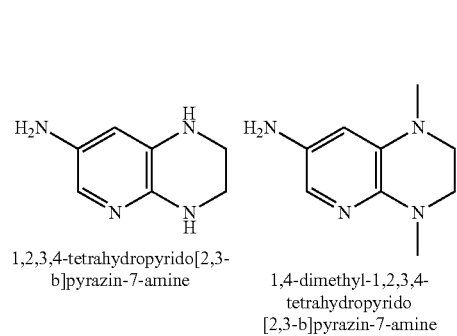
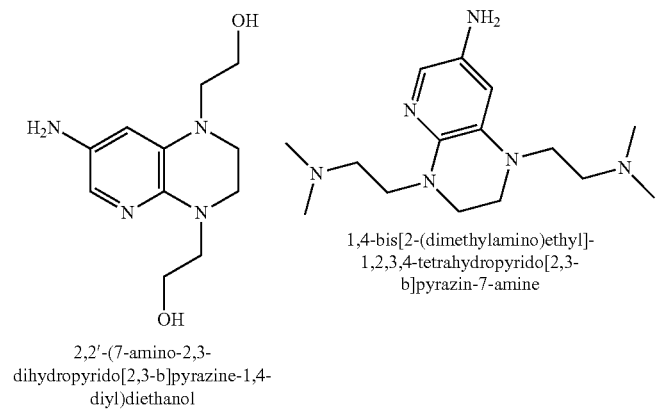
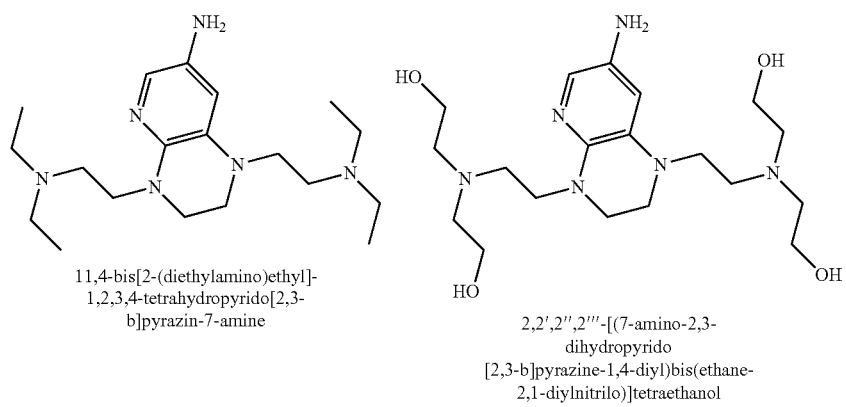
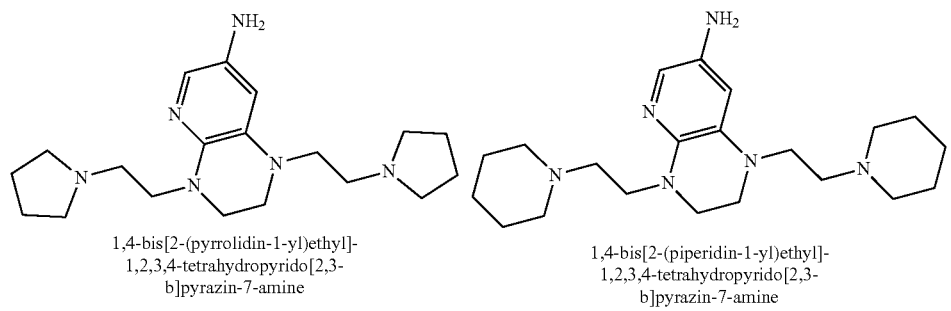
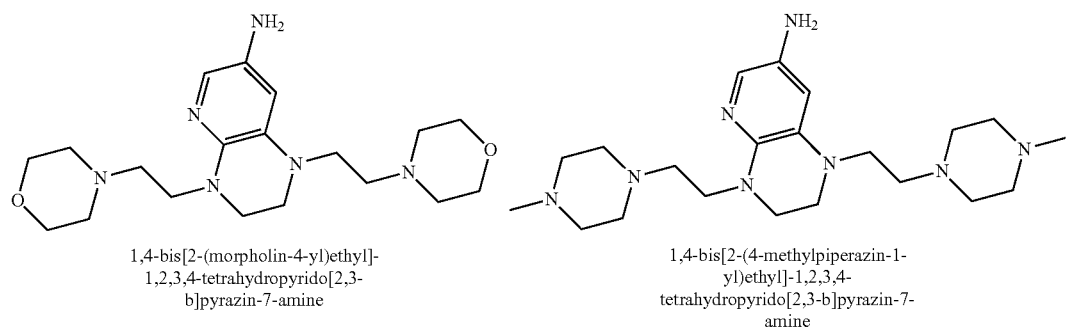

-continued

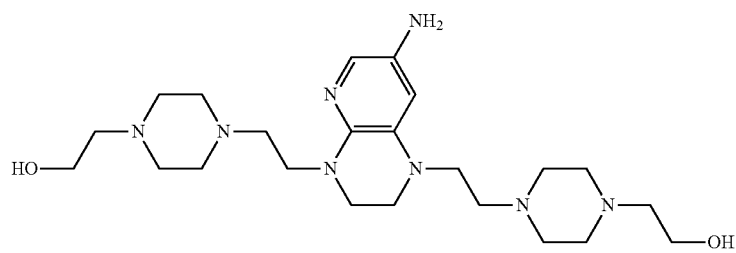

2,2'-[(7-amino-2,3-dihydropyrido[2,3-b]pyrazine-1,4-diyl)bis(ethane-2,1-diylpiperazine-4,1-diyl)]diethanol

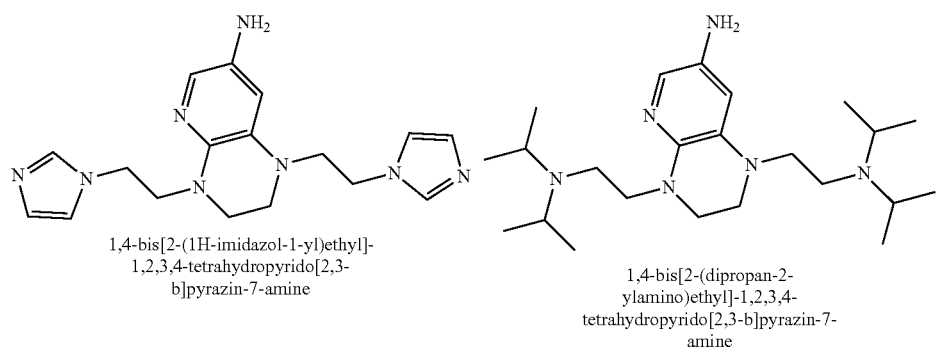

1,4-bis[2-(1H-imidazol-1-yl)ethyl]-1,2,3,4-tetrahydropyrido[2,3-b]pyrazin-7-amine 1,4-bis[2-(dipropan-2-ylamino)ethyl]-1,2,3,4-tetrahydropyrido[2,3-b]pyrazin-7-amine

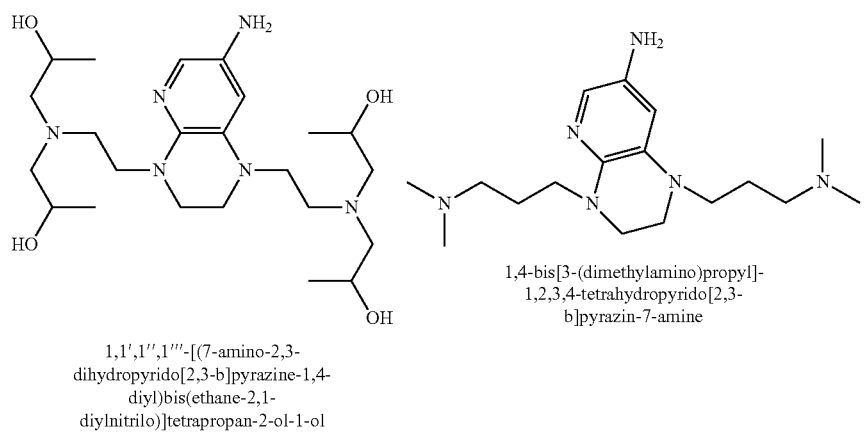

1,1',1'',1'''-[(7-amino-2,3-dihydropyrido[2,3-b]pyrazine-1,4-diyl)bis(ethane-2,1-diylnitrilo)]tetrapropan-2-ol-1-ol 1,4-bis[3-(dimethylamino)propyl]-1,2,3,4-tetrahydropyrido[2,3-b]pyrazin-7-amine

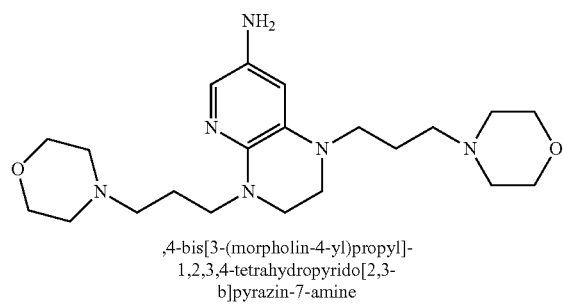

,4-bis[3-(morpholin-4-yl)propyl]-1,2,3,4-tetrahydropyrido[2,3-b]pyrazin-7-amine

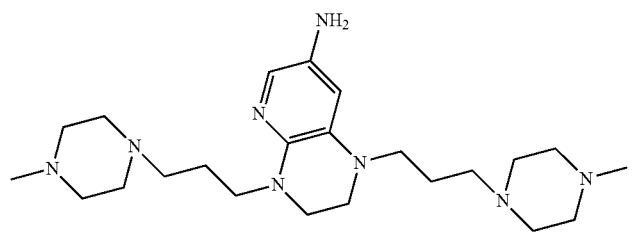

1,4-bis[3-(4-methylpiperazin-1-yl)propyl]-1,2,3,4-tetrahydropyrido[2,3-b]pyrazin-7-amine

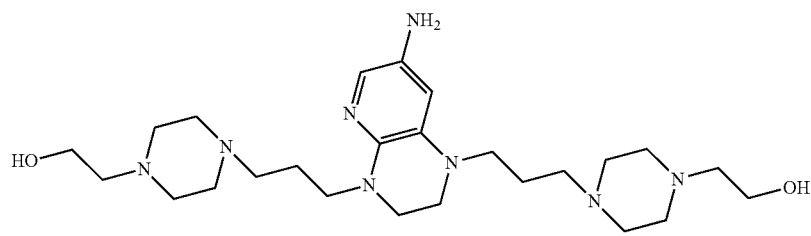

2,2'-[(7-amino-2,3-dihydropyrido[2,3-b]pyrazine-1,4-diyl)bis(propane-3,1-diylpiperazine-4,1-diyl)]diethanol

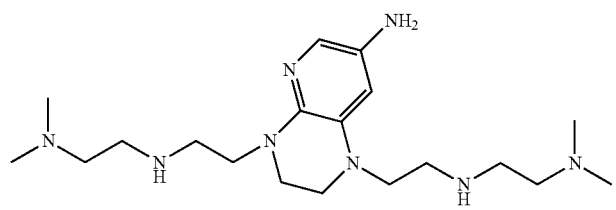

N1,N1'-[(7-amino-2,3-dihydropyrido[2,3-b]pyrazine-1,4-diyl)diethane-2,1-diyl]bis(N2,N2-dimethylethane-1,2-diamine)

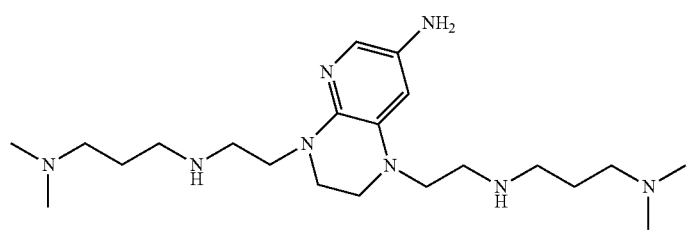

N1,N1'-[(7-amino-2,3-dihydropyrido[2,3-b]pyrazine-1,4-diyl)diethane-2,1-diyl]bis(N3,N3-dimethylpropane-1,3-diamine)

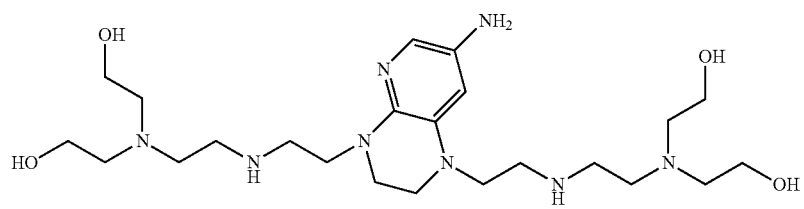

2,2',2'',2'''-[(7-amino-2,3-dihydropyrido[2,3-b]pyrazine-1,4-diyl)bis(ethane-2,1-diyliminoethane-2,1-diylnitrilo)]tetraethanol

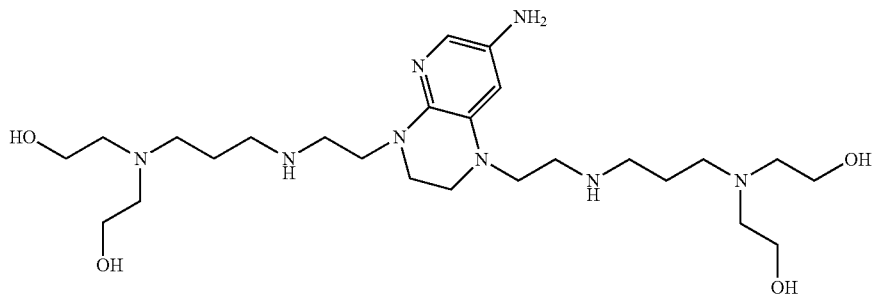

2,2',2'',2'''-[(7-amino-2,3-dihydropyrido[2,3-b]pyrazine-1,4-diyl)bis(ethane-2,1-diyliminopropane-3,1-diylnitrilo)]tetraethanol

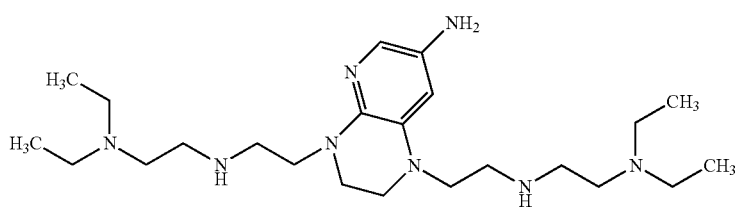

N1,N1'-[(7-amino-2,3-dihydropyrido[2,3-b]pyrazine-1,4-diyl)diethane-2,1-diyl]bis(N2,N2-diethylethane-1,2-diamine)

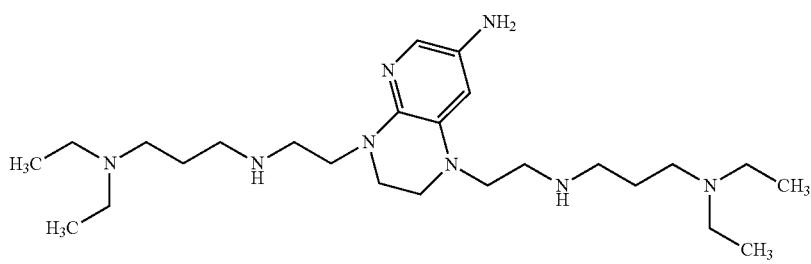

N1,N1'-[(7-amino-2,3-dihydropyrido[2,3-b]pyrazine-1,4-diyl)diethane-2,1-diyl]bis(N3,N3-diethylpropane-1,3-diamine)

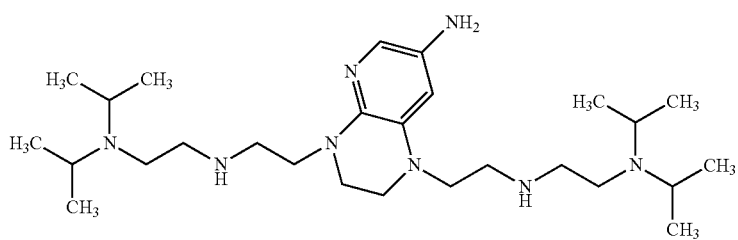

N1,N1'-[(7-amino-2,3-dihydropyrido[2,3-b]pyrazine-1,4-diyl)diethane-2,1-diyl]bis[N2,N2-di(propan-2-yl)ethane-1,2-diamine]

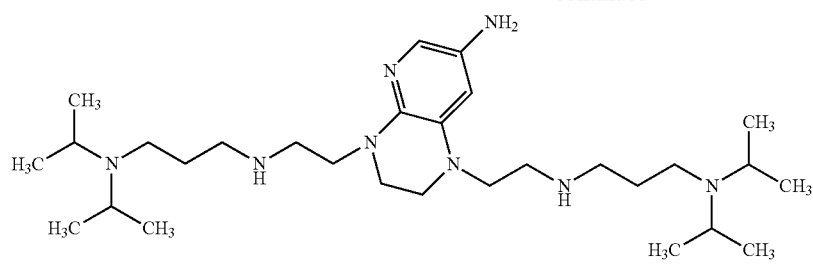
N1,N1'-[(7-amino-2,3-dihydropyrido[2,3-b]pyrazine-1,4-diyl)diethane-2,1-diyl]bis[N3,N3-di(propan-2-yl)propane-1,3-diamine]
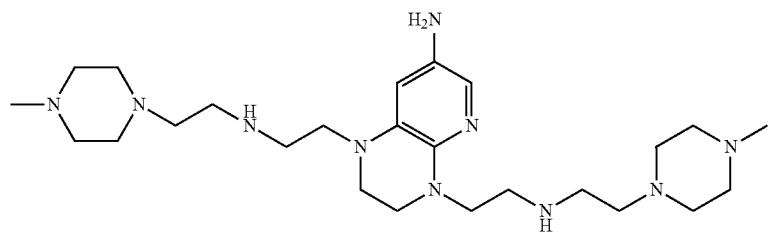
1,4-bis(2-{[2-(4-methylpiperazin-1-yl)ethyl]amino}ethyl)-1,2,3,4-tetrahydropyrido[2,3-b]pyrazin-7-amine
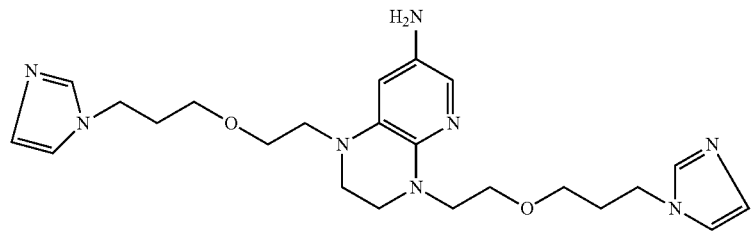
1,4-bis{2-[2-(1H-imidazol-1-yl)ethoxy]ethyl}-1,2,3,4-tetrahydropyrido[2,3-b]pyrazin-7-amine
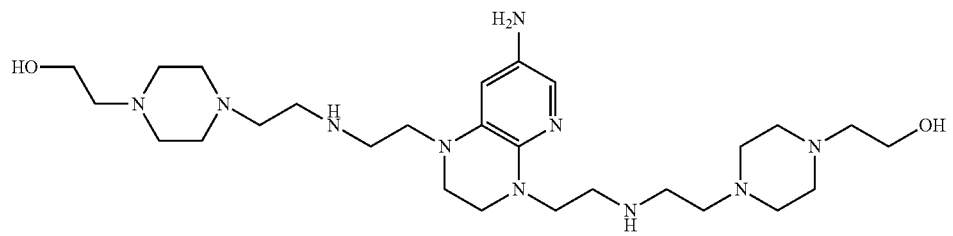
2,2'-[(7-amino-2,3-dihydropyrido[2,3-b]pyrazine-1,4-diyl)bis(ethane-2,1-diyliminoethane-2,1-diylpiperazine-4,1-diyl)]diethanol

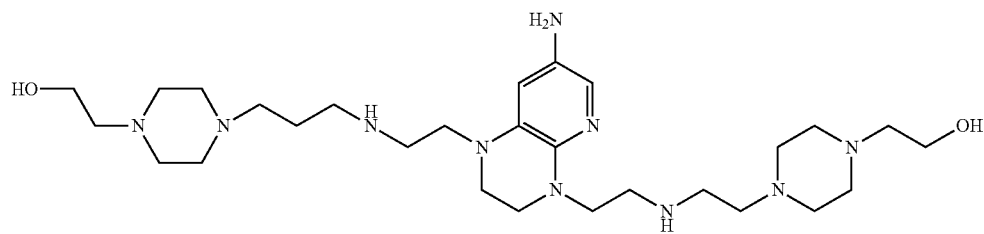

2,2′-[(7-amino-2,3-
dihydropyrido[2,3-b]pyrazine-1,4-
diyl)bis(ethane-2,1-
diyliminopropane-3,1-
diylpiperazine-4,1-diyl)]diethanol

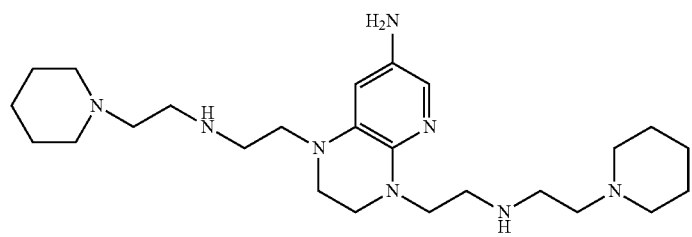

1,4-bis(2-{[2-(piperidin-1-
yl)ethyl]amino}ethyl)-1,2,3,4-
tetrahydropyrido[2,3-b]pyrazin-7-
amine

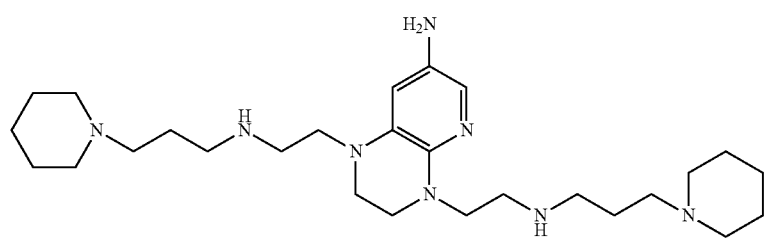

1,4-bis(2-{[3-(piperidin-1-
yl)propyl]amino}ethyl)-1,2,3,4-
tetrahydropyrido[2,3-b]pyrazin-7-
amine

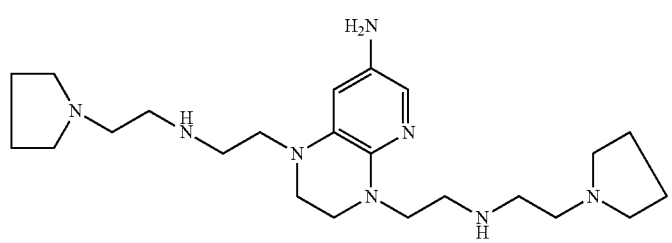

1,4-bis(2-{[2-(pyrrolidin-1-
yl)ethyl]amino}ethyl)-1,2,3,4-
tetrahydropyrido[2,3-b]pyrazin-7-
amine

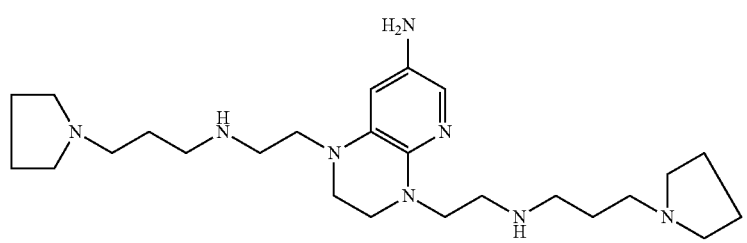

1,4-bis(2-{[3-(pyrrolidin-1-
yl)propyl]amino}ethyl)-1,2,3,4-
tetrahydropyrido[2,3-b]pyrazin-7-
amine

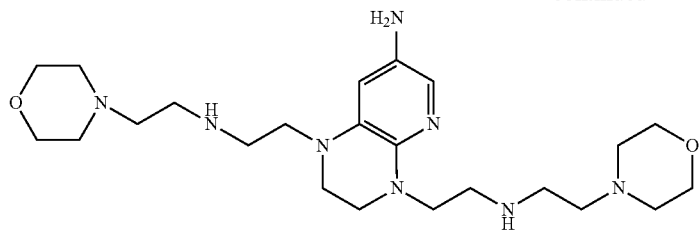
1,4-bis(2-{[2-(morpholin-4-yl)ethyl]amino}ethyl)-1,2,3,4-tetrahydropyrido[2,3-b]pyrazin-7-amine
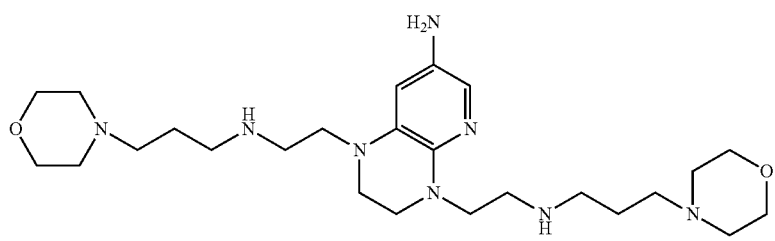
1,4-bis(2-{[3-(morpholin-4-yl)propyl]amino}ethyl)-1,2,3,4-tetrahydropyrido[2,3-b]pyrazin-7-amine
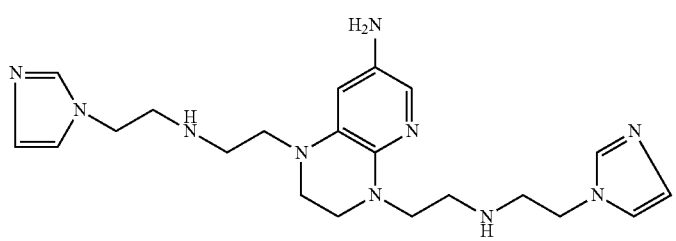
1,4-bis(2-{[2-(1H-imidazol-1-yl)ethyl]amino}ethyl)-1,2,3,4-tetrahydropyrido[2,3-b]pyrazin-7-amine
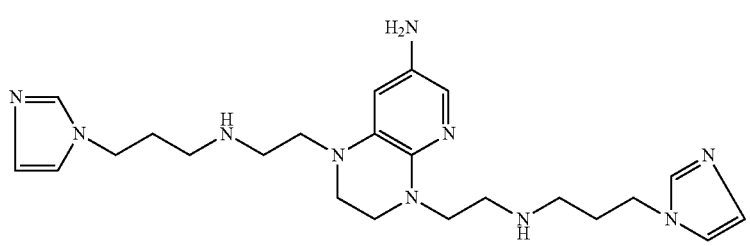
1,4-bis(2-{[3-(1H-imidazol-1-yl)propyl]amino}ethyl)-1,2,3,4-tetrahydropyrido[2,3-b]pyrazin-7-amine
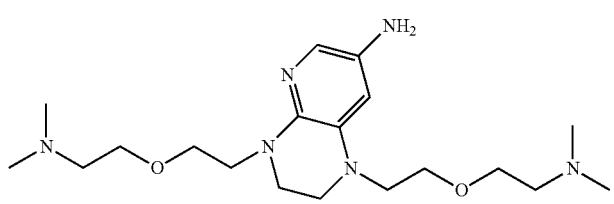
1,4-bis{2-[2-dimethylamino)ethoxy]ethyl}-1,2,3,4-tetrahydropyrido[2,3-b]pyrazin-7-amine -continued

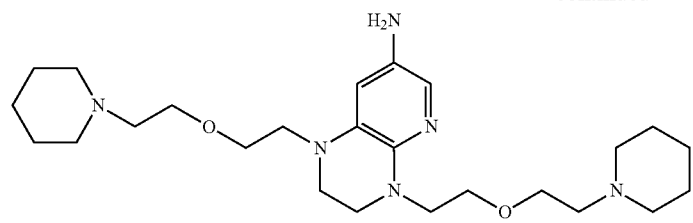

1,4-bis{2-[2-(piperidin-1-
yl)ethoxy]ethyl]-1,2,3,4-
tetrahydropyrido[2,3-b]pyrazin-7-
amine

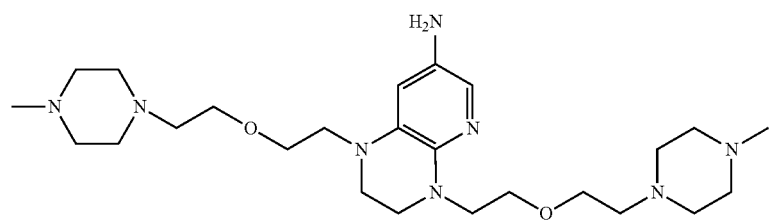

1,4-bis{2-[2-(4-methylpiperazin-1-
yl)ethoxy]ethyl}-1,2,3,4-
tetrahydropyrido[2,3-b]pyrazin-7-
amine

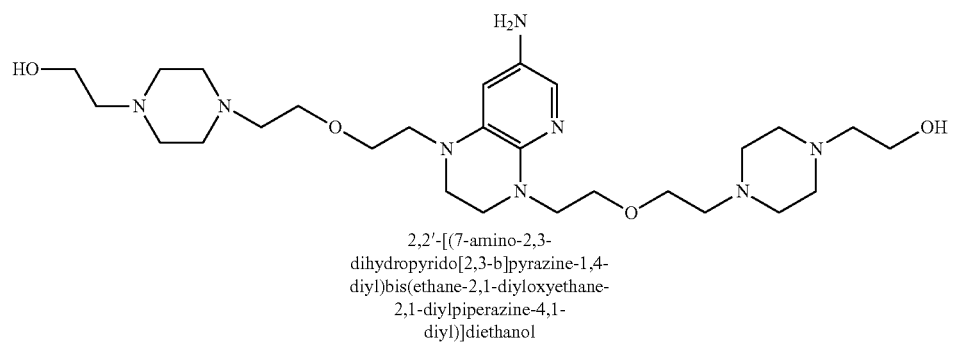

2,2'-[(7-amino-2,3-
dihydropyrido[2,3-b]pyrazine-1,4-
diyl)bis(ethane-2,1-diyloxyethane-
2,1-diylpiperazine-4,1-
diyl)]diethanol

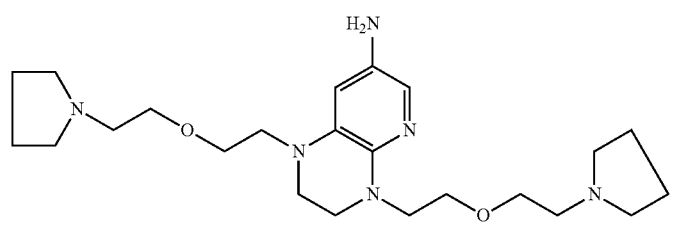

1,4-bis{2-[2-(pyrrolidin-1-
yl)ethoxy]ethyl}-1,2,3,4-
tetrahydropyrido[2,3-b]pyrazin-7-
amine

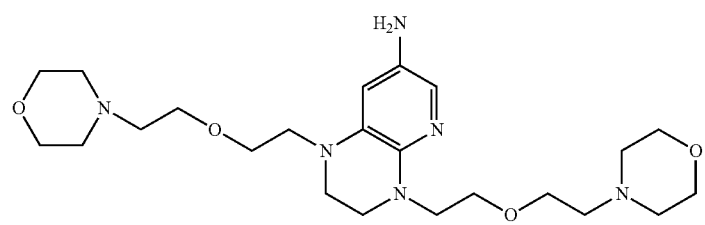

1,4-bis(2-{[2-(morpholin-4-
yl)ethyl]amino}ethyl)-1,2,3,4-
tetrahydropyrido[2,3-b]pyrazin-7-
amine

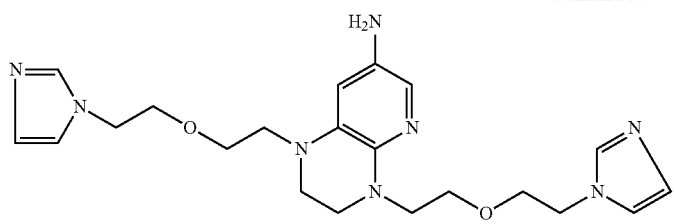
1,4-bis{2-[2-(1H-imidazol-1-yl)ethoxy]ethyl}-1,2,3,4-tetrahydropyrido[2,3-b]pyrazin-7-amine
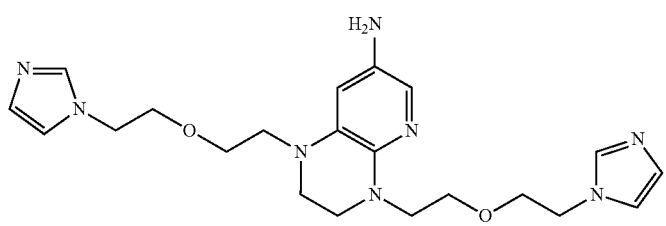
1,4-bis{2-[2-(1H-imidazol-1-yl)ethoxy]ethyl}-1,2,3,4-tetrahydropyrido[2,3-b]pyrazin-7-amine
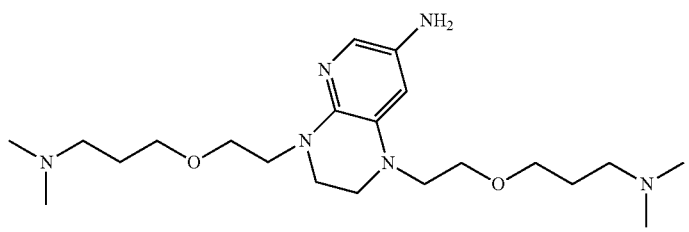
1,4-bis{2-[3-(dimethylamino)propoxy]ethyl}-1,2,3,4-tetrahydropyrido[2,3-b]pyrazin-7-amine
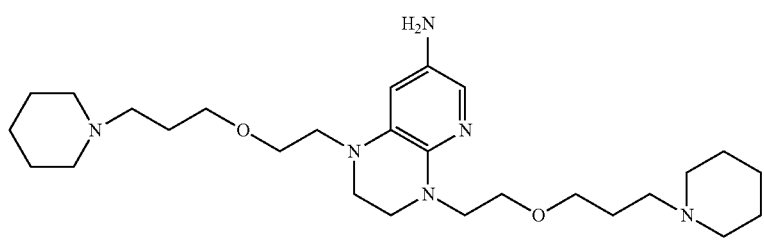
11,4-bis{2-[3-(piperidin-1-yl)propoxy]ethyl}-1,2,3,4-tetrahydropyrido[2,3-b]pyrazin-7-amine
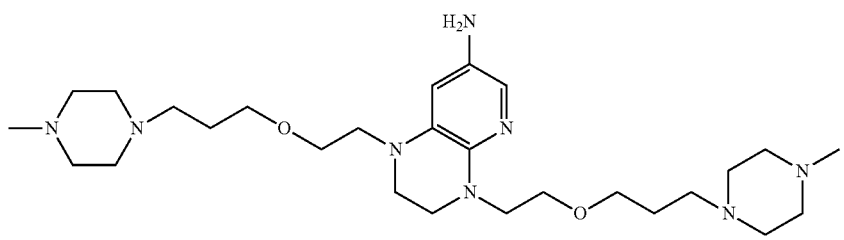
1,4-bis{2-[3-(4-methylpiperazin-1-yl)propoxy]ethyl}-1,2,3,4-tetrahydropyrido[2,3-b]pyrazin-7-amine

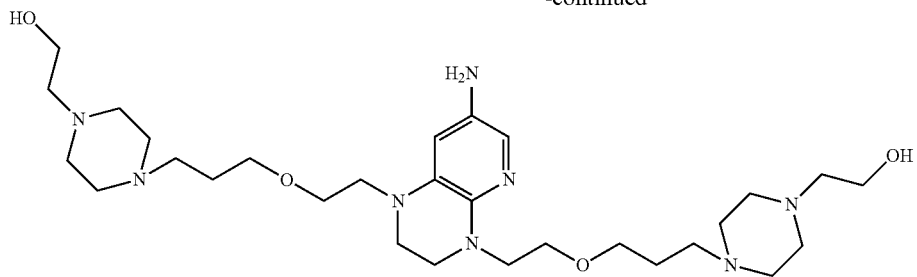

2,2'-[(7-amino-2,3-
dihydropyrido[2,3-b]pyrazine-1,4-
diyl)bis(ethane-2,1-diyloxypropane-
3,1-diyl)piperazine-4,1-
diyl)diethanol

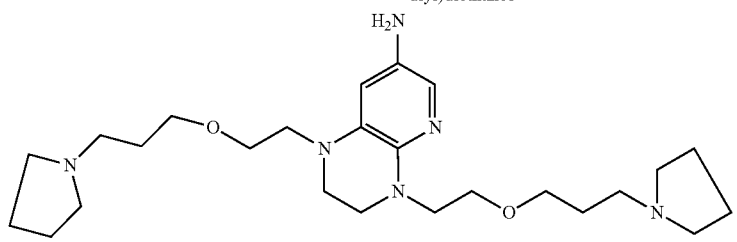

1,4-bis{2-[3-(pyrrolidin-1-
yl)propoxy]ethyl}-1,2,3,4-
tetrahydropyrido[2,3-b]pyrazin-7-
amine

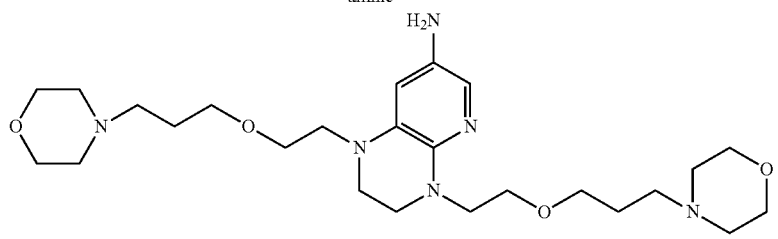

11,4-bis{2-[3-(morpholin-4-
yl)propoxy]ethyl}-1,2,3,4-
tetrahydropyrido[2,3-b]pyrazin-7-
amine

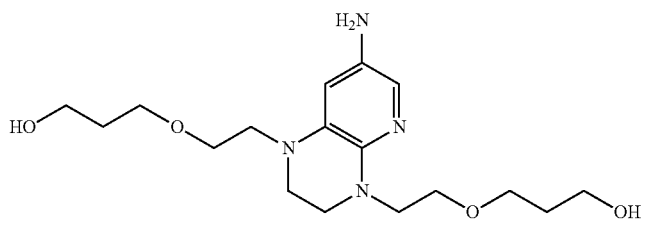

3,3'-[(7-amino-2,3-
dihydropyrido[2,3-b]pyrazine-1,4-
diyl)bis(ethane-2,1-
diyloxy)]dipropan-1-ol

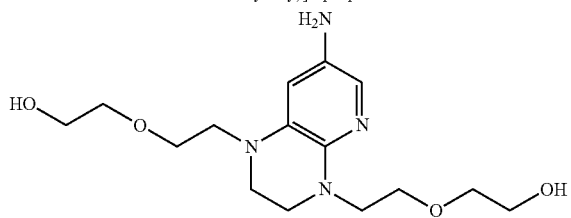

2,2'-[(7-amino-2,3-
dihydropyrido[2,3-b]pyrazine-1,4-
diyl)bis(ethane-2,1-
diyloxy)]diethanol -continued
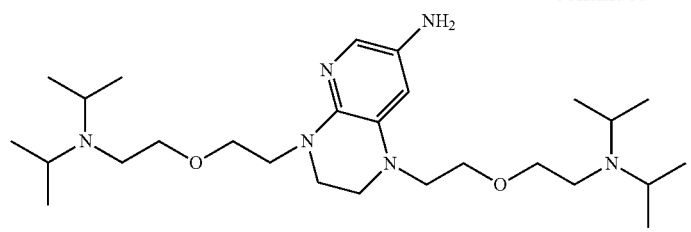
1,4-bis{2-[2-(dipropan-2-ylamino)ethoxy]ethyl}-1,2,3,4-tetrahydropyrido[2,3-b]pyrazin-7-amine
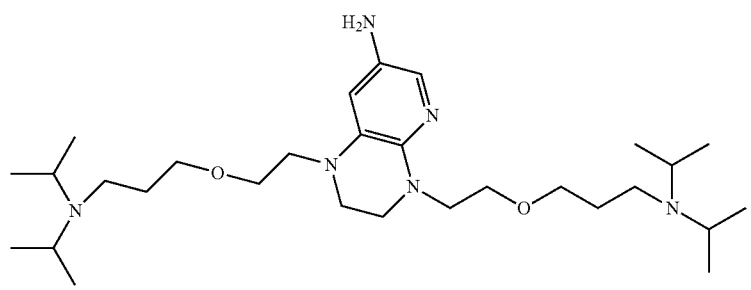
1,4-bis{2-[3-(dipropan-2-ylamino)propoxy]ethyl}-1,2,3,4-tetrahydropyrido[2,3-b]pyrazin-7-amine
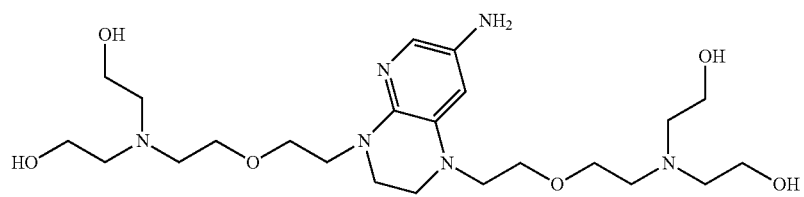
2,2',2'',2'''-[(7-amino-2,3-dihydropyrido[2,3-b]pyrazine-1,4-diyl)bis(ethane-2,1-diyloxyethane-2,1-diylnitrilo)]tetraethanol
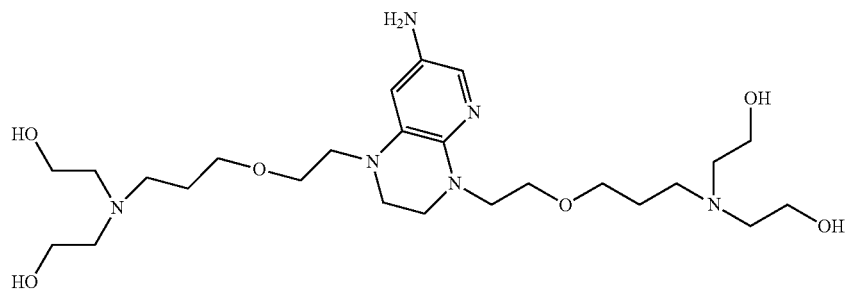
2,2',2'',2'''-[(7-amino-2,3-dihydropyrido[2,3-b]pyrazine-1,4-diyl)bis(ethane-2,1-diyloxypropane-3,1-diylnitrilo)]tetraethanol

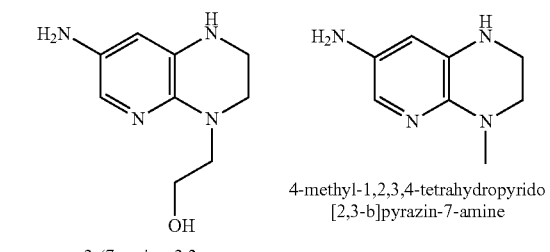

2-(7-amino-2,3-dihydropyrido[2,3b]pyrazin-4(1H)-yl)ethanol 4-methyl-1,2,3,4-tetrahydropyrido[2,3-b]pyrazin-7-amine 1-methyl-1,2,3,4tetrahydropyrido[2,3-b]pyrazin-7-amine

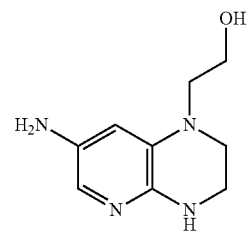

2-(7-amino-3,4-dihydropyrido[2,3-b]pyrazin-1(2H)-yl)ethanol

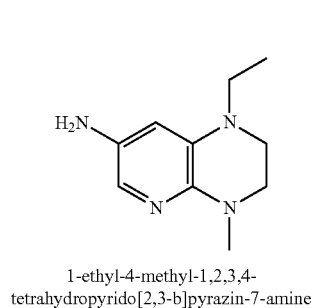

1-ethyl-4-methyl-1,2,3,4-tetrahydropyrido[2,3-b]pyrazin-7-amine

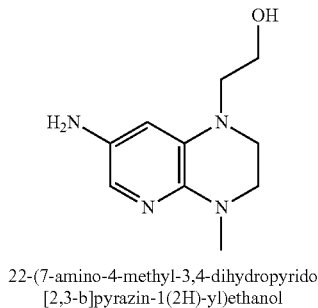

22-(7-amino-4-methyl-3,4-dihydropyrido[2,3-b]pyrazin-1(2H)-yl)ethanol

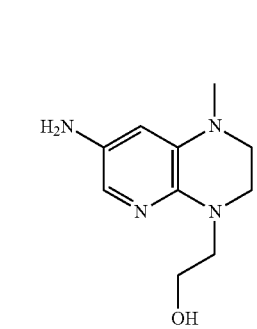

2-(7-amino-1-methyl-2,3-dihydropyrido[2,3-b]pyrazin-4(1H)-yl)ethanol

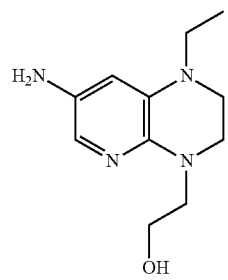

2-(7-amino-1-ethyl-2,3-dihydropyrido[2,3-b]pyrazin-4(1H)-yl)ethanol

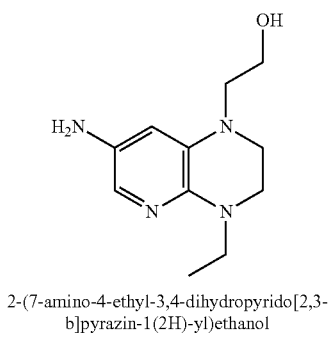

2-(7-amino-4-ethyl-3,4-dihydropyrido[2,3-b]pyrazin-1(2H)-yl)ethanol

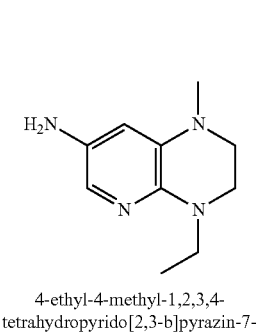

4-ethyl-4-methyl-1,2,3,4-tetrahydropyrido[2,3-b]pyrazin-7-amine or the addition salts thereof, optical isomers thereof, geometrical isomers thereof, tautomers thereof, or solvates thereof.

* * * * *

UNITED STATES PATENT AND TRADEMARK OFFICE
CERTIFICATE OF CORRECTION

PATENT NO.         : 9,980,893 B2
APPLICATION NO.    : 15/106083
DATED              : May 29, 2018
INVENTOR(S)        : Aziz Fadli et al.

Page 1 of 1

It is certified that error appears in the above-identified patent and that said Letters Patent is hereby corrected as shown below:

On the Title Page

Item [57], Line 4, change ".R2," to -- •R2, --.
Item [57], Line 7, change ".R1," to -- •R1 --.
Item [57], Line 22, change ".X3" to -- •X3 --.
Item [57], Line 23, change ".R" to -- •R --.

In the Claims

Column 75, Line 60, Claim 15 change "4-ethyl-1-methyl-1,2,3,4-" to -- 4-ethyl-4-methyl-1,2,3,4- --.

Signed and Sealed this
Second Day of October, 2018

Andrei Iancu
*Director of the United States Patent and Trademark Office*